United States Patent [19]

Lyle et al.

[11] Patent Number: 5,581,687

[45] Date of Patent: Dec. 3, 1996

[54] INTERACTIVE CONTROL SYSTEMS FOR MEDICAL PROCESSING DEVICES

[75] Inventors: Guy A. Lyle, Lake Zurich; William H. Cork, Lake Bluff; Mark C. Weber, West Dundee; David E. Morrow, Chicago, all of Ill.

[73] Assignee: Baxter International Inc., Deerfield, Ill.

[21] Appl. No.: 337,639

[22] Filed: Nov. 10, 1994

[51] Int. Cl.⁶ .................................................. G06F 3/14
[52] U.S. Cl. .......................................................... 395/326
[58] Field of Search ........................... 395/161; 128/771; 342/448; 382/133, 134; 435/4; 436/48

[56] References Cited

U.S. PATENT DOCUMENTS

| | | | |
|---|---|---|---|
| 4,613,866 | 9/1986 | Blood | 342/448 |
| 4,866,638 | 9/1989 | Cosentino et al. | 364/521 |
| 4,995,402 | 2/1991 | Smith et al. | 128/771 |
| 5,041,992 | 8/1991 | Cunningham et al. | 364/518 |
| 5,108,889 | 4/1992 | Smith | 435/4 |
| 5,121,477 | 6/1992 | Koopmans et al. | 395/156 |
| 5,228,123 | 7/1993 | Heckel | 395/155 |
| 5,327,529 | 7/1994 | Fults et al. | 395/155 |
| 5,347,629 | 9/1994 | Barrett et al. | 395/161 |
| 5,353,401 | 10/1994 | Iizawa et al. | 395/161 |
| 5,366,896 | 11/1994 | Margrey et al. | 436/48 |

*Primary Examiner*—Mark R. Powell
*Assistant Examiner*—Ruay Lian Ho
*Attorney, Agent, or Firm*—Daniel D. Ryan; Bradford R. L. Price; Joseph B. Barrett

[57] ABSTRACT

A medical fluid processing device for processing blood or other fluids includes a plurality of hardware elements that perform specific functions. Different processing procedures are achieved by performing the specific functions in appropriately arranged sequences and combinations. A user accessible menu permits user selection of the desired processing procedure. A software implemented "virtual" interface generates appropriate hardware commands for actuating the hardware elements as needed to achieve the desired processing procedure. A dual region, user-accessible screen provides user interaction with the processing device. The "virtual" interface provides positive control over the individual hardware elements in combination with sufficient system flexibility to achieve useful interactivity with the processing device operator.

6 Claims, 17 Drawing Sheets

INTERACTIVE CONTROL SYSTEMS FOR MEDICAL PROCESSING DEVICES

FIELD OF THE INVENTION

The invention relates to control systems and user interfaces for fluid processing systems, such as blood processing systems and the like.

BACKGROUND OF THE INVENTION

Today people routinely separate whole blood by centrifugation into its various therapeutic components, such as red blood cells, platelets, and plasma.

These and other medical processing devices are often controlled using microprocessors with resident program software. The microprocessors also usually include some type of interface through which the operator views and comprehends information regarding the operation of the fluid processing systems.

As the operational and performance demands upon such fluid processing systems become more complex and sophisticated, the need exists for simplifying the control hierarchy of microprocessor based control systems.

As the operational and performance demands also become more complex and sophisticated, the need exists for straightforward, yet higher interactive user interfaces.

SUMMARY OF THE INVENTION

One aspect of the invention addresses the need for simple yet effective control systems. This aspect provides an abstract, "virtual" interface between the software based applications resident in the controller and the hardware elements of the fluid processing system. High level process software resident in the controller communicates with lower level implementing process software in an instrument manager, instead of communicating directly with hardware elements. In this way, the intermediate instrument manager isolates or "hides" all hardware-specific commands from the high level control software. The data flow between the instrument manager and the hardware elements of the system is invisible to the high level software.

The creation of the virtual interface between high level process software and the hardware elements provides considerable flexibility in adding or modifying the process software.

Another aspect of the invention addresses the need for straightforward yet highly interactive user interfaces. This aspect of the invention provides an interface having two distinct viewing regions, called the status region and the working region. Preferably, the two viewing regions are fixed in relative position and unchanging in size on the interface screen. This provides continuity and consistency to the appearance of the interface, even as the functional hardware of the system cycle through different processing modes. The uniformity and consistency of the dual viewing regions of the interface reduce operator confusion and the likelihood of error.

According to the invention, the status region and the working region are each dedicated to different types and levels of information. Nevertheless, the two regions are always displayed simultaneously to provide the operator views of both high level "big picture" information (in the status region) and low level "detailed" information (in the working region).

The two viewing regions also allow the operator to use the interface quickly to find and select among detailed procedures, functions, and options during system operation, or to perform off-line functions, without losing touch with the overall status of the ongoing procedure. The two viewing regions permit the operator to navigate what is in reality a multiple-level menu structure to attend to details on one menu level, without necessarily moving stepwise up and down the menu structure and without losing the ability to, on command, immediately jump between higher and lower menu levels.

The features and advantages of the invention will become apparent from the following description, the drawings, and the claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
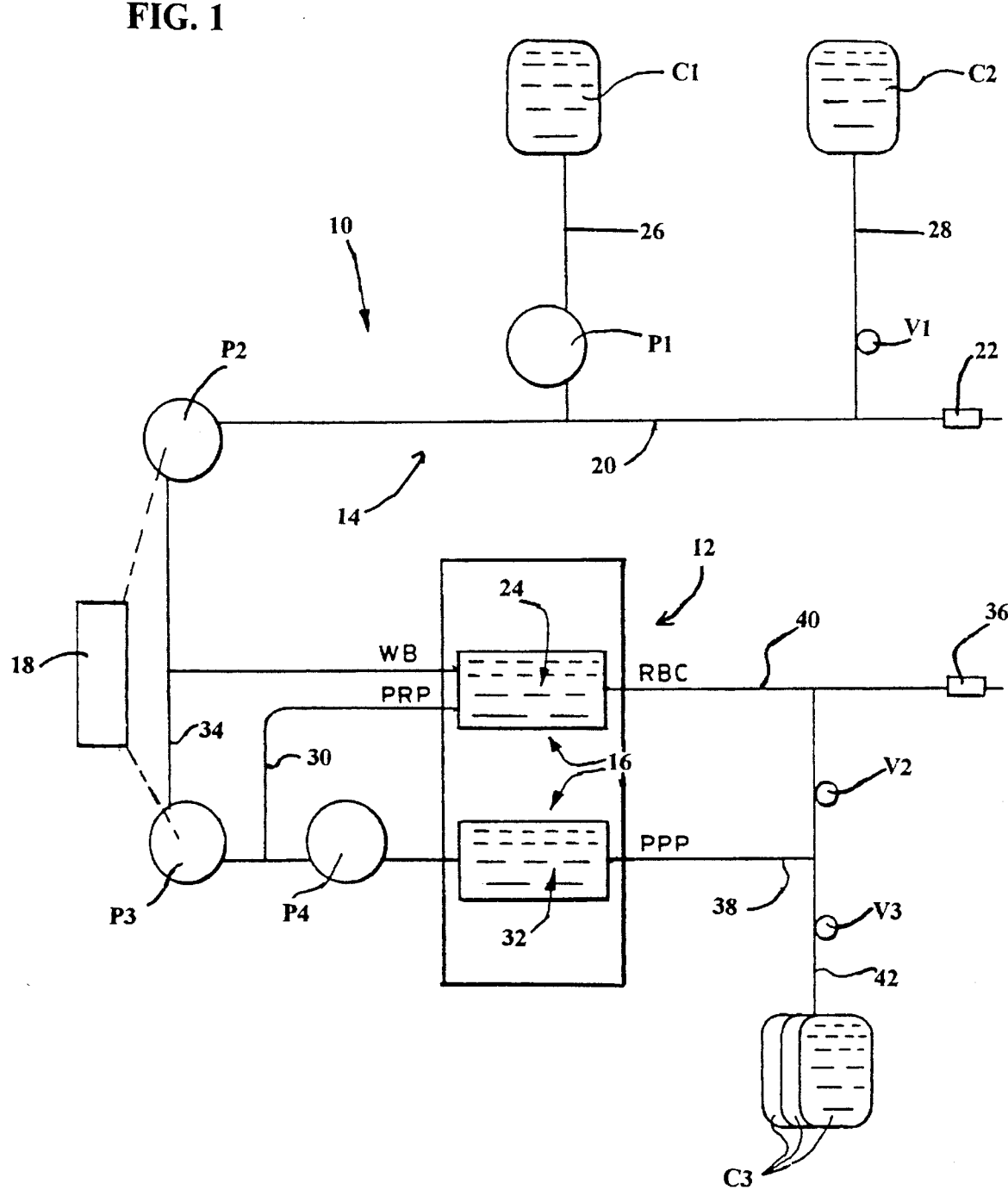
FIG. 1 is a diagrammatic view of a dual needle platelet collection system that includes a controller that embodies the features of the invention.

FIG. 1 shows in diagrammatic form a fluid processing system 10. The system 10 can be used for processing various fluids. The system 10 is particularly well suited for processing fluids for medical purposes, like whole blood and other suspensions of biological cellular materials. Accordingly, the illustrated embodiment shows the system 10 used for this purpose.

I. The Separation System

The system 10 includes an arrangement of durable hardware elements, The hardware elements will vary according to the nature and type of processing system. In the context of processing whole blood, the hardware elements will include a centrifuge 12, in which whole blood (WB) is separated into its various therapeutic components, like platelets, plasma, and red blood cells (RBC). The hardware elements will also include various pumps, which are typically peristaltic (designated P1 to P4); and various in line clamps and valves (designated V1 to V3). Of course, other types of hardware elements will typically be present, which FIG. 1 does not show, like solenoids, pressure monitors, and the like.

The system 10 typically also includes some form of a disposable fluid processing assembly 14 used in association with the hardware elements.

In the illustrated blood processing system 10, the assembly 14 includes a two stage processing chamber 16. In use, the centrifuge 12 rotates the processing chamber 16 to centrifugally separate blood components.

The construction of the two stage processing chamber 16 can vary. For example, it can take the form of double bags, like the processing chambers shown in Cullis et al. U.S. Pat. No. 4,146,172. Alternatively, the processing chamber 16 can take the form of an elongated two stage integral bag, like that shown in Brown U.S. Patent x,xxx,xxx.

In the illustrated blood processing system 10, thee processing assembly 14 also includes an array of flexible tubing that forms a fluid circuit. The fluid circuit conveys liquids to and from the processing chamber 16. The pumps P1–P4 and the valves V1–V3 engage the tubing to govern the fluid flow in prescribed ways. The fluid circuit further includes a number of containers (designated C1 to C3) to dispense and receive liquids during processing.

A controller 18 governs the operation of the various hardware elements to carry out one or more processing tasks using the assembly 14. The invention specifically concerns important attributes of the controller 18.

The system 10 can be configured to accomplish diverse types of blood separation processes. FIG. 1 shows the system 10 configured to carry out an automated two needle platelet collection procedure.

In a collection mode, a first tubing branch 20 and the whole blood inlet pump P2 direct WB from a draw needle 22 into the first stage 24 of the processing chamber 16. Meanwhile, an auxiliary tubing branch 26 meters anticoagulant from the container C1 to the WB flow through the anticoagulant pump P1.

The container C2 holds saline solution. Another auxiliary tubing branch 28 conveys the saline into the first tubing branch 20, via the in line valve V1, for use in priming and purging air from the system 10 before processing begins. Saline solution is also introduced again after processing ends to flush residual components from the assembly 14 for return to the donor.

Anticoagulated WB enters and fills the first stage 24 of the processing chamber 24. There, centrifugal forces generated during rotation of the centrifuge 12 separate WB into red blood cells (RBC) and platelet-rich plasma (PRP).

The PRP pump P4 operates to draw PRP from the first stage 24 of the processing chamber 16 into a second tubing branch 30 for transport to the second stage 32 of the processing chamber 16. There, the PRP is separated into platelet concentrate (PC) and platelet-poor plasma (PPP).

The system 10 includes a recirculation tubing branch 34 and an associated recirculation pump P3. The processing controller 18 operates the pump P3 to divert a portion of the PRP exiting the first stage 24 of the processing chamber 16 for remixing with the WB entering the first stage 24 of the processing chamber 16.

As WB is drawn into the first chamber stage 24 for separation, the illustrated two needle system simultaneously returns RBC from the first chamber stage 24, along with a portion of the PPP from the second chamber stage 32, to the donor through a return needle 36 through tubing branches 38 and 40 and in line valve V2.

The system 10 also collects PC in some of the containers C3 through tubing branches 38 and 42 and in line valve V3 for storage and therapeutic use. The system 10 can also collect PPP in some of the containers C3 through the same fluid path.

II. The System Controller

The controller 18 carries out the overall process control and monitoring functions for the system 10 as just described.

In the illustrated and preferred embodiment (see FIG. 2), the controller comprises a main processing unit (MPU) 44. In the preferred embodiment, the MPU 44 comprises a type 68030 microprocessor made by Motorola Corporation, although other types of conventional microprocessors can be used.

In the preferred embodiment, the MPU 44 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is scheduled.

A. Functional Hardware Control

The MPU 44 includes an application control manager 46. The application control manager 46 administers the activation of a library 48 of control applications (designated A1 to A3). Each control application A1–A3 prescribes procedures for carrying out given functional tasks using the system hardware (e.g., the centrifuge 12, the pumps P1–P4, and the valves V1–V3) in a predetermined way. In the illustrated and preferred embodiment, the applications A1–A3 reside as process software in EPROM's in the MPU 44.

The number of applications A1–A3 can vary. In the illustrated and preferred embodiment, the library 48 includes at least one clinical procedure application A1. The procedure application A1 contains the steps to carry out one prescribed clinical processing procedure. For the sake of example in the illustrated embodiment, the library 48 includes a procedure application A1 for carrying out the dual needle platelet collection process, as already generally described in connection with FIG. 1. Of course, additional procedure applications can be, and typically will be, included. For example, the library 48 can include a procedure application for carrying out a conventional single needle platelet collection process.

In the illustrated and preferred embodiment, the library 48 also includes at least one additional, non-procedure application. The non-clinical procedural application contains the procedures to carry out a system configuration or support utility. For the sake of example in the illustrated embodiment, the library 48 includes a configuration application A2, which contains the procedures for allowing the operator to configure the default operating parameters of the system 10. The library 48 also includes a main menu application A3, which coordinates the selection of the various applications A1–A3 by the operator, as will also be described in greater detail later.

Of course, additional non-clinical procedure applications can be, and typically will be, included. For example, the library 48 can include a diagnosis application, which contains the procedures aiding service personnel in diagnosing and troubleshooting the functional integrity of the system, and a system restart application, which performs a full restart of the system, should the system become unable to manage or recover from an error condition.

An instrument manager 50 also resides as process software in EPROM's in the MPU 44. The instrument manager 50 communicates with the application control manager 46. The instrument manager 50 also communicates with low level peripheral controllers 52 for the pumps, solenoids, valves, and other functional hardware of the system.

Figure 3:
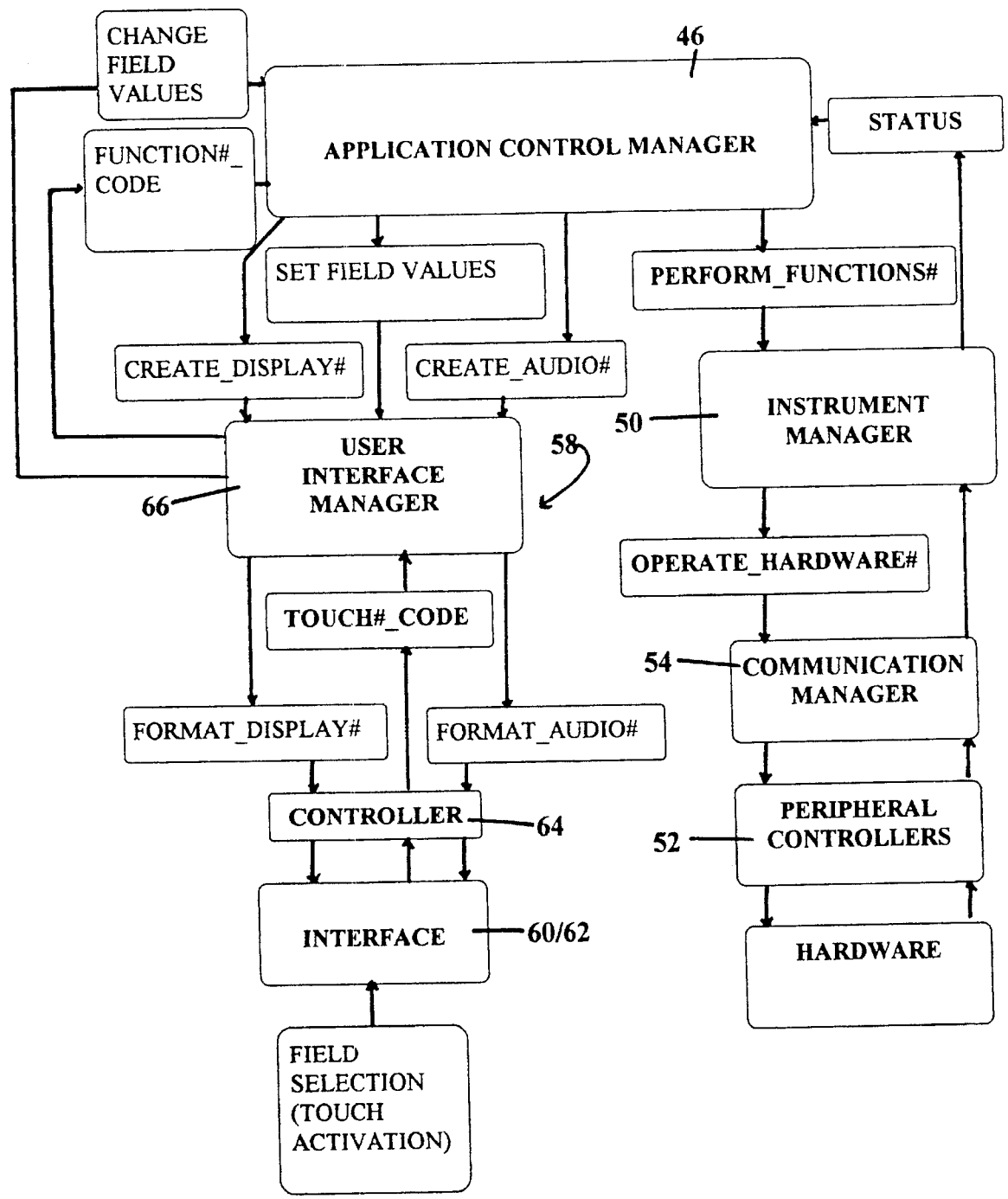
FIG. 3 is another diagrammatic view of the controller and associated interface shown in FIG. 2, and further showing the command and status flow hierarchy.

As FIG. 3 shows, the application control manager 46 sends specified commands in abstract form to the instrument manager 50, as called up by the activated application A1–A3. In response to these abstract commands, (that will be referred to herein as "Perform_Function# commands,") the instrument manager 50 identifies the peripheral controller or controllers 52 for performing the function and compiles hardware-specific commands (that will be referred to herein as "Operate_Hardware# commands") into the command tables for the particular peripheral controllers 52. The peripheral controllers 52 communicate directly with the hardware to implement the hardware-specific commands generated by the instrument manager 50, causing the hardware to operate in a specified way to carry out the abstract Perform_Function# commands. A communication manager 54 manages low-level protocol and communications between the instrument manager 50 and the peripheral controllers 52.

As FIG. 3 also shows, the instrument manager 50 also conveys back to the application control manager 46 status data about the operational and functional conditions of the processing procedure. The status data is expressed in terms of, for example, fluid flow rates, sensed pressures, and fluid volumes measured.

The application control manager 46 processes and uses the status data in various ways. In one way, the application control manager 46 transmits selected status data for display to the operator, as will be described later. In another way, the application control manager 46 monitors operational and functional conditions using the status data to detect abnormal system conditions requiring operator intervention or system shutdown, as will also be described in greater detail later.

In the preferred embodiment (see FIG. 2), the MPU 44 also includes a condition manager 56 that resides in the data flow path between the instrument manager 50 and the communications manager 54. The condition manager 56 also monitors status data and other operational states of the hardware to detect abnormal conditions that are either not detected or are left uncorrected by the application control manager 46. Upon detecting such abnormal conditions, the condition manager 56 provides fail-safe support by suspending system operation. Further details of this fail-safe function and other related aspects of the controller 18 will be described later.

The described control hierarchy creates an abstract, "virtual" interface between the applications resident in the application control manager 46 and the hardware elements of the system 10. The high level process software resident in the application control manager 46 communicates with lower level implementing process software in the instrument manager 50, instead of communicating directly with hardware elements. In this way, the intermediate instrument manager 50 isolates or "hides" all hardware-specific commands from the application control manager 46. The applications pass abstract Perform_Function# commands to the instrument manager 50, and the instrument manager 50 converts these abstract commands into the specific Operate_Hardware# commands unique to the particular hardware elements, all without further participation by the procedure applications A1–A3 themselves. The data flow between the instrument manager 50 and the hardware elements of the system 10 is invisible to the activated application A1–A3.

The creation of the virtual interface between high level process software and the hardware elements provides considerable flexibility in adding or modifying the process software of the high level applications A1–A3 for controlling hardware functions. New or modified process software for the applications need only to include specified hardware-non-specific abstract Perform_Function# commands to gain immediate linkage to the virtual hardware interface. Likewise, addition or modification of specific hardware requires only changes to the low level process software of the instrument manager 50. Because of the virtual interface, hardware changes require minimal changes to the high level software in the application control manager 46.

As described above, the instrument manager 50 forms a part of the same MPU in which the application control manager 46 resides. Alternatively, because of the virtual nature of the interface, the instrument manager 50 can reside on a separate processing unit.

B. User Interface Control

In the illustrated embodiment, the MPU 44 also includes an interactive user interface 58. The interface 58 allows the operator to view and comprehend information regarding the operation of the system 10. The interface 58 also allows the operator to select applications residing in the application control manager 46, as well as to change certain functions and performance criteria of the system 10.

The interface 58 includes an interface screen 60 and, preferably, an audio device 62. The interface screen 60 displays information for viewing by the operator in alpha-numeric format and as graphical images. The audio device 62 provides audible prompts either to gain the operator's attention or to acknowledge operator actions.

In the illustrated and preferred embodiment, the interface screen 60 also serves as an input device. It receives input from the operator by conventional touch activation, as will be described later. Alternatively or in combination with touch activation, a mouse or keyboard could be used as input devices.

An interface controller 64 communicates with the interface screen 60 and audio device 62. The interface controller 64, in turn, communicates with an interface manager 66, which in turn communicates with the application control manager 46. The interface controller 64 and the interface manager 66 reside as process software in EPROM's in the MPU 44.

In use, the application control manager 46 sends to the interface manager 66 specified field values reflecting selected status data received from the instrument manager 50. The application control manager 46 also sends to the interface manager 66 prescribed abstract Create_Display# and Create_Audio# commands called for by the activated application.

The interface manager 66 processes these field values and the abstract Create_Display# commands to generate specific Format_Display# commands. The Format_Display# commands control the particular format, attributes, and protocols necessary to create, refresh, and close the visual display on the interface screen 60.

Likewise, the interface manager 66 processes the abstract Create_Audio# commands to generate specific Format_Audio# commands. The Format_Audio# commands dictate the format and attributes of the audio output called for by the activated application.

The interface manager 66 conveys the processed Format_Display# and _Audio# commands to the interface controller 64. The interface controller 64 provides low level control functions that draw boxes and lines, forms text or graphical characters, and provides the formatting attributes of the display on the interface screen 60. The interface controller 64 also provides low level control functions that drive the audio device 62 based upon Format_Audio# commands received from the interface manager 66.

The interface controller 64 also accepts Field#_Select commands generated by touch activation of the interface screen 60, as will be described in greater detail later. The interface controller 64 passes this touch activated input to the interface manager 66 in the form of Touch#_Codes. The interface manager 66 processes the Touch#_Codes to the application control manager 46, either as function codes or as changed field values. The application control manager 46 implements the function codes or changed field values and passes them to the instrument manager 50. Further details of this will be provided later.

This control hierarchy also creates an abstract, "virtual" interface between the functional processors of the controller 18 and the interface 58. The high process software of the interface manager 66 isolates and "hides" all formatting and protocol issues used in creating the interface 58 from the applications used to control hardware functions of the system 10. The process software of the applications A1–A3, through the application control manager 46, pass abstract field values and Create_Display# and Create_Audio# commands to the interface manager 66. The process software of the interface manager 66 converts these abstract commands into the specific commands that control the textual and graphic formats and audio formats of the operator interface 58, without further participation by the procedure applications A1–A3 themselves. The data flow between the interface manager 66 and the interface controller 64 is invisible to the data flow between the application control manager 46 and the instrument manager 50.

This control hierarchy lends further flexibility in adding or modifying applications for controlling hardware functions. New or modified applications need only to include textual field value outputs and the prescribed Create_Display# or Create_Audio# commands to gain immediate linkage to the operator interface.

(i) Interface Screen Format

In the illustrated and preferred embodiment (see FIG. 4), the Format_Display# commands of the interface manager 66 formats information for display on the interface screen 60 in two distinct viewing regions, called the status region 68 and the working region 70. Preferably, the two viewing regions 68 and 70 are fixed in relative position and unchanging in size on the interface screen 60. This provides continuity and consistency to the appearance of the interface 58, even as the functional hardware of the system cycle through different processing modes. The uniformity and consistency of the dual viewing regions 68 and 70 of the interface 58 reduce operator confusion and the likelihood of error.

The status region 68 and the working region 70 are each dedicated to different types and levels of information. Nevertheless, the two regions 68 and 70 are always displayed simultaneously to provide the operator views of both high level "big picture" information and low level "detailed" information.

The working region 70 provides the means for the operator to select and activate any one of the system-resident applications A1–A3. The working region 70 displays all specific procedure-dependent information then called for by the Create_Display# commands generated by the activated application A1–A3. The considerable detail of information displayed in the working region 70 allows the operator to monitor and change the ongoing process in real time.

On the other hand, the status region 68 continuously shows prescribed procedure-dependent information of a more general and "overview" nature, about which an operator routinely needs continuous knowledge and immediate access. The status region 68 continuously displays this general information to keep the operator appraised of the overall status of the ongoing process, even when the operator is using the working region 70 to monitor and change more detailed aspects of the processes. In the illustrated and preferred embodiment, the status region 68 also provides means for the operator to respond to alarms or malfunctions.

The two viewing regions 68 and 70 allow the operator to use the interface 58 quickly to find and select among detailed procedures, functions, and options during system operation, or to perform off-line functions, without losing touch with the overall status of the ongoing procedure. The two viewing regions 68 and 70 permit the operator to navigate what is in reality a multiple-level menu structure to attend to details on one menu level, without necessarily moving stepwise up and down the menu structure and without losing the ability to, on command, immediately jump between higher and lower menu levels.

In the illustrated embodiment, the viewing regions 68 and 70 are vertically separated by a graphical line or line of characters 72, with the status region 68 occupying the upper one-third of the screen 60 and the working region 70 occupying the lower two-thirds of the screen 60. It should be appreciated, however, that the viewing regions 68 and 70 could be separated horizontally in a side by side relationship, and occupy differing proportions of the screen 60.

The status region 68 and the working region 70 display information in fields. The Format_Display# for the particular display that the interface manager 66 generates is composed of a list of such fields specifying, for each field, its location, size, and type in the region and the format of information it contains.

As will be discussed in greater detail later, the fields can formatted as individual touch selectable buttons. The fields can also be formatted as an array of touch selectable button fields, which present a field of choices to the operator.

The fields can also be formatted as blocks comprising alpha or numeric data strings, or textual data comprising multiple lines of line-wrapped, scrollable text, or graphic images. The fields can also be formatted to be bar graph fields, which display numeric format in graphical form.

The interface manager 66 includes constant (ROM-based) structures in look-up table form that store data describing the layout and formatting of all display attributes, including regions, field type, and field location within the regions. The interface manager 66 stores dynamic (RAM-based) structures that describe the present state of the interface display. Upon receiving a given Create_Display# command from the activated application, the interface manager 66 examines the ROM-based table structures and the RAM-based status structures to create or update the RAM-based status structures, as called for by the activated application. The interface manager 66 includes a time-triggered task routine that performs all operations required to periodically update screen 60 and audio outputs. The interface manager 66 sends this processed information to the interface controller 64 for implementation.

The interface manager 66 also holds a Function#_Code associated with each touch selectable button field identified by the Touch#_Code received from the interface controller 64. The Function#_Codes are arranged in constant (ROM-based) look-up table form according to region and field location within the region, as identified by the Touch#_Code. The interface controller 64 registers the region and field location when a given button is touched, passing this information in the form of a Touch#_Code to the interface manager 66. The interface manager 66 includes a process button utility that awaits and asynchronously processes this information by examining the ROM-based table structure and sending the appropriate Function#_Code to the application control manager 46 for implementation.

Figure 4:
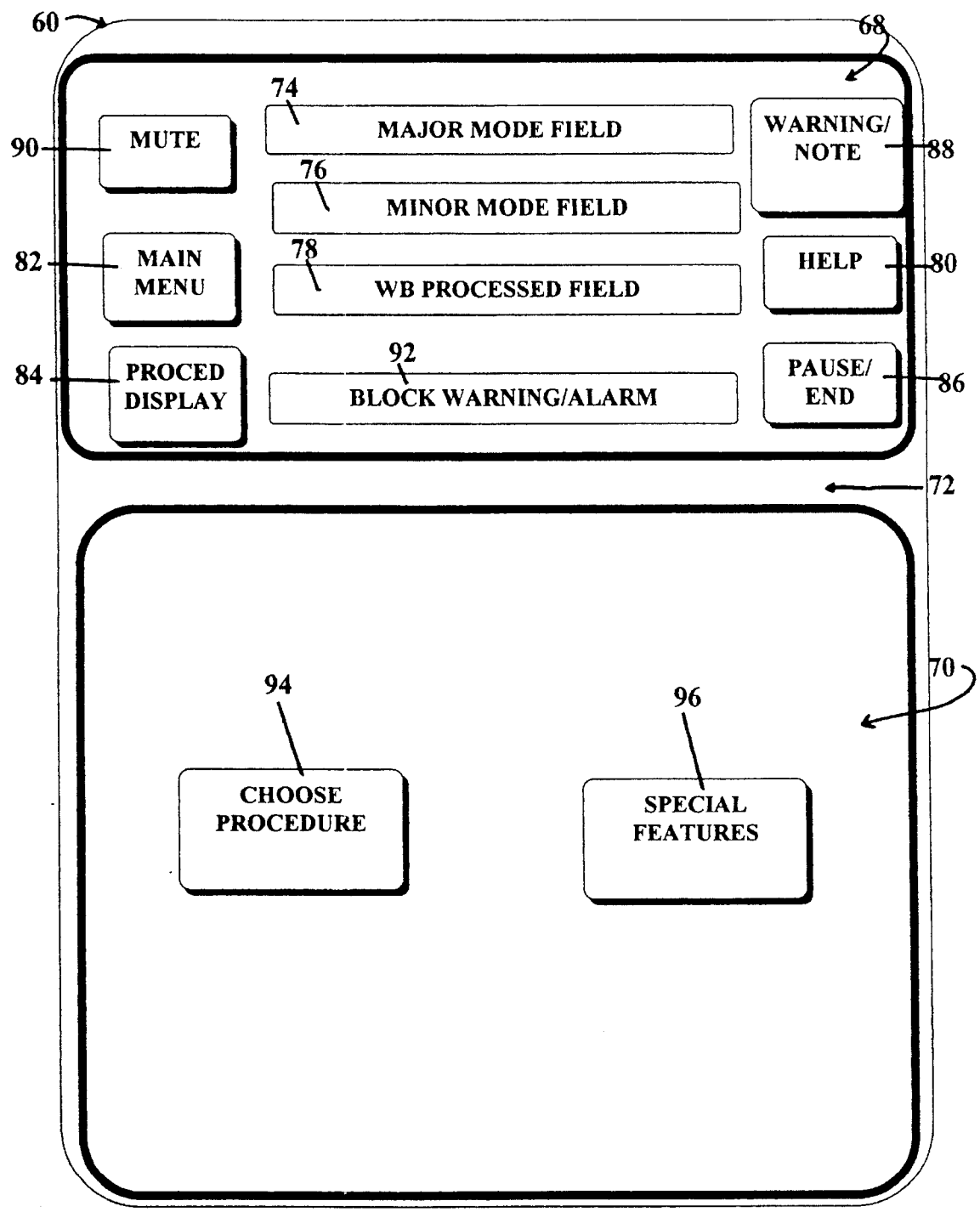
FIG. 4 is a view of the dual region interface that embodies the features of the invention, showing the block and touch activated fields that the interface contains.

The information and format selected for display in the status region 68 and the working region 70 can vary. FIG. 4 shows a preferred implementation.

1. The Status Region

In the illustrated and preferred implementation, the status region 68 includes a three blocks fields 74/76/78 that provide general status information about the procedure then being run.

The MAJOR MODE field 74 contains the description of the clinical procedure activated. For example, the procedure is "Dual Needle Platelet Collection," or any other application selected by the user and resident in the application control manager 46.

The MINOR MODE field 76 contains a one or two word description of the procedure status. For example, for a Dual Needle Platelet Collection, the MINOR MODE field 76 can sequentially display an install mode (for installing disposable elements on the hardware elements); a system check mode (for checking hardware operation before beginning processing); a prime mode (for removing air from the system before processing); a collection mode (for collecting whole blood for processing); a flush and reinfusion mode (for removing residual components from the system for return to the donor after processing); and a so-called wrapup mode (for removing disposable elements from the hardware elements after processing).

The WB PROCESSED field 78 contains the amount of blood drawn from the donor through the draw pump P2 during processing, expressed numerically in units of ml. The WB PROCESSED field 78 is displayed when the dual needle procedure enters the collection mode and remains displayed until the procedure has ended or is terminated.

In the illustrated and preferred embodiment, the status region 68 also includes an array of touch selectable button fields 80/82/84/86. As before described, the individual button fields 80/82/84/86, when touched, each cause the interface manager 66 to transmit a prescribed function code for implementation by the application control manager 46. The touch selection of a given button field does not alter the display of information in the blocks fields 74/76/78 on the status region 68. Any change in the interface 58 resulting from touch selection of a given button in the status region 68 typically occurs in the working region 70.

When touched, the HELP button field 80 calls up a context-sensitive function that displays in the working region 70 general, largely qualitative information regarding the procedure status displayed in the MINOR MODE field 76.

When touched, the MENU button field 82 calls up a function that causes activation of the main menu application and the resulting display of the Main Menu in the working region 70 (as FIG. 4 shows as a default condition). As will be described in greater detail later, the Main Menu allows the operator to select for activation any application A1–A3 managed by the application control manager 46. When touched, the PROCEDURE DISPLAY button 84 field calls up a function that displays in the working region 70 the display of specific procedure-dependent information then called for the activated procedure application.

The MENU button field 82 and the PROCEDURE DISPLAY button field 84 in the status region 68 together make possible the rapid selection of other non-clinical procedure applications while a given clinical procedure application runs, while retaining the ability to immediately return to the particular display of specific procedure-dependent information then called for by the activated clinical procedure, without the need to progress up and down through a menu tree structure or to find one's place in a sequence of menus that are intended to lead the operator stepwise through the procedure from start to finish.

When touched, the PAUSE/END button field 86 calls up a function that immediately pauses any currently operating clinical procedure application. At the same time, the button calls for the display in the working region 70 of the display of specific procedure-dependent information called for by the activated procedure at the time that the PAUSE/END button 86 is activated. At this time, the working region 70 display also preferable includes a RESUME touch activated button field or an END touch activated button field, to give the operator the choice of continuing with the procedure or halting it.

In the illustrated implementation, the block fields 74/76/78 occupy fixed locations in the center of the status region 68. The MENU button field 82 and the PROCEDURE DISPLAY button field 84 occupy fixed locations on the left side, middle and bottom positions, of the status region 68, respectively. The HELP button field 80 occupies a fixed location on the right side, middle position, of the status region 68. The PAUSE/END button field 86 occupies a fixed location on the right side, bottom position, of the status region 68.

The status region 68 also includes context-dependent NOTE/WARNING PROMPT button field 88 that occupies a fixed location on the right side, top position, of the status region 68 when an alarm or warning is active. The NOTE/WARNING PROMPT button field 88 is not displayed when an alarm or warning is not active. A MUTE button field 90 also occupies a fixed location on the left side, top position, of the status region 68 when an alarm is active. A WARNING/ALARM block field also occupies a fixed location on the center, bottom position, of the status region when an alarm is active. Further details of the alarms and the NOTE/WARNING PROMPT and MUTE buttons 88 and 90 and the WARNING ALARM block filed 92 will be described later.

2. The Working Region

In the illustrated and preferred embodiment, the working region 70 shows by default the Main Menu display called for by the main menu application A3. The Main Menu display includes an array of touch selectable button fields 94 and 96, labeled CHOOSE PROCEDURE and SPECIAL FEATURES.

When touched, the CHOOSE PROCEDURE button field 94 calls up a function that displays a Procedure Submenu in the working region 70. The Procedure Submenu lists in an array of touch selectable button fields all clinical procedure applications administered by the application control manager 46, which in the illustrated implementation is the Dual Needle Procedure Application A1. When touched, a procedure application button field calls up a function that directs the application control manager 46 to activate the associated application. The activated application generates its own designated Create_Display# commands, which the interface manager 66 implements to change the display in the working region 70. Further details of this will be provided later.

When touched, the SPECIAL FEATURES button field 96 calls up a function that displays a Special Features Submenu in the working region 70. The Features Submenu lists in an array of touch selectable button fields designed non-clinical procedure specific applications administered by the application control manager 46, which in the illustrated implementation is the Configure System Procedure Application A2. When a given special procedures application button is touched, that application is activated and the display in the working region 70 changes in response to the Create_Display# commands of the activated application. Further details of this will be provided later.

According to the protocol established by the interface manager 66 in the preferred implementation, only one display is active at any given time in the status and working regions 68 and 70. The operator can make input selections using the active display, and the interface manager 66 up dates and refreshes the active display with real time information received from the activated application.

Conceptually, working displays on each region 68 and 70 lie on top of each other, with the most recent "active" display lying on top, the first preceding active display laying inactive beneath it, and so on. If the active display is deleted or closed by the activated application, or by one of the functions called by a touch activated button field, without a new Create-Display# command, the interface manager 66 makes the first preceding display visible and active. A display called for by a create display command is placed on top and made active until terminated, closed, or replaced by a successive create display command.

Preferably, the interface manager 66 includes additional RAM-based memory to preformat frequently used displays before displaying them. Such "virtual displays" remain inactive until called for an activated application or by a callable function.

In the illustrated and preferred embodiment, the interface manager 66 also supports a full screen 60 mode (see FIG. 5), which can be enabled or disabled by any particular application. In the full screen 60 mode, the interface screen 60 includes a single textual or graphical block field 98 forming single display region. The full screen mode can be used, for example, during system start-up, initialization, and some; diagnostic modes.

The following example illustrates the operation of the dual region interface.

Example

Figure 8:
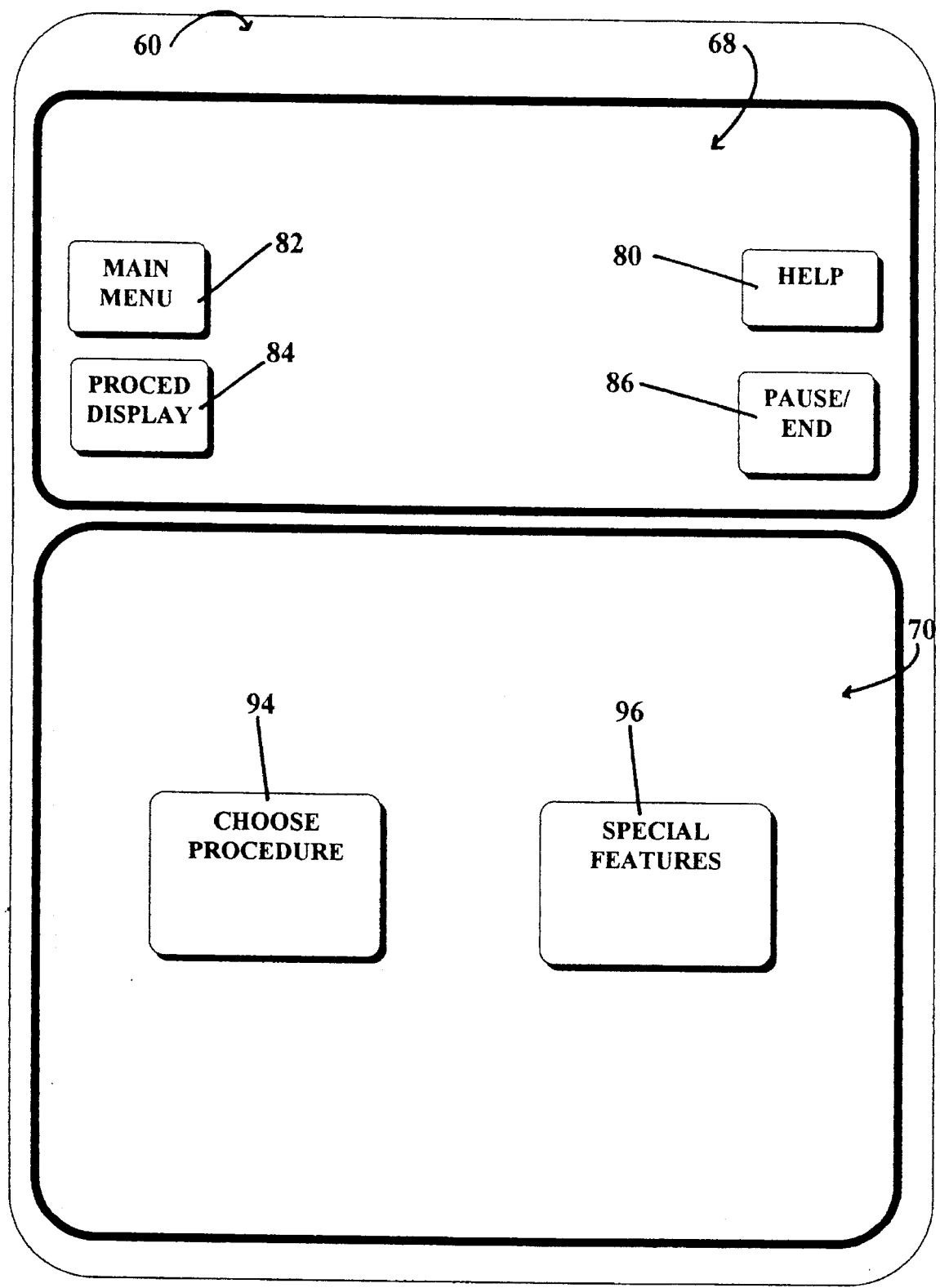
FIG. 8 is a view of the dual region interface in a system start-up default condition, showing the Main Menu in the working region of the interface screen.

FIG. 8 shows the default condition of the dual region interface screen 60 that embodies the features of the invention, as it exists before the selection of a procedure application. The status region 68 is thus free of the MAJOR MODE, MINOR MODE, WB PROCESSED, and BLOCK WARNING/ALARM fields 74/76/78/92 (see FIG. 4 for comparison). In addition, the MUTE and WARNING/NOTE button fields 88 and 90 (also see FIG. 4 for comparison) are also empty. The working region 70 shows the Main Menu, showing a CHOOSE PROCEDURE button field 94 and a SPECIAL FEATURES button field 96 already described.

Figure 9:
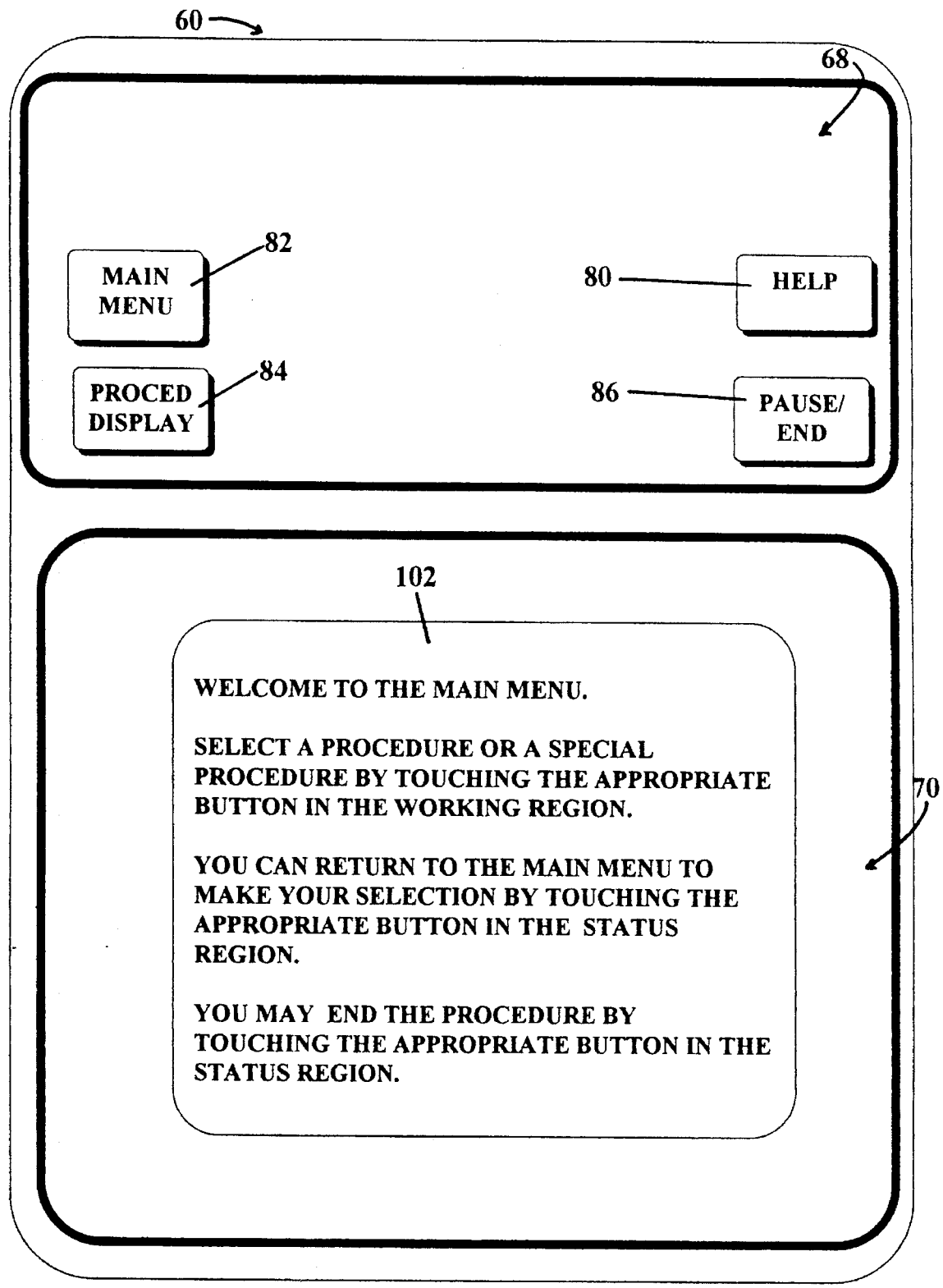
FIG. 9 is a view of the condition of the interface screen with the HELP button activated in the status region when the Main Menu is active in the working region of the screen.

FIG. 9 shows the condition of the dual region interface screen 60, after the operator has selected the HELP button field 80 in the status region 68. The status region 68 shows no change. However, a textual field 102 has been opened in the working region 70, overlying and hiding the Main Menu. The textual field 102 provides general information about the Main Menu and the selection options available in the Main Menu and in the status region 68. By touch selecting the MAIN MENU button 82 in the status region 68, the operator immediately returns to the Main Menu in the working region 70, as FIG. 8 shows.

Figure 10:
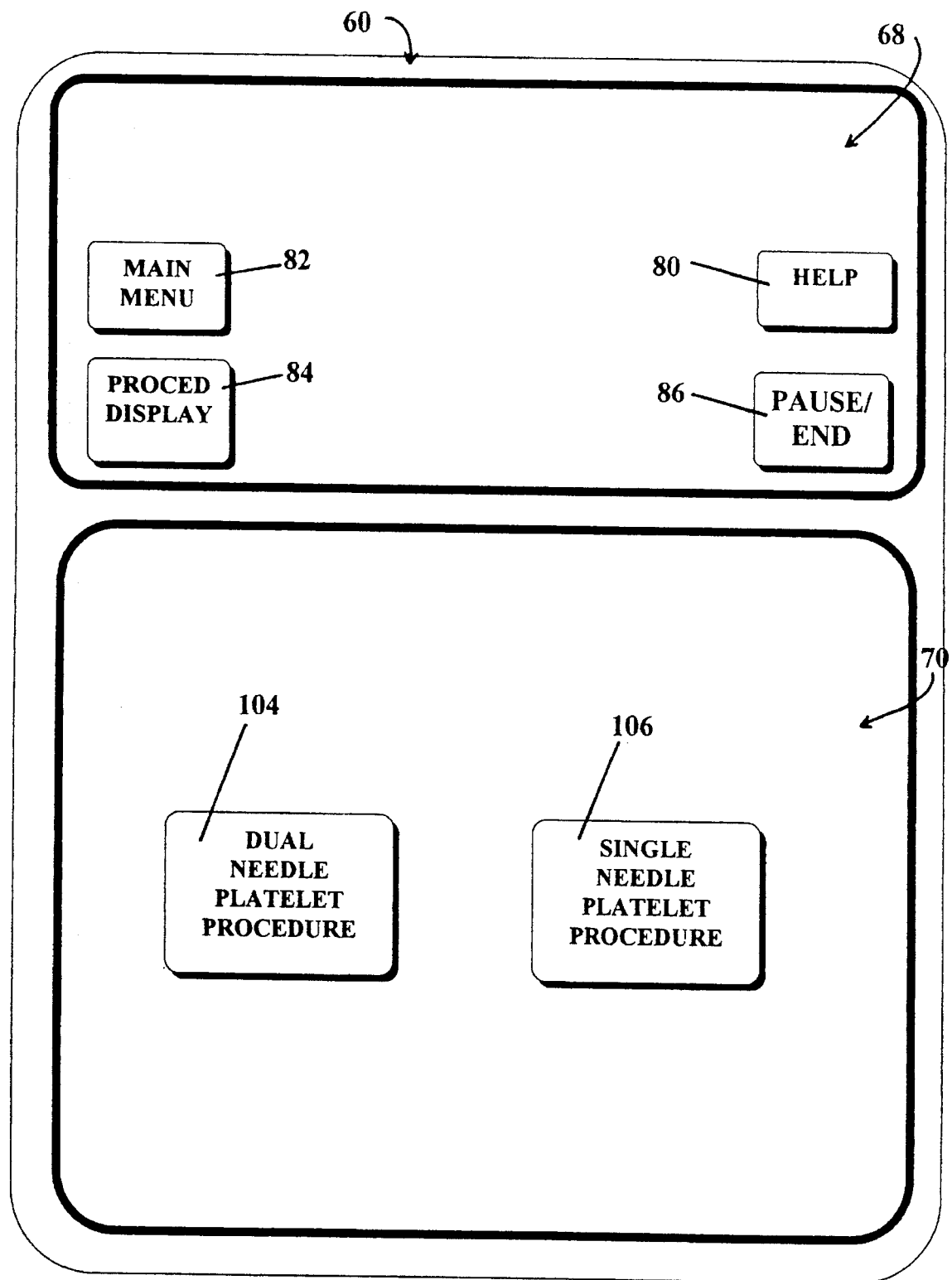
FIG. 10 is a view of the dual region interface, showing the Select Procedures SubMenu in the working region of the interface screen.

FIG. 10 shows the condition of the dual region interface screen 60, after the operator has selected the CHOOSE PROCEDURE button field 94 in the working region 70. The status region 68 shows no change. The working region 70 shows in button fields 104 and 106 the clinical procedure applications resident in the application control manager 46. In the illustrated embodiment, a button field 104 labeled the Dual Needle Platelet Procedure is shown for activating the application A1. Additional button fields would also exist (for example, a Single Needle Platelet Procedure button field 106, as shown) equal in number to the number of procedure applications residing in the application control manager 46.

Figure 11:
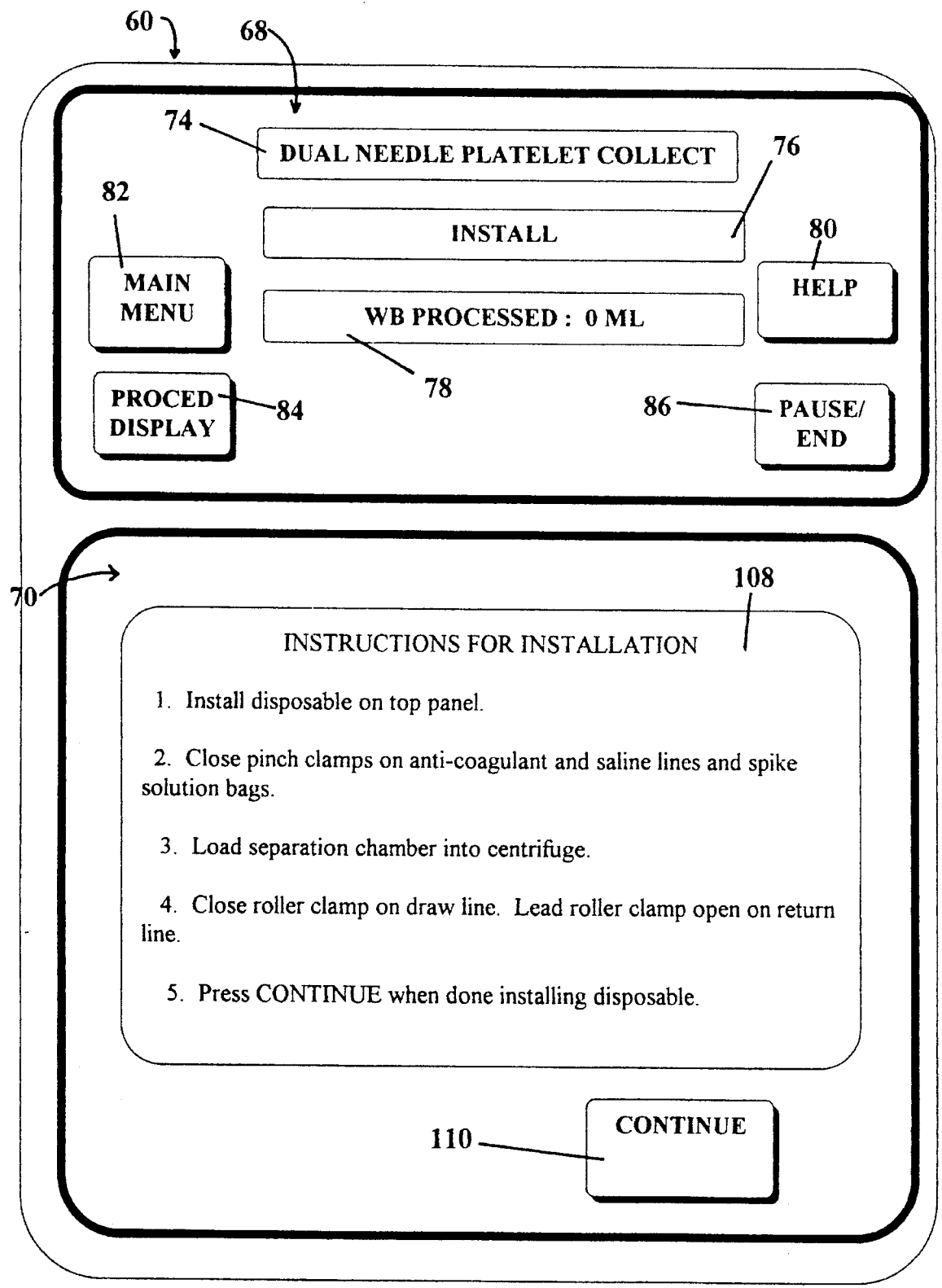
FIG. 11 is a view of the dual region interface, showing the installation instructions for the install mode in the working region of the interface screen.

FIG. 11 shows the condition of the dual region interface screen 60, after the operator has selected the Dual Needle Platelet button field 104 in the working region 70. The status region 68 shows in the MAJOR MODE field 74 that the Dual Needle Platelet Collection Procedure has been selected. The Status region 68 also shows in the MINOR MODE field 76 that the procedure is in the install mode. The status region shows in the WB PROCESSED FIELD 78 that no whole blood has been collected yet. The working region 70 shows in the textual field 108 instructions for the operator to follow in installing the disposable elements on the hardware elements. The working region 70 also shows a touch activated CONTINUE button field 110 which, when touched, causes the instructions in the textual field 108 to progress, taking the operator stepwise through the installation procedure until complete.

The MINOR MODE field 76 in the status region 68 changes as the activated procedure progresses through successive modes including a check of hardware functionality, priming of the fluid flow paths to remove air, procedure start-up, and venipuncture tasks, either automatically or with the assistance of the operator. The textual field 108 in the working region 70 also changes to display information, as appropriate, to prompt the operator to take steps to aid in accomplishing these tasks. In all other respects, the other visual aspects of the status region 68 and working region 70 remain unchanged.

Figure 12:
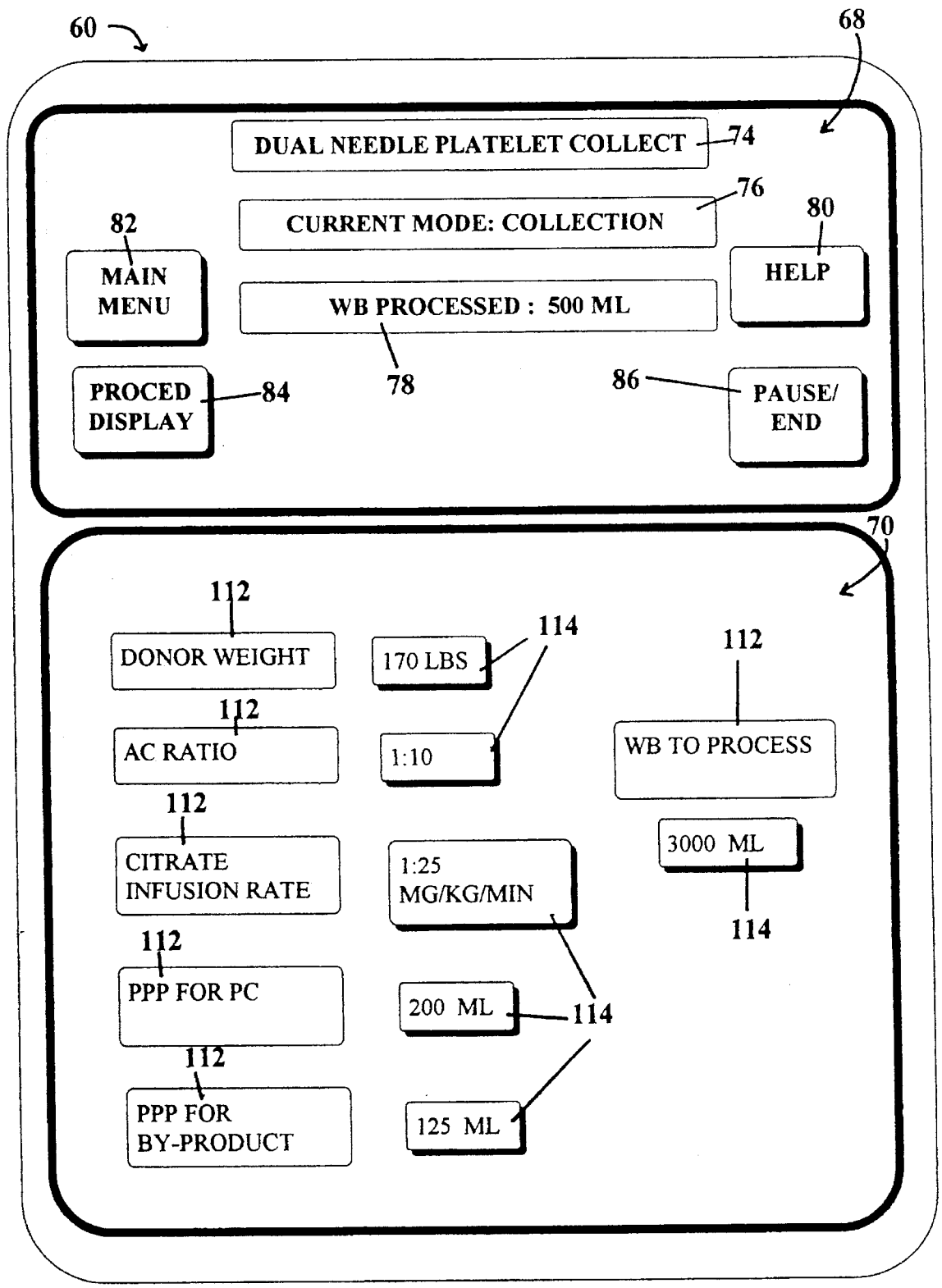
FIG. 12 is a view of the dual region interface, showing the detailed procedures display for the collection mode in the working region of the interface screen.

FIG. 12 shows the condition of the dual region interface screen 60, when the procedure enters the collection mode. During the collection mode, whole blood is drawn from the donor, centrifugally separated into component parts, and its components either returned to the donor or collected, as earlier described.

The Status region 68 continuously shows in the MINOR MODE field 76 that the procedure is in the collection mode. The status region continuously shows in the WB PROCESSED FIELD 78 the volume of WB drawn from the donor. The location and attributes of the other button fields 80/82/84/86 remain unchanged, unless the procedure changes operational mode, at which time the MINOR MODE field 76 will change to reflect this mode change.

The working region 70 continuously shows in an array of prescribed textual block fields 112 and associated prescribed touch activated button fields 114 selected field values detailing the progress of the ongoing procedure.

The type of information selected by the procedure application for display as a field value in the working region 70 during the collection mode can vary. In the illustrated embodiment, the block fields 112 list by way of example the donor weight, the anticoagulant (AC) ratio, the rate of infusing citrate carried by the PPP returned to the donor, the volume of PPP collected for resuspending collected PC, the amount of additional PPP collected as a by-product, and the amount of whole blood yet to be processed to meet the PC yield selected for the procedure. The associated button fields 114 contain the current status of these operational factors, which are displayed as field values within the button fields 114.

Field values in the button field 114 change to reflect changes in the current status, when they occur. For example, the amount of WB to be processed decrements over time toward zero. When the WB to process button field 114 is zero, the application prompts the operator to begin the flush and reinfusion mode.

Figure 13:
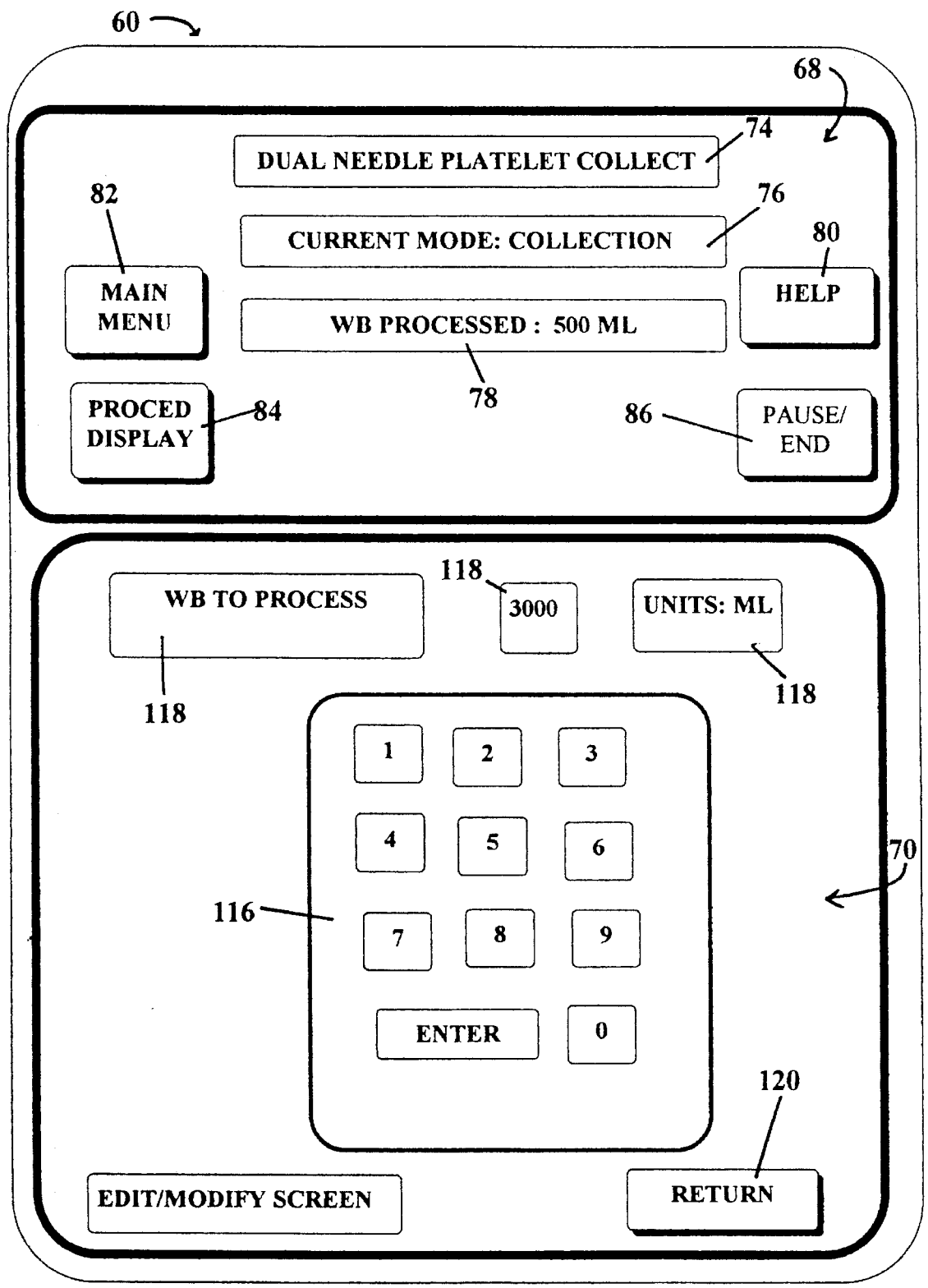
FIG. 13 is a view of the dual region interface, showing the edit/modify screen for the detailed procedures display in the working region of the interface screen during the collection mode.

In the illustrated and preferred embodiment, the operator can, by touch selecting a given button field 114, modify the displayed field value. FIG. 13 shows the condition of the display screen 60 when, for example, the operator touch selects the WB TO PROCESS button field 114 in the working region 70 to change the volume of whole blood to be processed during the procedure. The working region 70 display changes to display a touch activated numeric keypad 116, along with block fields 118 showing the field value to be changed, it present value, and the units in which it is expressed. By touch activating the keypad 116, the operator changes and enters the new value, then selects the touch activated Return button field 120 to return to the working display 70 shown in FIG. 12. The field value in the WB TO PROCESS button field 114 will reflect the new field value.

As FIG. 13 shows, as the working region 70 display changes to accommodate the edit/modify procedure just described, the status region 68 display remains visible and unchanged, except to reflect changes in the volume of whole blood processed during the edit/modify procedure or any change in operational mode called for by the activated application.

Figure 14:
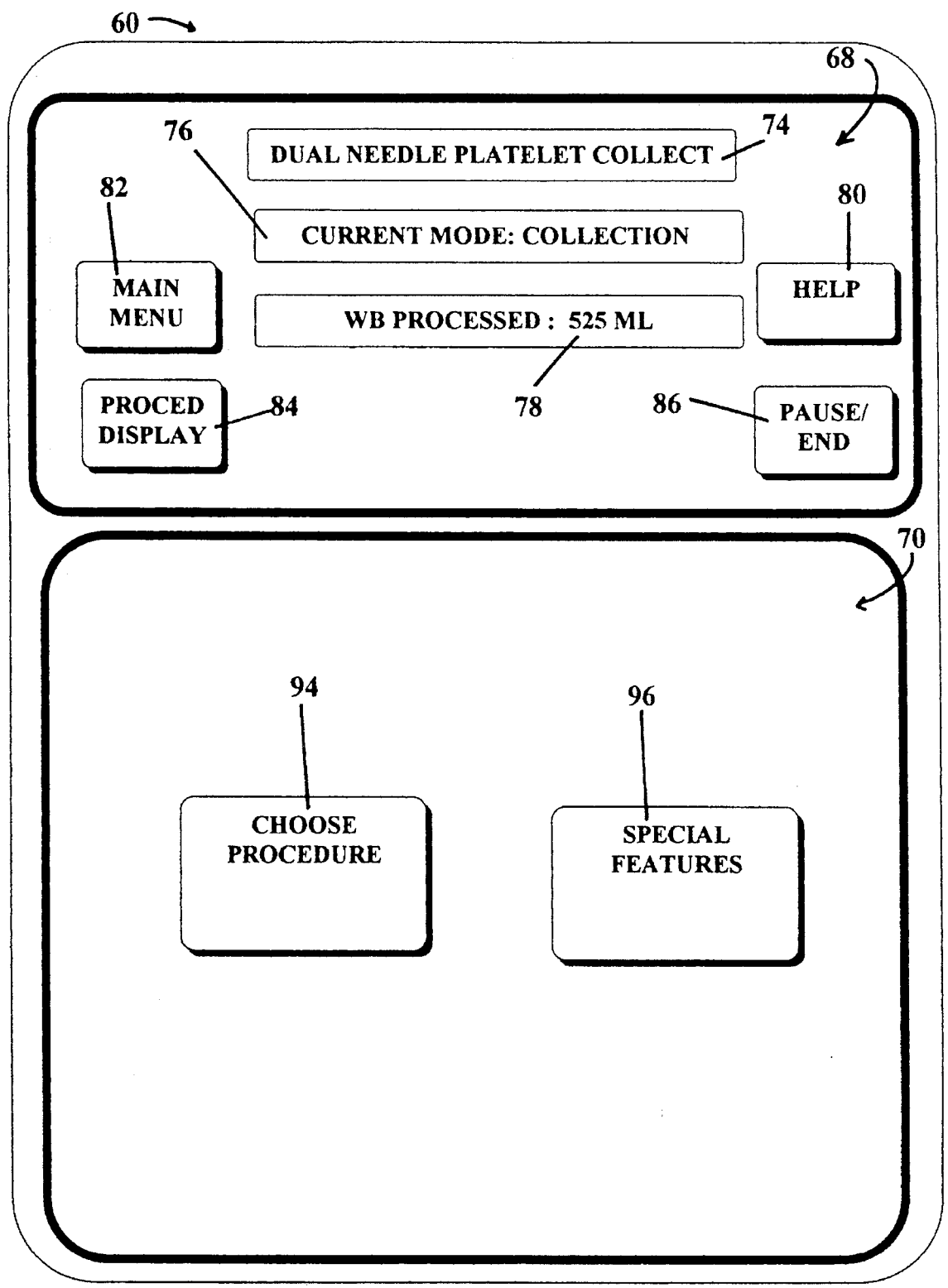
FIG. 14 is a view of the dual region interface, showing the Main Menu in the working region of the interface screen during the collection mode.

At any time the operator may choose to return to the main menu by touch selecting the MENU button field 82 in the status region 68. FIG. 14 shows the condition of the display screen 60 should the operator make this choice after having completed the exit/modify procedure just described.

As FIG. 14 shows, the working region 70 of the screen changes to show the Main Menu. The status region 68 display remains visible and unchanged, reflecting the status information at the time the MENU button field 82 was activated by the operator, except to reflect ongoing changes in the volume of blood processed (as a comparison of FIG. 14 to FIG. 12 shows) or a change in operational mode.

Figure 15:
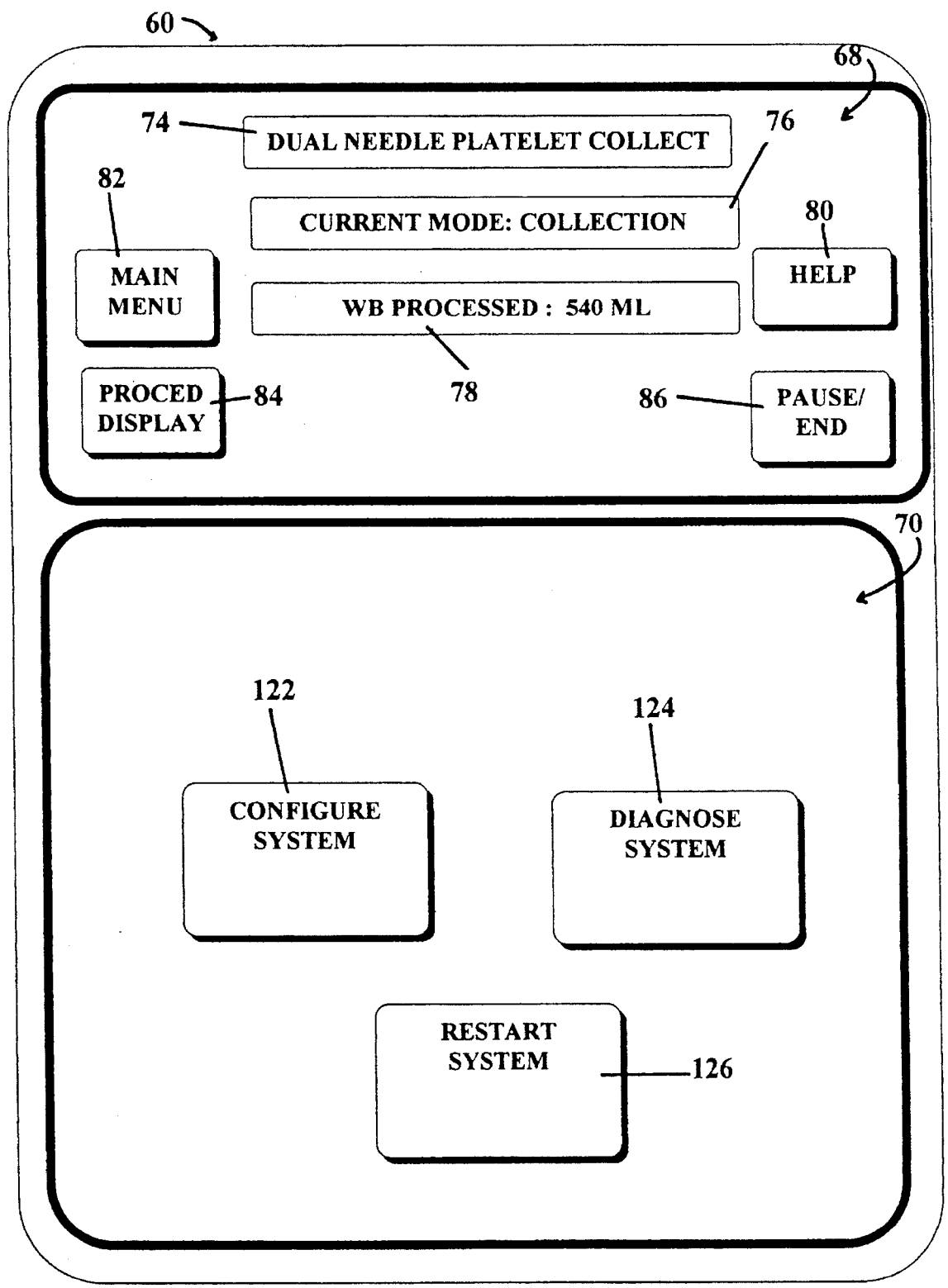
FIG. 15 is a view of the dual region interface, showing the Special Features SubMenu in the working region of the interface screen during the collection mode.

The operator can next proceed to touch select the Special Features button field 96, if desired. FIG. 15 shows the condition of the display screen when this selected is made. As FIG. 15 shows, the working region 70 of the screen 68 changes to show the Features Submenu. The Features Submenu lists in an array of touch selectable button fields 122, 124, and 126 the non-procedure specific applications administered by the application control manager 46. Touch button field 122 activates the Configure System Procedure Application A2. By way of further example, FIG. 15 assumes that additional non-clinical procedural applications are also resident in the application control manager 46, such as the diagnosis application (which touch button field 124 activates) and system restart application (which touch button field 126 activates), as previously discussed.

As FIG. 15 shows, the status region 68 display remains visible and unchanged as the working region 70 display changes to show the Features Submenu. The status region 68 continues to reflect the status information at the time the SPECIAL FEATURES button field 96 was activated by the operator, except to reflect ongoing changes in the volume of blood processed (as a comparison of FIG. 15 to FIG. 14 shows) or changes in the operational mode.

The operator may proceed to touch select a given button field 122, 124, 126 in the working region 70 shown in FIG. 15. The selected button field will activate the associated application. Meanwhile, the status region 68 remains visible and unchanged, except to reflect status changes in the information fields it contains.

At any time, and regardless of the active display presently in the working region 70, the operator may choose to again view detailed status information about the clinical procedure then being implemented (as shown in the MINOR MODE field 76). To do so, the operator need only to touch select the PROCEDURE DISPLAY field button 84, which remains continuously visible and accessible at all times to the operator in the status region 68. The working region 70 display returns to the format and attributes shown in FIG. 12 (if the process is still in the collection mode), or whatever the format or attributes of the procedure display is for the mode identified in the MINOR MODE field 76.

In this way, the status region 68 keeps the operator continuously informed as to the "big picture" as the working region 70 changes to provide access to the details of processing. The status region 68 also provides the means for the operator to quickly jump through the multiple-level menu structure of the interface 58, to attend to details on one menu level, without necessarily moving stepwise up and down the menu structure and without losing the ability to, on command, immediately jump between higher and lower menu levels.

The MINOR MODE field 76 changes to reflect mode changes made under the control of the activated application. After collection ends (i.e., when the designated WB TO PROCESS field value shown in FIG. 12 decrements to zero), the procedure prompts the operator to enter the RBC flush and reinfusion mode, during which residual RBC are flushed and returned to the donor. The procedure then enters a Procedure Wrap Up mode, in which the operator is instructed to remove the disposable components.

C. Abnormal Operational Conditions

(i) Detection

Each procedure application (see FIG. 6) defines abnormal functional and operational states that require operator awareness and/or operator intervention. The procedure application A1 processes status data received from the instrument manager 50 to determine whether any; current operating condition constitutes a prescribed abnormal functional state. If so, the application control manager 46 issues prescribed commands to notify the operator through the user interface 58 and, under certain conditions, suspend system operation.

As earlier described, the MPU 44 also includes the condition manager 56 to provide fail-safe support to error detection functions of the application control manager 46. It should be appreciated that, alternatively, the condition manager 56 can reside in an auxiliary processing unit (APU) (for example, a second type 68030 microprocessor), or partly in the MPU 44 and partly in an APU.

The condition manager 56 contains a list defining abnormal functional and operational states. Some of the defined states in the condition manager 56 are the same as the states defined in the application control manager 46, while others are independent cross checks of hardware control commands and status data to verify hardware integrity that only the condition manager 56 undertakes.

The condition manager 56 monitors the flow of data between the instrument manager 50 and the peripheral hardware controllers 54 (shown in FIG. 2) to determine whether any current operating condition meets the criteria defined for an abnormal functional state. Where possible, the condition manager 56 preferably includes a time-out period for conditions that the application control manager 46 also monitors, to thereby allow the application control manager 46 a period of time to correct the abnormal state.

Figure 6:
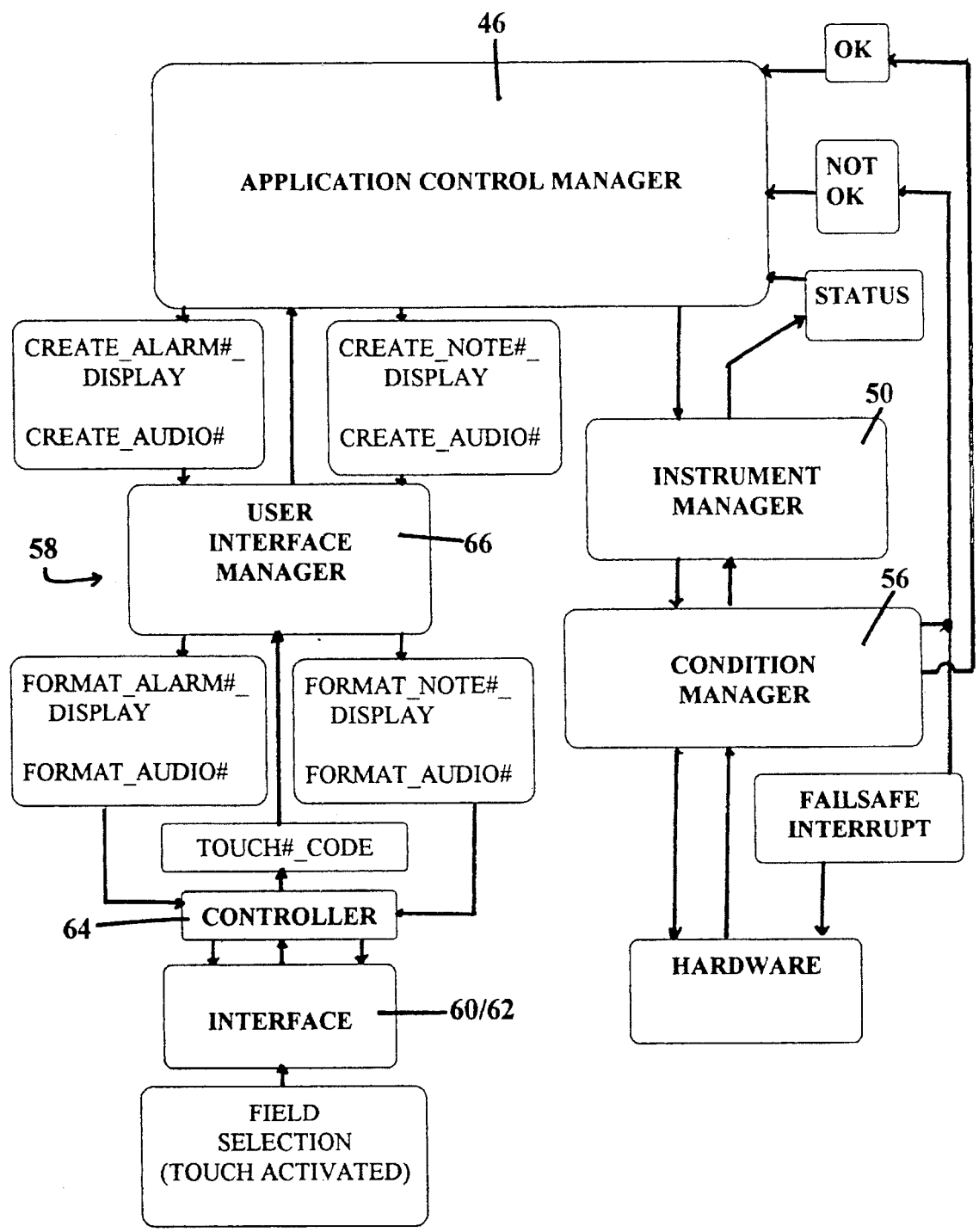
FIG. 6 is a diagrammatic view of the detection and display of abnormal function conditions by the controller shown in FIGS. 2 and 3.

As FIG. 6 shows, the condition manager 56 continuously sends an OK_State status to the application control manager 46 as long as no current operating condition constitutes a defined abnormal functional state, or as long as the time-out period for a sensed abnormal functional state, if applicable, has not lapsed.

When the condition manager 56 detects a current operating condition that meets the criteria defined for an abnormal functional state, and if the time-out period, if applicable, has lapsed, the condition manager 56 sends a Not_OK_State# status to the application control manager 46. The Not_OK_State# status identifies to the application control manager 46 the abnormal condition detected. Upon receipt of the Not_OK_State# status from the condition manager 56, and regardless whether the activated procedure application also detects the same abnormal functional state, the application control manager 46 issues prescribed commands to notify the operator through the user interface 58.

Upon issuing a Not_OK_State# status, the control manager 56 goes fail-safe, suspending system operation and interrupting all further communication between the application control manager 46 and the peripheral controllers 52 until the abnormal state is corrected.

(ii) Classification

In the preferred embodiment, the application control manager 46 categorizes defined abnormal functional and operational states either as an alarm condition or as an attention condition. The alarm conditions comprise functional and operational states requiring immediate operator intervention. The attention conditions comprise functional and operational conditions that may be transient and self-correcting over time, or that otherwise do not require immediate operator intervention. In the preferred embodiment, the application control manager 46 automatically upgrades an attention condition that remains uncorrected for a prescribed period of time after detection (for example, 2 minutes) to an alarm condition. The application control manager 46 also automatically treats a Not_OK_State# status from the condition manager 56 as an alarm condition.

Examples of abnormal operational states that can be treated as alarm conditions include pump motor direction error; pump motor speed error; liquid spill detected inside the centrifuge; centrifuge rotor imbalance; control voltage power failure; centrifuge door open; centrifuge door not locked; empty anticoagulant container.

Examples of abnormal operational states that can be treated as alarm conditions include temperature in centrifuge above limit; weight scale limits exceeded; and anticoagulant level low.

As FIG. 6 shows, upon detection of a condition that represents an alarm condition, the application control manager 46 generates and transmits a prescribed Create_Alarm#_Display command to the interface manager 66. Likewise, upon detection of condition that represents an attention state, the application control manager 46 generates and transmits a prescribed Create_Note#_Display command to the interface manager 66.

Upon receipt of a prescribed Create_Alarm# or _Note#_Display, the interface manager 66 examines the ROM-based table structures and the RAM-based status structures to create or update the display codes to implement the designation display and audio through the interface controller 64 using the interface screen 60 and audio device 62.

In the illustrated and preferred embodiment, the interface manager 66 places all displays generated in response to Create_Alarm#_Display or Create_Note#_Display commands initially in the status region 68 of the interface screen 60, as FIG. 4 shows. The interface manager 66 reserves the top position on the left and right sides and the bottom center position of the status region 68 for the alarm and note fields 88/90/92. These positions on the status region 68 remain free of any display character or indicia in the absence of a sensed alarm or attention condition.

(i) Warning Alarm Interface

In response to a Create_Alarm#_Display command from the activated procedure application, the interface manager 66 creates the touch selectable, button field 88 (see FIG. 4) on the right side, top position, of the status region 68. In the preferred implementation, in an alarm state, the button field 88 is colored red (the international alarm color) and contains the word "Warning" or some other word or words to denote a sense of urgency.

The interface manager 66 also creates the touch selectable mute button field 90 on the left side, top position, when an alarm state is active. Touch selection of the mute button field 90 turns off a prescribed time period any audible alarm associated with the alarm state.

With the creation of the button field 88, the interface manager 66 creates the alarm block field 92 at the bottom of the status region 68. In an alarm state, the block field 92, also preferably colored red and bar-shaped, contains a description of the warning condition of appropriate length.

Figure 7:
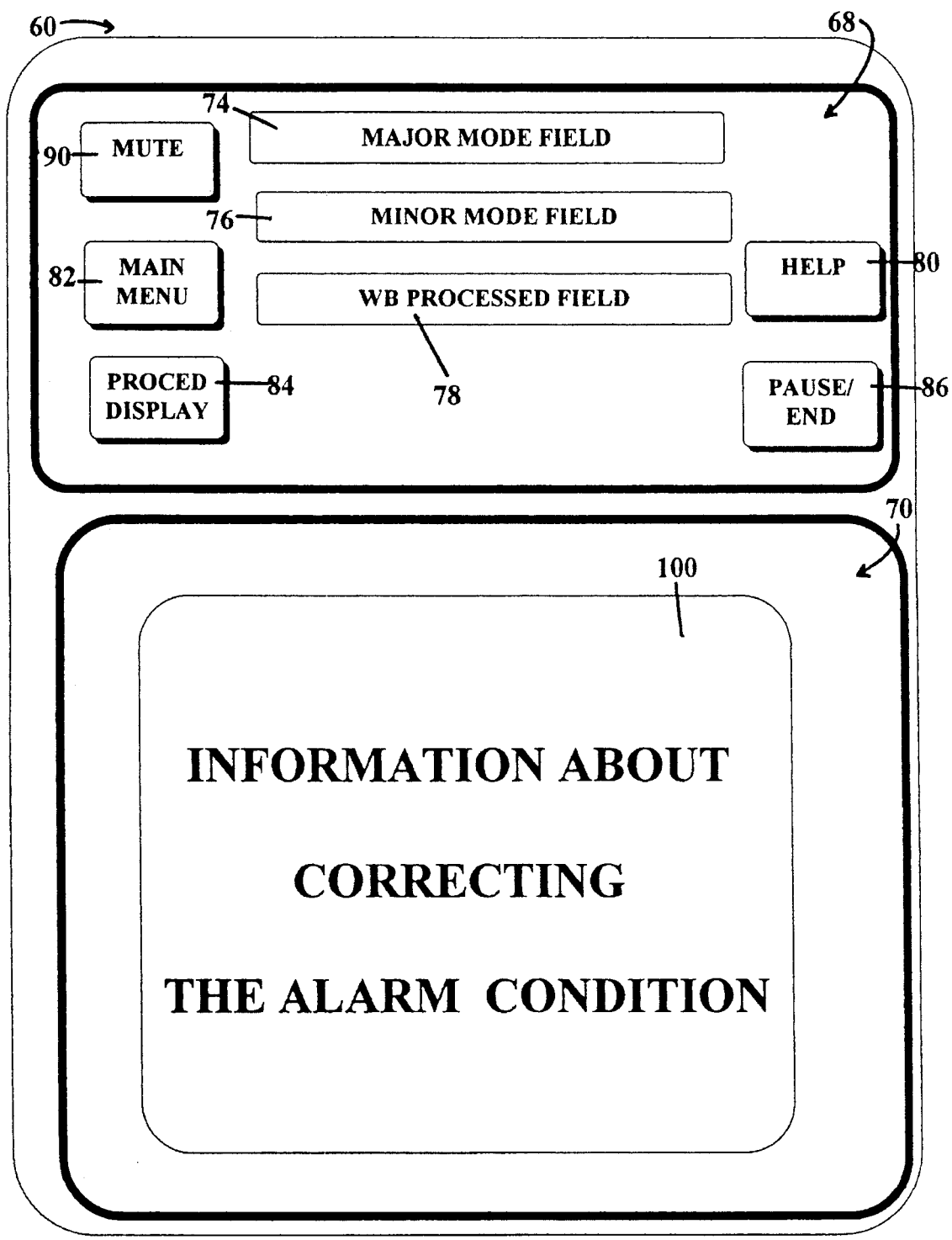
FIG. 7 is a view of the dual region interface in an alarm condition.

When the operator touch selects the warning alarm button field 88 (as FIG. 7 shows), the interface manager 66 removes the button field 88 and the block field 92 from the status region 68 and displays in a textual field 100 in the working region 70 more detailed information regarding the appropriate responses for the operator to follow in correcting the sensed alarm state. Working through the interface manager 66, the alarm state of the activated procedure application maintains control over the working region 70 of the interface, allowing no display except those relating to the alarm state and associated corrective measures to be active, until the condition manager 56 and the application control manager 46 sense the removal of the alarm state.

(ii) Note Alarm Interface

In response to a Create_Note#_Display command from the activated procedure application, the interface manager 66 creates the touch selectable, button field 88 on the right side, top position, of the status region 68 (see FIG. 4). In the preferred implementation, in an attention state, the button field 88 is colored yellow or another cautionary color distinguishable from the color of the button field 88 in an alarm condition. The button field 88 contains the word "Note" or some other cautionary word or words readily distinguishable from the word contained in the field 88; when in an alarm state.

The interface manager 66 also creates the touch selectable mute button field 90 on the left side, top position, when an attention state is active. Touch selection of the mute button field 90 turns off a prescribed time period any audible alarm associated with the attention state.

With the creation of the note alarm button field 88, the interface manager 66 creates the block field 92 at the bottom middle of the status region 68. The block field 92, preferably colored the same color as the note alarm button field and bar-shaped, contains a description of the attention condition of appropriate length.

When the operator touch selects the note alarm button field 88, the interface manager 66 removes the block field from the status region 68 and displays in the textual field 100 (see FIG. 7) in the working region 70 more detailed information and regarding the appropriate responses for the operator to follow in correcting the sensed attention state, if appropriate. Working through the interface manager 66, the attention state of the activated procedure application maintains control over the working region 70 of the interface, allowing no display except those relating to the attention state and associated corrective measures to be active, until the condition manager 56 and the application control manager 46 sense the removal of the attention state.

In the preferred embodiment, the alarm/note fields 88 and 92 relate only to a single alarm or note condition at the same time. There are never multiple displays of these fields at a given time, even when multiple Create_Alarm#_Display and/or Create_Note#_Display commands are received. In this circumstance, the user interface manager 66 stacks the multiple commands in an alarm queue and an attention que as received. The user interface manager 66 and implements the commands for display one at a time, on a first-in, first-out basis, except that an alarm state takes precedence over any attention state. Touch activating the active alarm/note button field 88 to open the associated alarm/note textual field 100 in the working region 70, opens the alarm/warning fields 88 and 92 relating to the next prioritized alarm/attention command in the status region 68. Thus, in the case of multiple pending alarm/attention conditions, as the operator works in the working region 70 to remove one condition, the status region 68 informs the operator of another condition that next requires attention.

The following example illustrates the operation of the interface when an alarm/attention condition is sensed.

Example

Figure 16:
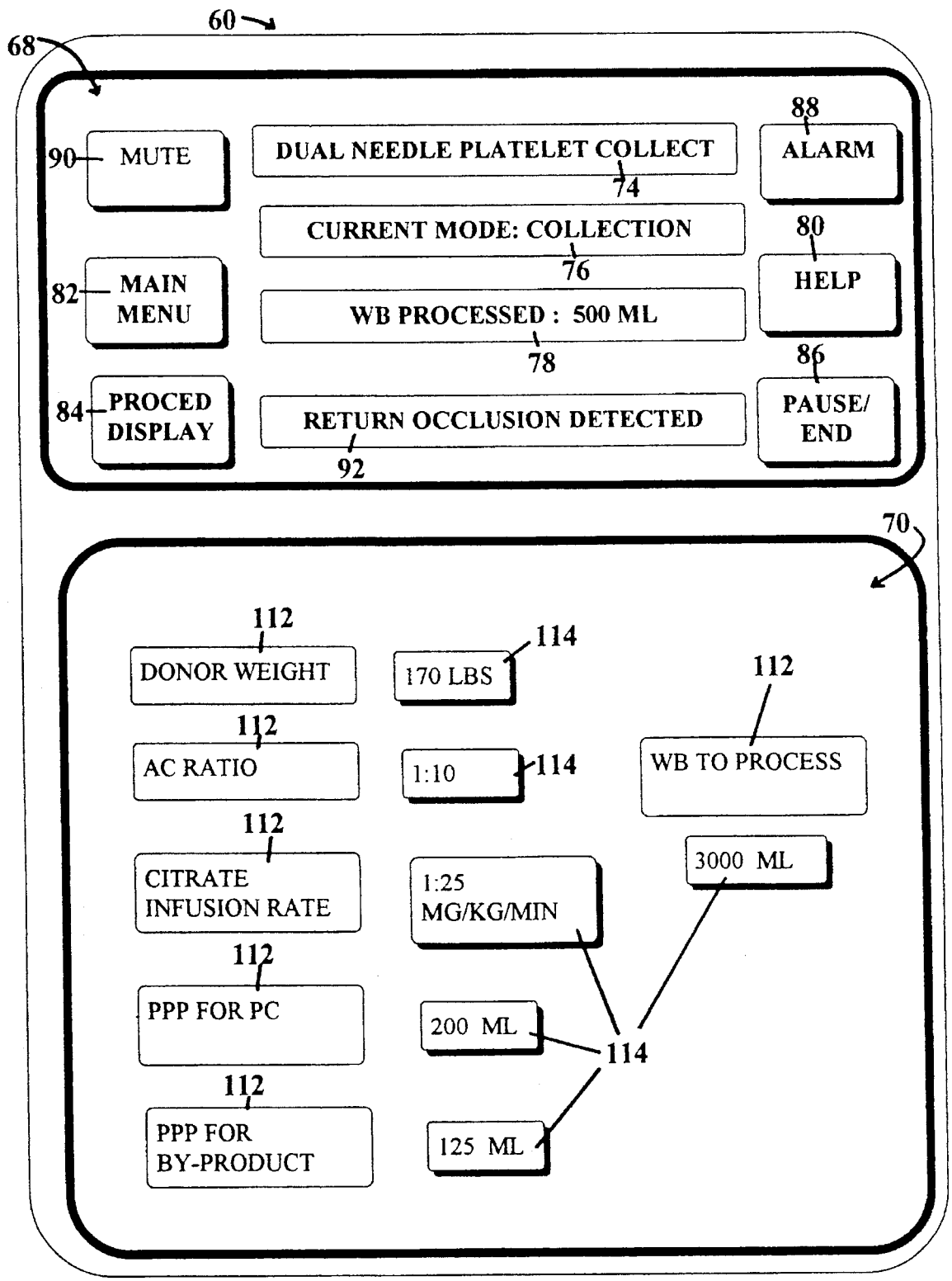
FIG. 16 is a view of the dual region interface, with the detailed procedures display for the collection mode in the working region, and a return occlusion alarm in the status region.

FIG. 16 shows the condition of the interface screen 60 should an occlusion in the tubing branch 40 (see FIG. 1) returning RBC and PPP to the donor be sensed by the application control manager 46 in the manner described above. FIG. 16 assumes that, at the time that occlusion is detected, the screen 60 had a display like that shown in FIG. 12.

As FIG. 16 shows, the display in the status region 68 changes to include the button field 88, which is displayed in red to designate an alarm state (as contrasted with an attention state). The status region 68 also changes to show the block field 92, which is also in red, and which contains text identifying the nature of the alarm (Return Occlusion Detected). The status region 68 also shows the MUTE button field 90, allowing the operator to mute any audible alarm called for by the application control manager 46 for the identified alarm state. The working region 70 continues to show the display that was active at the time the alarm condition was detected.

Figure 17:
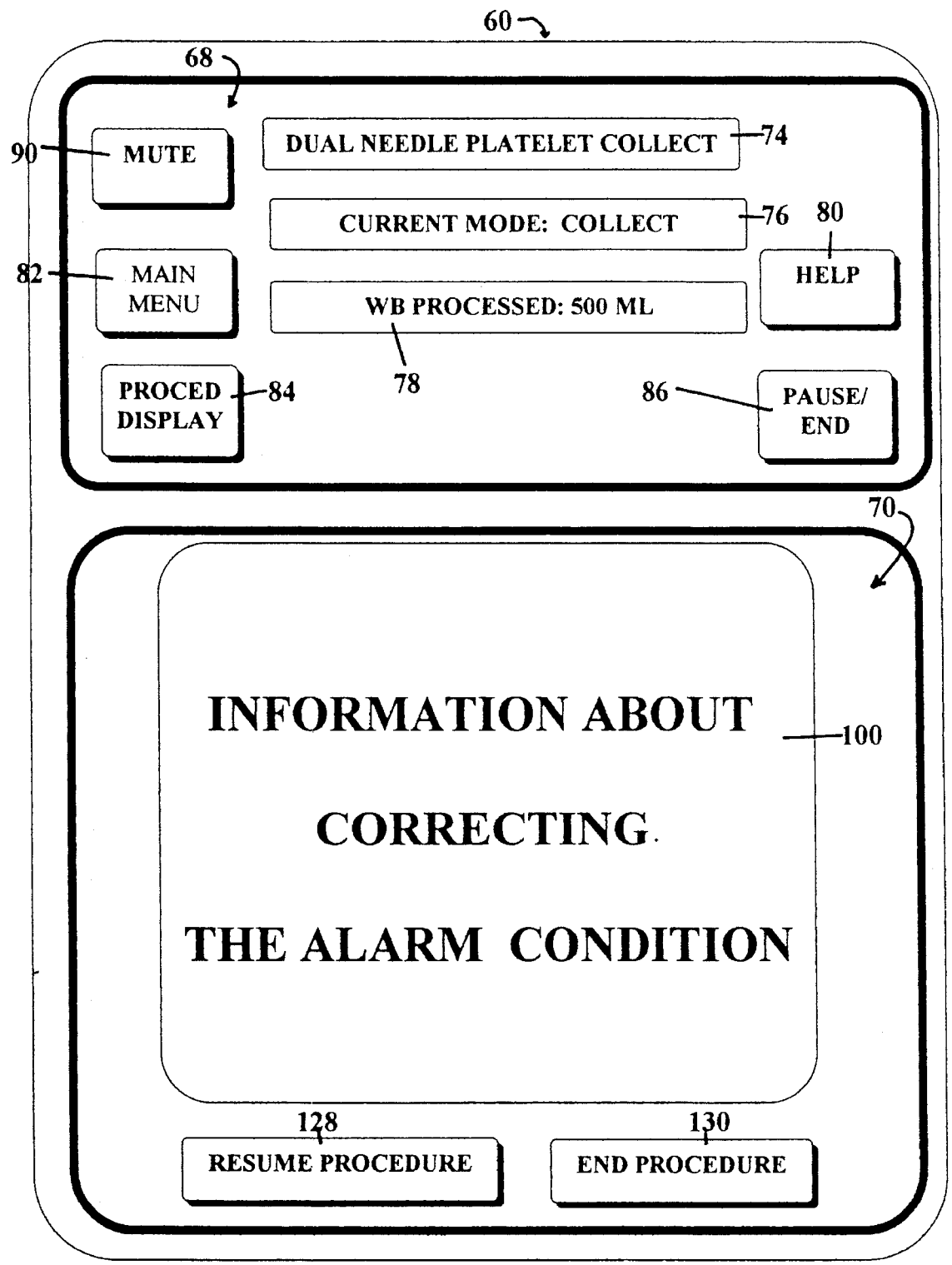
FIG. 17 is a view of the dual region interface, with the instructions for correcting the return occlusion alarm in the working region during the collection mode.

FIG. 17 shows the condition of the screen 70 after the operator touch selects the alarm field button 88. The display in the status region 68 changes by the removal of the alarm button field 88 and associated block field 92. The display in the working region 70 changes to show the text block field 100 (also shown in FIG. 7) containing information about the detected alarm condition and suggested ways of correcting it. The working region 70 also includes touch selected button fields 128 and 130. The button field 128 allows the operator to resume the procedure, once the alarm condition is corrected. The button field 130 gives the operator the option of ending the procedure.

Upon correcting the alarm condition and touch selection of the button field 128, the working region 70 of the display screen 60 returns to the display that was active at the time the alarm condition was first displayed, which in the illustrated embodiment would be FIG. 12.

The specific computer code used for implementing the applications A1-A3, the application control manager 46, the instrument manager 56, condition manager 56, the interface manager 66, and the interface controller 64 depends upon the computer language being used and the preferences of the programmer. The procedures and commands described in this specification can all be written by normally skilled programmers in various conventional langauges, like C; Pascal; PLM; ADA; and multiple tasking BASIC, based upon the descriptions provided herein.

Appendix A includes illustrative functional requirements in a preferred implementation of an interactive user interface that embodies features of the invention.

Various features of the invention are set forth in the following claims.

*Appendix A*

*© Baxter International, Inc. 1994*

6.1.1. Functional Requirement User_Interface_Manager

The User Interface Manager handles all aspects of user-interface output and input. This includes audio (alarms) and physical lights on the UI device. It is capable of managing display information for multiple "applications" using a window-like display format.

Applications provide commands to control windows and display output. Built-in editing features can also be requested. Values which are displayed in window fields are automatically pulled in (via the Window_Data flow) when needed. User input is routed to a message queue associated with the particular display window.

The Communications_Manager is called upon to manage low-level protocol and communications with the Display Controller.

a. Inputs

*Command_from_Display_Msg*
   from: Communications_Manager
*Diagnostic_Command*
   from: Perform_Primary_Functions
*Edit_Info* ::= Value_Object + Edit_Type + Edit_Qid
   from: Perform_Primary_Functions
*Response_from_Display*
   from: Communications_Manager
*Window_Command* ::= [Open_Window_Command | Front_Window_Command | Close_Window_Command | Set_-Window_Mode_Command | Set_Audio_Command | Set_Lights_Command]
   from: Perform_Primary_Functions
*Window_Data* ::= Window_Data_Semaphore + Window_Data_Value_List
   from: Perform_Primary_Functions b. Outputs

*Command_to_Display*
   to: Communications_Manager
*Diagnostic_Data*
   to: Perform_Primary_Functions
*Response_to_Display*
   to: Communications_Manager
*User_Data_Msg* ::= Msg_Type + Window_ID + Value_Object
   to: Perform_Primary_Functions
*User_Function_Msg* ::= [Function_Code_Msg | Keyboard_Code_Msg]
   to: Perform_Primary_Functions
*Window_ID* ::= "int"
   to: Perform_Primary_Functions c. Processing

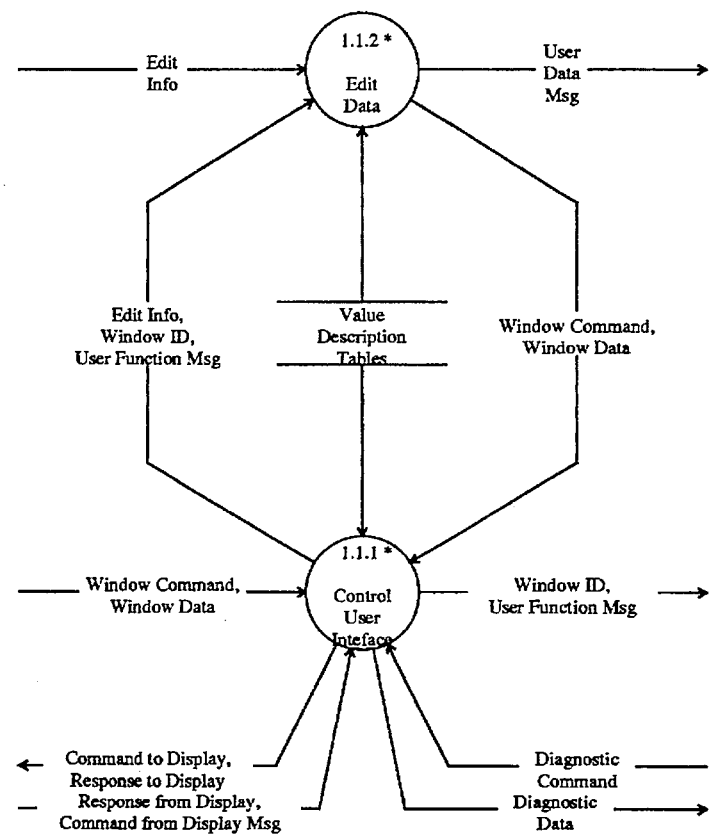

Figure 2:
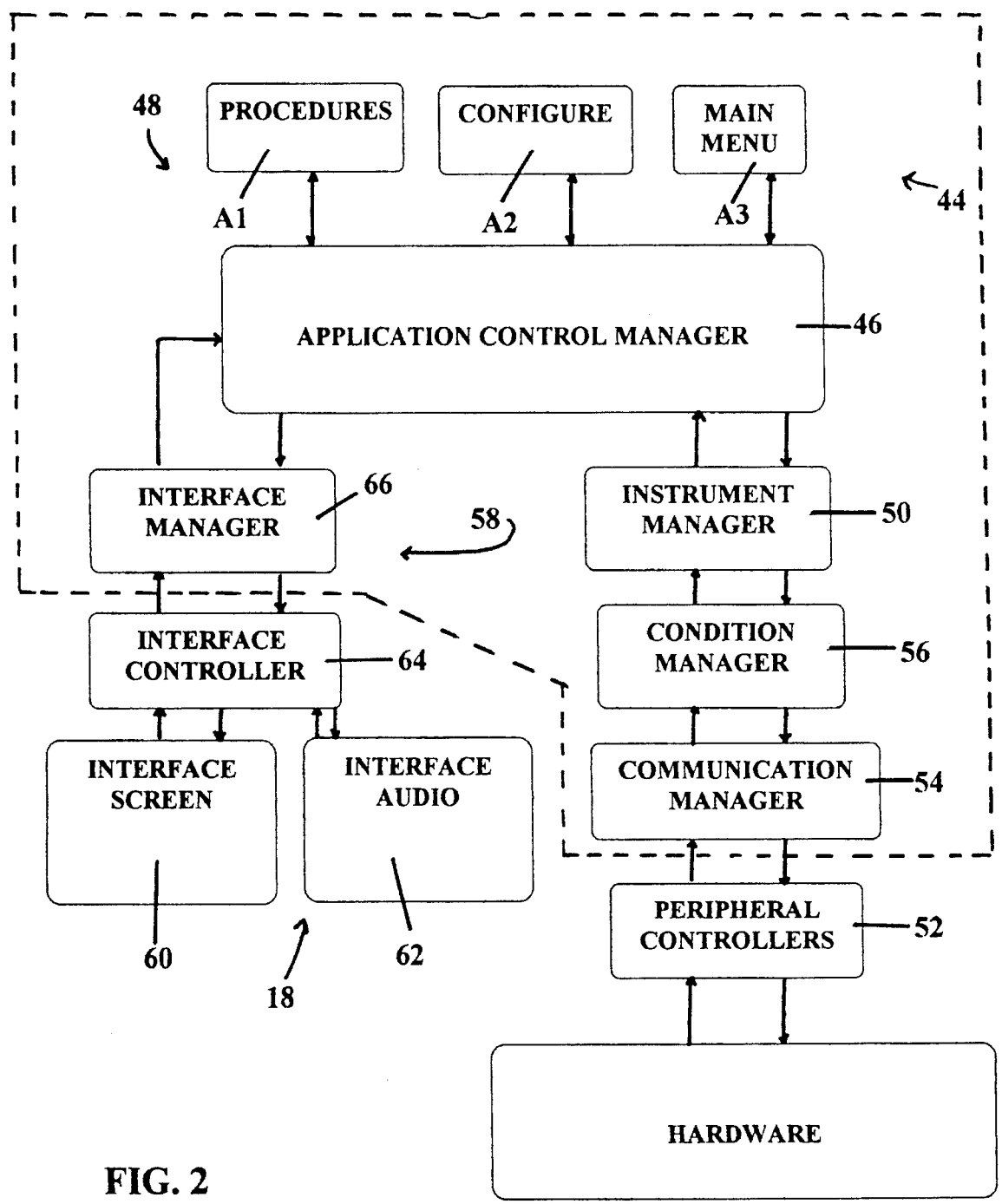
FIG. 2 is a diagrammatic flow chart view of the controller and associated interface that embodies the features of the invention.

Figure 2. Data Flow Diagram 1.1: User_Interface_Manager

This diagram denotes a special, separate function called "Edit_Data". Edit_Data is a utility which can be invoked by either (a) an external process or (b) by the Control_User_Interface process. This latter function allows certain, defined fields within a window to automatically invoke the Edit_Data function when selected by the user.

The locally-shown Value_Description_Tables contains descriptions of all values used by the system. This information is used to (a) identify information (by type of value), (b) define how information is formatted for display to the user, and (c) provide information to allow the user to edit the value.

6.1.1.1. Functional Requirement Control_User_Inteface

This process is responsible for managing video screen displays, audio outputs, light outputs, and touch screen inputs.

a. Inputs

*Command_from_Display_Msg* from: Offpage.1.1
*Diagnostic_Command*
  from: Offpage.1.1
*Response_from_Display*
  from: Offpage.1.1
*Value_Description_Tables* ::= Value_Table + Enumeration_Table
  from: Value_Description_Tables
 *Window_Command* ::= [Open_Window_Command | Front_Window_Command | Close_Window_Command | Set_-Window_Mode_Command | Set_Audio_Command | Set_Lights_Command]
  from: Edit_Data
  from: Offpage.1.1
*Window_Data* ::= Window_Data_Semaphore + Window_Data_Value_List
  from: Edit_Data
  from: Offpage.1.1 b. Outputs

*Command_to_Display*
  to: Offpage.1.1
*Diagnostic_Data*
  to: Offpage.1.1
*Edit_Info* ::= Value_Object + Edit_Type + Edit_Qid
  to: Edit_Data
*Response_to_Display*
  to: Offpage.1.1
*User_Function_Msg* ::= [Function_Code_Msg | Keyboard_Code_Msg]
  to: Edit_Data
  to: Offpage.1.1
*Window_ID* ::= "int"
  to: Edit_Data
  to: Offpage.1.1 c. Processing

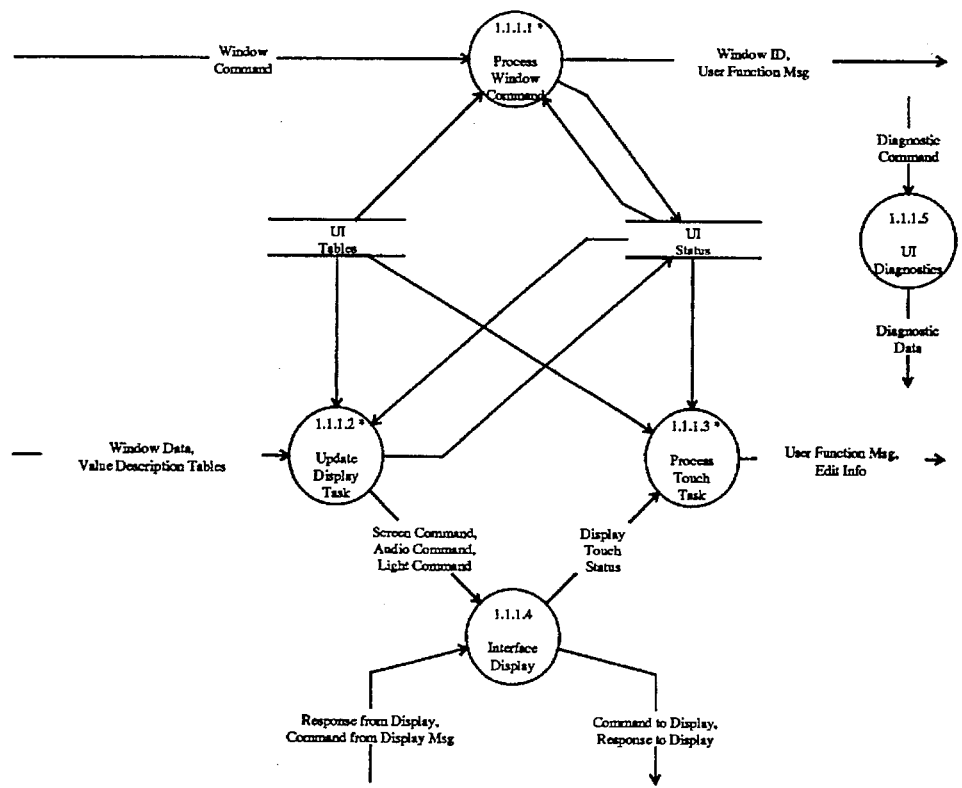

Figure 3. Data Flow Diagram 1.1.1: Control_User_Inteface

Constant (ROM-based) structures in the UI_Tables data store describe the layout and formatting of all display attributes, including regions, windows, and window fields. The UI_Status data store contains dynamic (RAM-based) structures which describe the current state of the User Interface.

External procedures manage the display via callable interfaces within Process_Window_Command. Process_Window_Command examines UI_Tables and UI_Status, creating or updating UI_Status structures. Update_Display_Task operates as a time-triggered task which performs all operations required to update screen, audio, and light outputs. Process_Button_Task awaits and asynchronously processes information regarding touch screen inputs from the display.

Interface_Display hides and handles the nuances of communication and coordination with the Display Processor.

Note: "UI_Diagnostics" will be defined at a future date.

6.1.1.1.1. Functional Requirement Process_Window_Command

This is a set of "callable" routines which are invoked by external processes. They establish parameters in the UI_Status structure which create, modify, erase windows, set audio outputs, and set physical light outputs.

a. Inputs

*UI_Status* ::= UI_Status_Semaphore + Screen_Status + Audio_Status + Light_Status
   from: UI_Status
*UI_Tables* ::= Screen_Tables
   from: UI_Tables
*Window_Command* ::= [Open_Window_Command | Front_Window_Command | Close_Window_Command | Set_-
Window_Mode_Command | Set_Audio_Command | Set_Lights_Command]
   from: Offpage.1.1.1 b. Outputs

*UI_Status* ::= UI_Status_Semaphore + Screen_Status + Audio_Status + Light_Status
   to: UI_Status
*User_Function_Msg* ::= [Function_Code_Msg | Keyboard_Code_Msg]
   to: Offpage.1.1.1
*Window_ID* ::= "int"
   to: Offpage.1.1.1 c. Processing

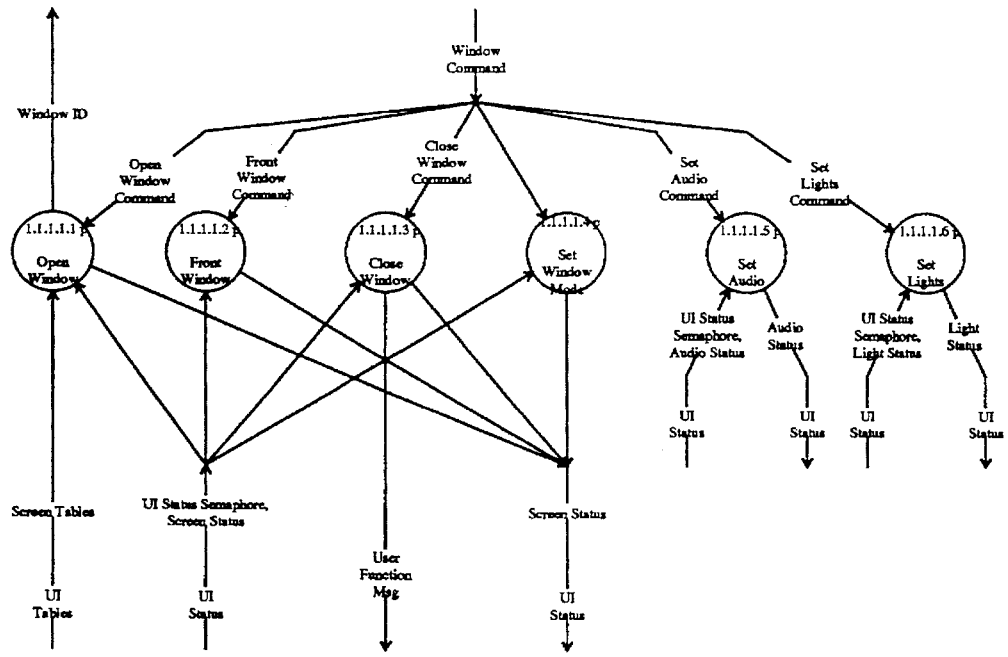

Figure 4. Data Flow Diagram 1.1.1.1: Process_Window_Command

This is a subsystem of externally callable commands use to create, modify, and delete windows and phyisical output information. Output state information is placed into the UI_Status data structure. Direct manipulation of the display or the Display Controller does not occur here.

6.1.1.1.1.1. Functional Requirement Open_Window

Open_Window performs all activities required to define a new, open window on display screen. Upon completion, the Window_ID for the newly created window is returned to the requestor.

The new window will display on top of all other windows in the display region (unless the window is defined as a "virtual window").

a. Inputs

*Open_Window_Command* ::= Window_Code + Region_Code + Window_Data_Ptr + User_Function_Qid + Parent_Window_ID + Auto_Close_Window_ID
        from: Offpage.1.1.1.1
    *Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
        from: Offpage.1.1.1.1
    *Screen_Tables* ::= Region_Description_Table + Window_Description_Table + Color_Tables + Image_Description_Table + Language_Window_Table
        from: Offpage.1.1.1.1
    *UI_Status* ::= UI_Status_Semaphore + Screen_Status + Audio_Status + Light_Status
        from: Offpage.1.1.1.1
    *UI_Status_Semaphore* ::= "pSOS SMid"
        from: Offpage.1.1.1.1
    *UI_Tables* ::= Screen_Tables
        from: Offpage.1.1.1.1
    *Window_Command* ::= [Open_Window_Command | Front_Window_Command | Close_Window_Command | Set_Window_Mode_Command | Set_Audio_Command | Set_Lights_Command]
        from: Offpage.1.1.1.1 b. Outputs

*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
        to: Offpage.1.1.1.1
    *UI_Status* ::= UI_Status_Semaphore + Screen_Status + Audio_Status + Light_Status
        to: Offpage.1.1.1.1
    *Window_ID* ::= "int"
        to: Offpage.1.1.1.1 c. Processing

```
Process 1.1.1.1.1: Open_Window
```

Pspec generated
11 February 1993 by lyle

DESCRIPTION

Grab UI_Status_Semaphore

If an Auto_Close_Window is given, then close the indicated window using
the "Close_Window" process alogorithm.

Lookup and translate Window_Code in Language_Window_Table
based upon the current language.

Obtain an empty (unused) Window_Status entry in the Window_Status_List.

Create link with parent window, if required.

Store initial values into Window_Status structure.
Set Draw_Window_Flag.

if this is a virtual window:

Find free Virtual_Frame_Status and assign it to this window.
if window is a root window
Place window at end of linked list starting with
Region_Status.First_Window_ID.
endif else Find root-parent window to this window and place root-parent window
at the beginning of the linked list starting with
Region_Status.First_Window_ID.

endif.

Set Draw_Window_Flag.

Restore UI_Status_Semaphore

END PSPEC

6.1.1.1.1.2. Functional Requirement Front_Window

Front_Window places the indicated window at the top of the window list. This will cause the window display in front
of all other windows in the region on the display screen. (Note: The youngest "child" of the indicated window is displayed.)

a. Inputs

*Front_Window_Command* ::= Window_ID
  from: Offpage.1.1.1.1
 *Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
  from: Offpage.1.1.1.1
 *UI_Status* ::= UI_Status_Semaphore + Screen_Status + Audio_Status + Light_Status
  from: Offpage.1.1.1.1
 *UI_Status_Semaphore* ::= "pSOS SMid"
  from: Offpage.1.1.1.1
 *Window_Command* ::= [Open_Window_Command I Front_Window_Command I Close_Window_Command I Set_Window_Mode_Command I Set_Audio_Command I Set_Lights_Command]
  from: Offpage.1.1.1.1 b. Outputs

*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
  to: Offpage.1.1.1.1
 *UI_Status* ::= UI_Status_Semaphore + Screen_Status + Audio_Status + Light_Status
  to: Offpage.1.1.1.1 c. Processing

```
Process 1.1.1.1.2: Front_Window

Pspec generated
11 February 1993 by lyle

DESCRIPTION

Grab UI_Status_Semaphore

Find root-parent window for the requested window.

Place the root-parent window at the head of the region-linked list.

Restore UI_Status_Semaphore

END PSPEC
```

6.1.1.1.1.3. Functional Requirement Close_Window

Close_Window deletes the indicated window.

If the window was being displayed, the most recent window previously displayed will be displayed in its place.

User_Function_Msg is used to notify the owner of a "child" window that it is being closed do a request to close its parent window (this lets the Edit_Data process know that the window it is using for editing a value is no longer valid).

a. Inputs

*Close_Window_Command* ::= Window_ID
   from: Offpage.1.1.1.1
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
   from: Offpage.1.1.1.1
*UI_Status* ::= UI_Status_Semaphore + Screen_Status + Audio_Status + Light_Status
   from: Offpage.1.1.1.1
*UI_Status_Semaphore* ::= "pSOS SMid"
   from: Offpage.1.1.1.1
*Window_Command* ::= [Open_Window_Command | Front_Window_Command | Close_Window_Command | Set_Window_Mode_Command | Set_Audio_Command | Set_Lights_Command]
   from: Offpage.1.1.1.1 b. Outputs

*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
   to: Offpage.1.1.1.1
*UI_Status* ::= UI_Status_Semaphore + Screen_Status + Audio_Status + Light_Status
   to: Offpage.1.1.1.1
*User_Function_Msg* ::= [Function_Code_Msg | Keyboard_Code_Msg]
   to: Offpage.1.1.1.1 c. Processing

```
Process 1.1.1.1.3: Close_Window

Pspec generated
11 February 1993 by lyle

DESCRIPTION .

/* Note: This basic alogorithm is also used by Open_Window to automatically
 * close a window when replacing it with a new one.
 */

Grab UI_Status_Semaphore.
```

```
if the indicated window is a root-parent window
Remove the Window_Status structure from region-linked list.
else
Remove the Window_Status of this child from the Window_Status of the parent.
endif
Add this Window_Status and its children to the Deleted Window linked list.

for this and all children of the window

Mark MARKED_FOR_DELETE_WINDOW_FLAG in Window_Status.Window_Flags.

Mark any allocated Virtual Frame to be free.

if window is a "child" of the requested window
Send User_Function_Msg = QUIT_WINDOW_USER_FUNCTION to response queue.
endif endfor Restore UI_Status_Semaphore.

END PSPEC
```

6.1.1.1.1.4. Functional Requirement Set_Window_Mode a. Inputs

*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
    from: Offpage.1.1.1.1
*UI_Status* ::= UI_Status_Semaphore + Screen_Status + Audio_Status + Light_Status
    from: Offpage.1.1.1.1
*UI_Status_Semaphore* ::= "pSOS SMid"
    from: Offpage.1.1.1.1
*Window_Command* ::= [Open_Window_Command | Front_Window_Command | Close_Window_Command | Set_Window_Mode_Command | Set_Audio_Command | Set_Lights_Command]
    from: Offpage.1.1.1.1 b. Outputs

*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
    to: Offpage.1.1.1.1
*UI_Status* ::= UI_Status_Semaphore + Screen_Status + Audio_Status + Light_Status to: Offpage.1.1.1.1 c. Processing

```
Process 1.1.1.1.4: Set_Window_Mode

Pspec generated
11 February 1993 by lyle

DESCRIPTION

Grab UI_Status_Semaphore.

Set Screen_Mode_Status.New_Screen_Mode to new Screen_Mode.

Restore UI_Status_Semaphore.

END PSPEC
```

6.1.1.1.1.5. Functional Requirement Set_Audio

This procedure is used to start or stop and audible alarm or tone.

a. Inputs

*Audio_Status* ::= Audio_Code + Audio_Forever_Flag + Audio_Duration + Audio_Tone_State + Audio_Base_Time
    from: Offpage.1.1.1.1
*Set_Audio_Command* ::= Audio_Code + Audio_Duration
    from: Offpage.1.1.1.1
*UI_Status* ::= UI_Status_Semaphore + Screen_Status + Audio_Status + Light_Status
    from: Offpage.1.1.1.1
*UI_Status_Semaphore* ::= "pSOS SMid"
    from: Offpage.1.1.1.1
*Window_Command* ::= [Open_Window_Command | Front_Window_Command | Close_Window_Command | Set_-Window_Mode_Command | Set_Audio_Command | Set_Lights_Command]
    from: Offpage.1.1.1.1 b. Outputs

*Audio_Status* ::= Audio_Code + Audio_Forever_Flag + Audio_Duration + Audio_Tone_State + Audio_Base_Time
    to: Offpage.1.1.1.1
*UI_Status* ::= UI_Status_Semaphore + Screen_Status + Audio_Status + Light_Status to: Offpage.1.1.1.1 c. Processing

```
Process 1.1.1.1.5: Set_Audio

Pspec generated
11 February 1993 by lyle

DESCRIPTION

Grab the UI_Status_Semaphore.

Set values from Set_Audio_Command into Audio_Status.
Audio_Base_Time = current system time.
Audio_Tone_State = 0.

if Audio_Duration is 0:
Set Audio_Forever_Flag.
else
Reset Audio_Forever_Flag.
endif Restore UI_Status_Semaphore.

END PSPEC
```

6.1.1.1.1.6. Functional Requirement Set_Lights

Set_Light is used to turn ON or OFF physical lights on the display. (These are not to be confused with "video" lights which occur on the display screen.)

a. Inputs

*Light_Status* ::= Current_Light_Status + New_Light_Status
   from: Offpage.1.1.1.1
*Set_Lights_Command* ::= Light_Code + Light_Value
   from: Offpage.1.1.1.1
*UI_Status* ::= UI_Status_Semaphore + Screen_Status + Audio_Status + Light_Status
   from: Offpage.1.1.1.1
*UI_Status_Semaphore* ::= "pSOS SMid"
   from: Offpage.1.1.1.1
*Window_Command* ::= [Open_Window_Command | Front_Window_Command | Close_Window_Command | Set_-

Window_Mode_Command | Set_Audio_Command | Set_Lights_Command]
   from: Offpage.1.1.1.1 b. Outputs

*Light_Status* ::= Current_Light_Status + New_Light_Status
   to: Offpage.1.1.1.1
*UI_Status* ::= UI_Status_Semaphore + Screen_Status + Audio_Status + Light_Status
   to: Offpage.1.1.1.1 c. Processing

```
Process 1.1.1.1.6: Set_Lights

Pspec generated
11 February 1993 by lyle

DESCRIPTION

Grab UI_Status_Semaphore.

switch based on Light_Code:

case = DONOR_LIGHT

Set New_Light_Status Donor Lights.
break.

case = PROCEDURE_COMPLETE_LIGHT

Set New_Light_Status Procedure Complete lights.
break.

case = ALL_LIGHTS

Set New_Light_Status All Lights.
break.

endswitch

Restore UI_Status_Semaphore.

END PSPEC
```

6.1.1.1.2. Functional Requirement Update_Display_Task

Update_Display_Task performs real-time updating of the User Interface screen and other physical outputs. This task executes on a periodic basis in order to make updates to the User Interface.

All dynamic values which are to be displayed in window data fields are provided via Window_Data structures. One such structure exists for each open, displayed window (the memory location of the structure is provided when the window is created).

a. Inputs

*UI_Status* ::= UI_Status_Semaphore + Screen_Status + Audio_Status + Light_Status
    from: UI_Status
*UI_Tables* ::= Screen_Tables
    from: UI_Tables
*Value_Description_Tables* ::= Value_Table + Enumeration_Table
    from: Offpage.1.1.1
*Window_Data* ::= Window_Data_Semaphore + Window_Data_Value_List
    from: Offpage.1.1.1 b. Outputs

*Audio_Command*
    to: Interface_Display
*Light_Command*
    to: Interface_Display
*Screen_Command*
    to: Interface_Display
*UI_Status* ::= UI_Status_Semaphore + Screen_Status + Audio_Status + Light_Status
    to: UI_Status c. Processing

Figure 5:
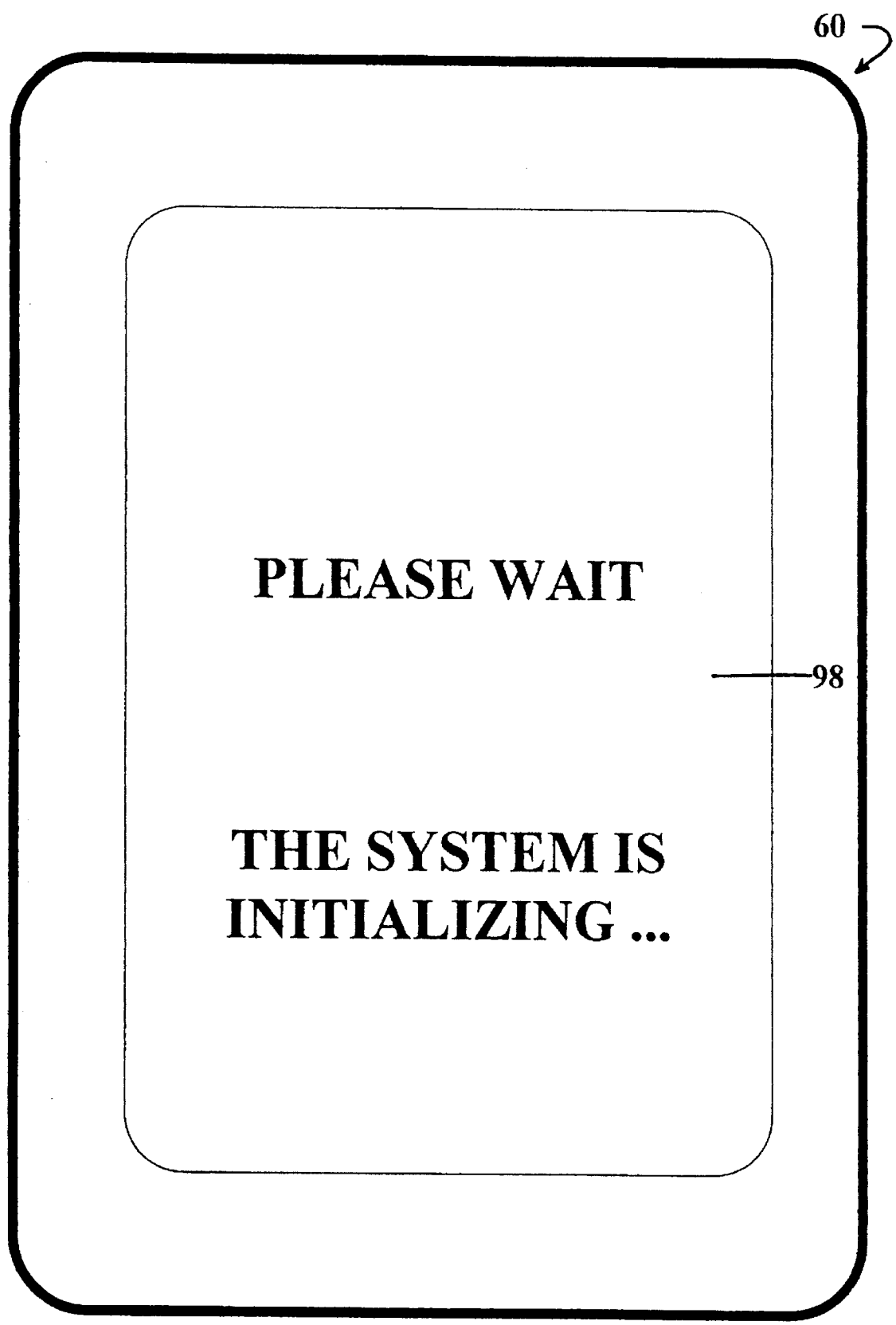
FIG. 5 is a view of the interface shown in FIG. 4 when in a full screen mode.

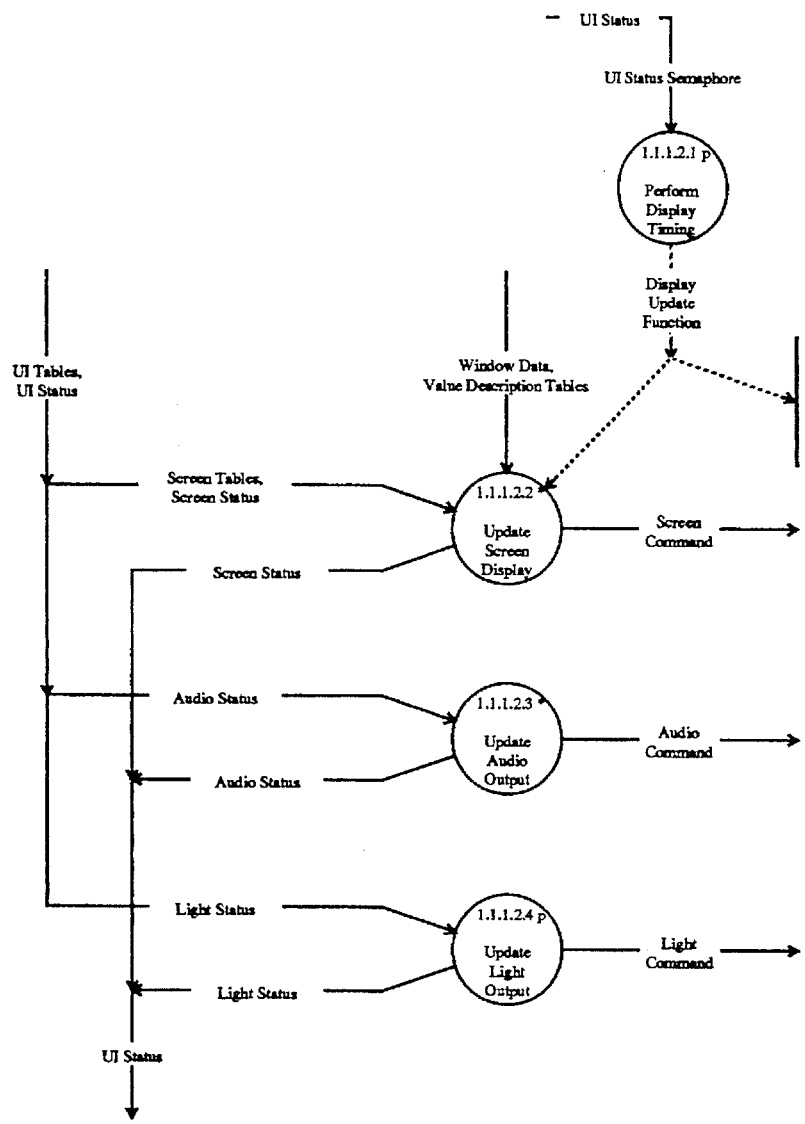
Figure 5. Data Flow Diagram 1.1.1.2: Update_Display_Task
Perform_Display_Timing is the primary (time-based) controlling process within this task.

| Control In | Activate Processes | | |
|---|---|---|---|
| Display Update Function | Update Screen Display | Update Audio Output | Update Light Output |
| UPDATE DISPLAY NORMAL | 1 | 1 | |
| UPDATE DISPLAY CRITICAL | 1 | | 1 |

Table 1. Control Specification: Process Activation Table

6.1.1.1.2.1. Functional Requirement Perform_Display_Timing

This process manages timing within the Update_Display_Task. This operates at a fixed frequency to provide:

(1) Updating of "critical" information, once each 1/10 second.

(2) Updating of other information, once each 1/3 second.

a. Inputs

> *UI_Status* ::= UI_Status_Semaphore + Screen_Status + Audio_Status + Light_Status
>     from: Offpage.1.1.1.2
> *UI_Status_Semaphore* ::= "pSOS SMid"
>     from: Offpage.1.1.1.2 b. Outputs

> *Display_Update_Function* ::= "control flag(s)"
>     to: Update_Screen_Display
>     to: 1.1.1.2 c. Processing

Process 1.1.1.2.1: Perform_Display_Timing

Pspec generated
3 February 1993 by lyle

DESCRIPTION

Execute every 0.10s:

if (interval since last update greater than or equal to 0.30s)
Display_Update_Function += Update_Display_Normal
else
Display_Update_Function += Update_Display_Critical
endif Grab UI_Status_Semaphore.
Signal Update_Display_Function.
Restore UI_Status_Semaphore.

endLoop

END PSPEC

6.1.1.1.2.2. Functional Requirement Update_Screen_Display

Update_Screen_Display manages all aspects of the video screen display. The Region_ and Window_Status_Lists identify windows to be updated. Window_Data defines data fields to be updated. Display_Tables and Value_Description provide screen formatting information. Screen_Commands are generated in order to update the screen display.

a. Inputs

*Display_Update_Function* ::= "control flag(s)"
    from: Perform_Display_Timing
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
    from: Offpage.1.1.1.2
*Screen_Tables* ::= Region_Description_Table + Window_Description_Table + Color_Tables + Image_Description_Table + Language_Window_Table
    from: Offpage.1.1.1.2
*UI_Status* ::= UI_Status_Semaphore + Screen_Status + Audio_Status + Light_Status
    from: Offpage.1.1.1.2
*UI_Tables* ::= Screen_Tables
    from: Offpage.1.1.1.2
*Value_Description_Tables* ::= Value_Table + Enumeration_Table
    from: Offpage.1.1.1.2

*Window_Data* ::= Window_Data_Semaphore + Window_Data_Value_List
   from: Offpage.1.1.1.2 b. Outputs

*Screen_Command*
   to: Offpage.1.1.1.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
   to: Offpage.1.1.1.2
*UI_Status* ::= UI_Status_Semaphore + Screen_Status + Audio_Status + Light_Status
   to: Offpage.1.1.1.2 c. Processing

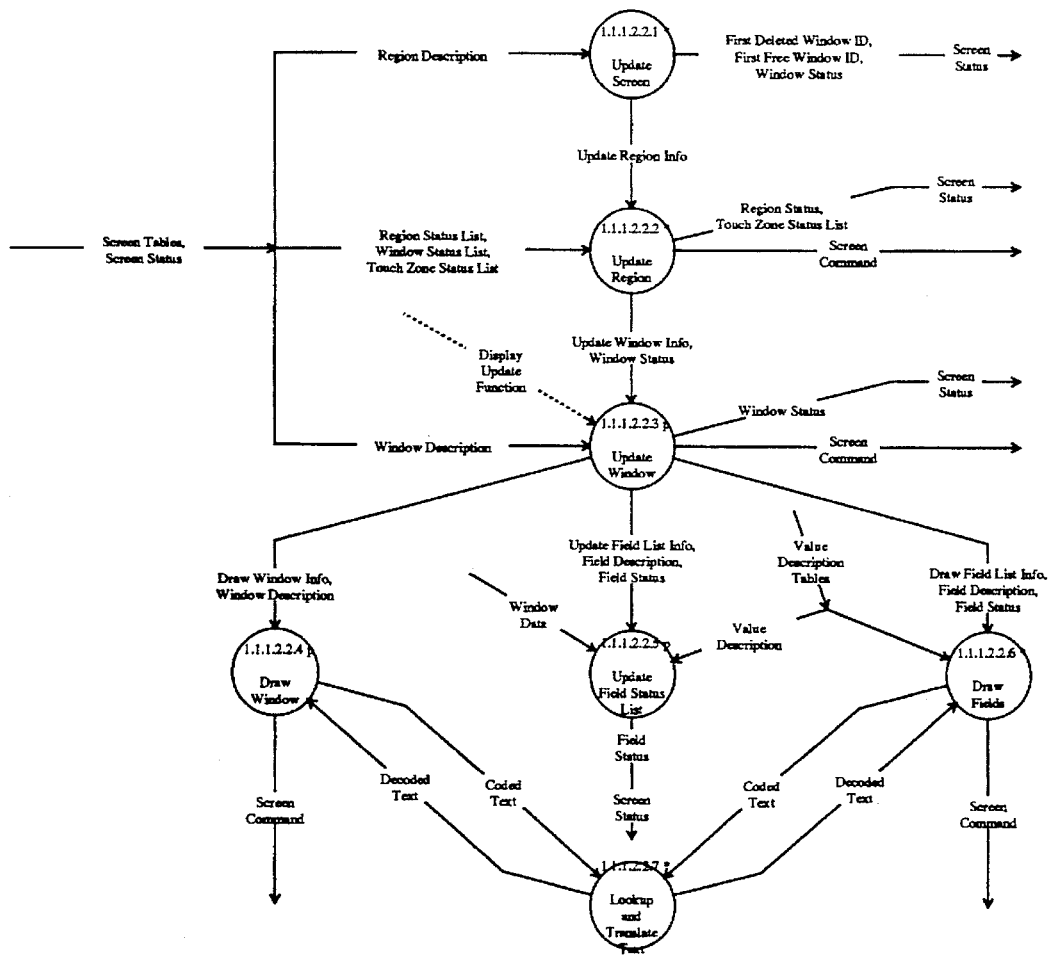
Figure 6. Data Flow Diagram 1.1.1.2.2: Update_Screen_Display
The primary (driving) process is Update_Screen.
6.1.1.1.2.2.1. Functional Requirement Update_Screen
This process puts together information about each display region and passes that information on so that the region can be updated.
a. Inputs

*Region_Description* ::= Region_Code + Display_Location
  from: Offpage.1.1.1.2.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
  from: Offpage.1.1.1.2.2
*Screen_Tables* ::= Region_Description_Table + Window_Description_Table + Color_Tables + Image_Description_Table + Language_Window_Table
  from: Offpage.1.1.1.2.2 b. Outputs

*First_Deleted_Window_ID* ::= "Window_ID"
  to: Offpage.1.1.1.2.2
*First_Free_Window_ID* ::= "Window_ID"
  to: Offpage.1.1.1.2.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
  to: Offpage.1.1.1.2.2
*Update_Region_Info* ::= Region_Code + Region_Active + Region_Base_Display_Location
  to: Update_Region
*Window_Status* ::= Region_Code + Next_Window_ID + Parent_Window_ID + Window_Flags + Child_Window_ID + Window_Description_Ptr + Display_Frame_Number + Window_Data_Ptr + User_Function_Qid + Field_Status_List
  to: Offpage.1.1.1.2.2 c. Processing

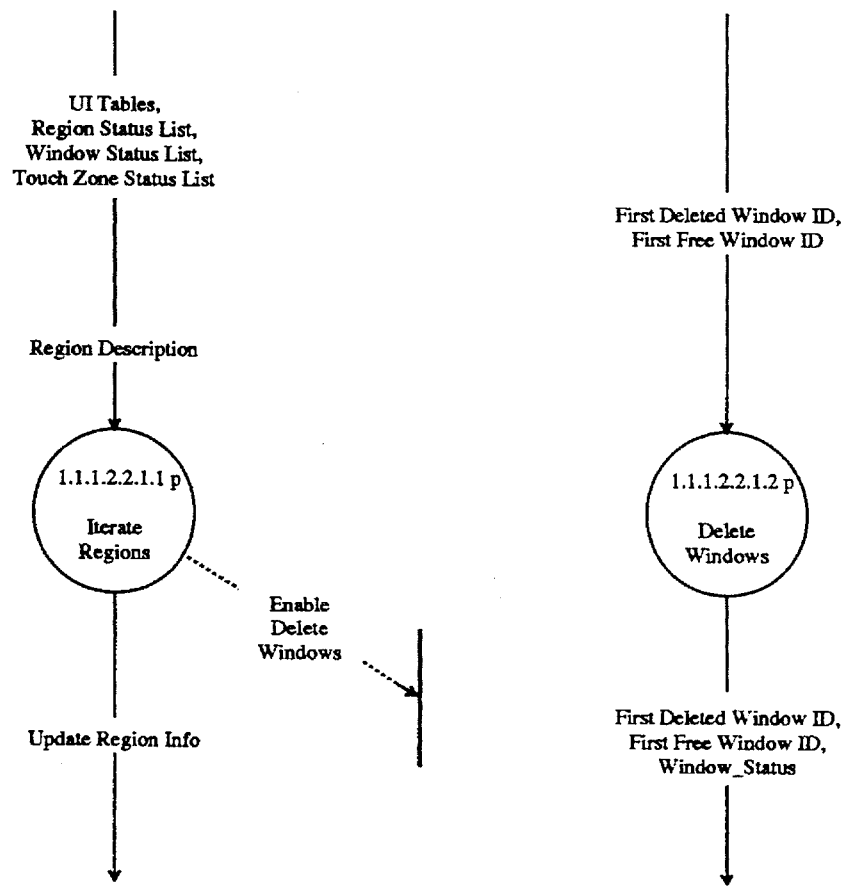
Figure 7. Data Flow Diagram 1.1.1.2.2.1: Update_Screen
Iterate Regions is the controlling process.

| Control In | Activate Processes |
|---|---|
| Enable Delete Windows | Delete Windows |
| 0 | 0 |
| 1 | 1 |

Table 2. Control Specification: Process Activation Table

6.1.1.1.2.2.1.1. Functional Requirement Iterate_Regions a. Inputs

*Region_Description* ::= Region_Code + Display_Location
        from: Offpage.1.1.1.2.2.1
    *Region_Status_List* ::= {Region_Status}
        from: Offpage.1.1.1.2.2.1
    *Touch_Zone_Status_List* ::= {Touch_Zone_Status}
        from: Offpage.1.1.1.2.2.1
    *UI_Tables* ::= Screen_Tables
        from: Offpage.1.1.1.2.2.1
    *Window_Status_List* ::= {Window_Status}
        from: Offpage.1.1.1.2.2.1 b. Outputs

*Enable_Delete_Windows* ::= "Control"
        to: 1.1.1.2.2.1
    *Update_Region_Info* ::= Region_Code + Region_Active + Region_Base_Display_Location
        to: Offpage.1.1.1.2.2.1 c. Processing

Process 1.1.1.2.2.1.1: Iterate_Regions

Pspec generated
11 February 1993 by lyle

DESCRIPTION

```
/* Note: Examine Screen_Mode_Status.New_Screen_Status and operate on
 * regions which are not used in this Screen_Mode first.  This allows
 * these regions to be removed from the physical display into virtual
 * screen storage PRIOR to being overwritten by new screens.
 */
```

For each region
Calculate and send Region_Update_Info.

Enable Delete_Windows.

END PSPEC

6.1.1.1.2.2.1.2. Functional Requirement Delete_Windows a. Inputs

*First_Deleted_Window_ID* ::= "Window_ID"
  from: Offpage.1.1.1.2.2.1
*First_Free_Window_ID* ::= "Window_ID"
  from: Offpage.1.1.1.2.2.1 b. Outputs

*First_Deleted_Window_ID* ::= "Window_ID"
  to: Offpage.1.1.1.2.2.1
*First_Free_Window_ID* ::= "Window_ID"
  to: Offpage.1.1.1.2.2.1
*Window_Status* ::= Region_Code + Next_Window_ID + Parent_Window_ID + Window_Flags + Child_Window_ID + Window_Description_Ptr + Display_Frame_Number + Window_Data_Ptr + User_Function_Qid + Field_Status_List
  to: Offpage.1.1.1.2.2.1 c. Processing

Process 1.1.1.2.2.1.2: Delete_Windows

Pspec generated
11 February 1993 by lyle

DESCRIPTION

/* Note: We rely on other, previously invoked processes to reset any formerly
 * active Touch Zones for these window which we are going to delete here.
 */ for this and all children of the window

Clear the Window_Status structure IN_USE_WINDOW_FLAG
and MARKED_FOR_DELETE_WINDOW_FLAGs.
Move the Window_Status structure to the free list.

endfor

Restore UI_Status_Semaphore.

END PSPEC

6.1.1.1.2.2.2. Functional Requirement Update_Region

This process manages the virtual areas on the display and identifies which windows in the Window_Status_List are required to be updated.

a. Inputs

*Region_Status_List* ::= {Region_Status}
   from: Offpage.1.1.1.2.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
   from: Offpage.1.1.1.2.2
*Screen_Tables* ::= Region_Description_Table + Window_Description_Table + Color_Tables + Image_Description_Table + Language_Window_Table
   from: Offpage.1.1.1.2.2
*Touch_Zone_Status_List* ::= {Touch_Zone_Status}
   from: Offpage.1.1.1.2.2
*Update_Region_Info* ::= Region_Code + Region_Active + Region_Base_Display_Location
   from: Update_Screen
*Window_Status_List* ::= {Window_Status}
   from: Offpage.1.1.1.2.2 b. Outputs

*Region_Status* ::= Current_Displayed_Window_ID + First_Window_ID
   to: Offpage.1.1.1.2.2
*Screen_Command*
   to: Offpage.1.1.1.2.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
   to: Offpage.1.1.1.2.2
*Touch_Zone_Status_List* ::= {Touch_Zone_Status}
   to: Offpage.1.1.1.2.2
*Update_Window_Info* ::= Window_ID + Virtual_Area_Number + Base_Display_Location
   to: Update_Window
*Window_Status* ::= Region_Code + Next_Window_ID + Parent_Window_ID + Window_Flags + Child_Window_ID + Window_Description_Ptr + Display_Frame_Number + Window_Data_Ptr + User_Function_Qid + Field_Status_List
   to: Update_Window c. Processing

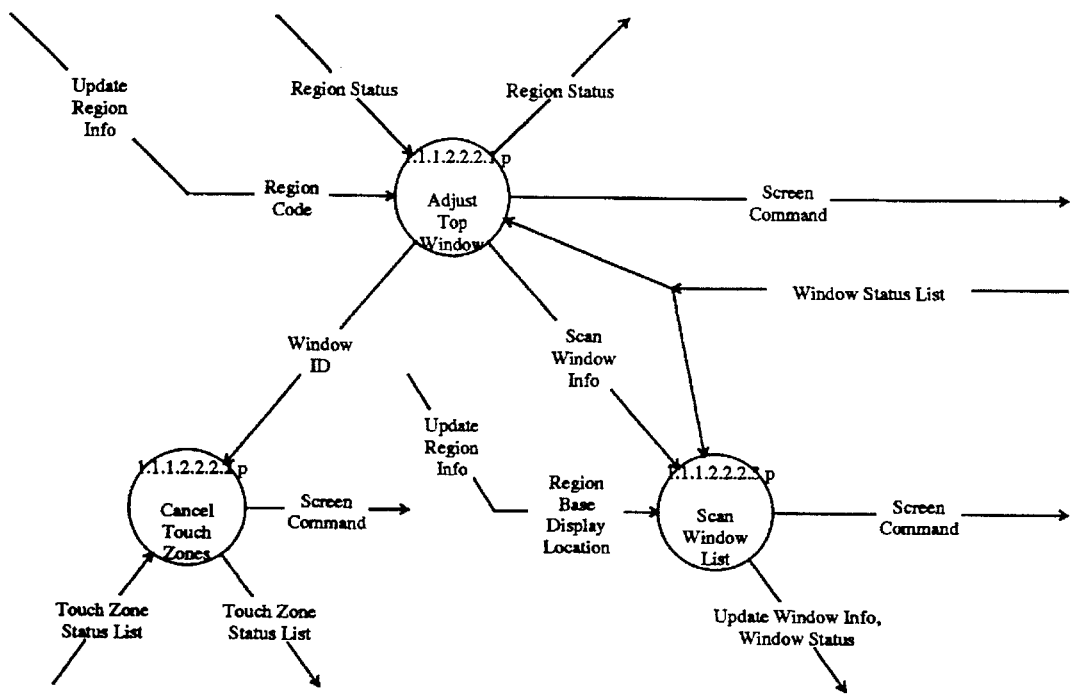

Figure 8. Data Flow Diagram 1.1.1.2.2.2: Update_Region

Adjust_Top_Window is the controlling process.

6.1.1.1.2.2.2.1. Functional Requirement Adjust_Top_Window

This process moves windows which are stored in "Virtual Areas" on the Display Controller to/from the real screen display.

a. Inputs

*Region_Code* ::= "integer"
  from: Offpage.1.1.1.2.2.2
*Region_Status* ::= Current_Displayed_Window_ID + First_Window_ID
  from: Offpage.1.1.1.2.2.2
*Update_Region_Info* ::= Region_Code + Region_Active + Region_Base_Display_Location
  from: Offpage.1.1.1.2.2.2
*Window_Status_List* ::= {Window_Status}
  from: Offpage.1.1.1.2.2.2 b. Outputs

*Region_Status* ::= Current_Displayed_Window_ID + First_Window_ID
  to: Offpage.1.1.1.2.2.2
*Scan_Window_Info* ::= First_Window_ID + Region_Active + Currently_Displayed_Window_ID
  to: Scan_Window_List
*Screen_Command*
  to: Offpage.1.1.1.2.2.2
*Window_ID* ::= "int"
  to: Cancel_Touch_Zones c. Processing

```
Process 1.1.1.2.2.2.1: Adjust_Top_Window

Pspec generated
22 February 1993 by lyle

DESCRIPTION

Top_Window_ID = youngest child of First_Window_ID.

if (Currently_Displayed_Window_ID for this region
is not the same as Top_Window_ID)

if (Current_Displayed_Window_ID is not the NULL_WINDOW_ID)

/* Erase Touch Zones for Current Window */
send Window_ID = Currently_Displayed_Window_ID.
```

```
/* Move Current Window back to its Virtual Frame */
if (Window for Currently_Displayed_Window_ID is Virtual)
Send Screen_Command = Copy display window to Virtual_Frame.
endif endif if (Top_Window_ID is not the NULL window) and (Region is Active)

/* Move New Top Window from its Virtual Frame to the screen */
if     (Window for Top_Window_ID is Virtual)
AND (the Draw_Window_Flag is not set)
Send Screen_Command = Copy Virtual_Frame to display window.
endif endif endif Send Scan_Window_Info.

END PSPEC
```

6.1.1.1.2.2.2.2. Functional Requirement Cancel_Touch_Zones

This process deletes all known button entries for a given Window_ID.

a. Inputs

*Touch_Zone_Status_List* ::= {Touch_Zone_Status}
   from: Offpage.1.1.1.2.2.2
*Window_ID* ::= "int"
   from: Adjust_Top_Window b. Outputs

*Screen_Command*
   to: Offpage.1.1.1.2.2.2
*Touch_Zone_Status_List* ::= {Touch_Zone_Status}
   to: Offpage.1.1.1.2.2.2 c. Processing

Process 1.1.1.2.2.2.2: Cancel_Touch_Zones

Pspec generated
22 February 1993 by lyle

DESCRIPTION for Touch_Zone = 0 to MAX_TOUCH_ZONE_NUMBER - 1:

/* Note: MAX_TOUCH_ZONE_NUMBER is reserved for Emergency Stop and
 * therefore is not a Touch Zone.
 */ if (Touch_Zone_Status IN_USE) && (Touch_Zone_Status Window_ID == Window_ID)
Touch_Zone_State = FREE.
Send Screen_Command = Delete Button.
endif endfor

END PSPEC

6.1.1.1.2.2.2.3. Functional Requirement Scan_Window_List

This process scans the linked list of windows, starting with the first window in the Region linked list, and identifies windows which must be updated in some fashion on the Display Controller in either real or virtual screen pages.

a. Inputs

*Region_Base_Display_Location* ::= "Base_Display_Location"
   from: Offpage.1.1.1.2.2.2
*Scan_Window_Info* ::= First_Window_ID + Region_Active + Currently_Displayed_Window_ID
   from: Adjust_Top_Window
*Update_Region_Info* ::= Region_Code + Region_Active + Region_Base_Display_Location
   from: Offpage.1.1.1.2.2.2
*Window_Status_List* ::= {Window_Status}
   from: Offpage.1.1.1.2.2.2 b. Outputs

*Screen_Command*
   to: Offpage.1.1.1.2.2.2
*Update_Window_Info* ::= Window_ID + Virtual_Area_Number + Base_Display_Location to: Offpage.1.1.1.2.2.2

*Window_Status* ::= Region_Code + Next_Window_ID + Parent_Window_ID + Window_Flags + Child_Window_ID + Window_Description_Ptr + Display_Frame_Number + Window_Data_Ptr + User_Function_Qid + Field_Status_List to: Offpage.1.1.1.2.2.2 c. Processing

```
Process 1.1.1.2.2.2.3: Scan_Window_List

Pspec generated
22 February 1993 by lyle

DESCRIPTION

Find root Window_ID of First_Window_ID.

if (root Window_ID is not the  NULL_WINDOW_ID) AND (the Region is Active)

for each root Window_ID in linked list and all children Window_IDs.

if (    (Window_ID == Currently_Displayed_Window_ID)
OR (Window_Status for Window_ID has a Virtual_Frame) )

/* Calculate Screen Page */
if (Window_ID = Currently_Displayed_Window_ID)
Virtual_Frame_Number = 0.
else
Virtual_Frame_Number = Window_Status Virtual_Frame_Number.
endif Send Window_Update_Info.

endif endfor else

Send Screen_Commands to blank the Window Region.

endif

END PSPEC
```

6.1.1.1.2.2.3. Functional Requirement Update_Window

This process manages the functions necessary to display new and modified windows or data fields on the display screen (or in Virtual Areas).

a. Inputs

*Display_Update_Function* ::= "control flag(s)"
        from: Offpage.1.1.1.2.2
    *Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
        from: Offpage.1.1.1.2.2
    *Screen_Tables* ::= Region_Description_Table + Window_Description_Table + Color_Tables + Image_Description_Table + Language_Window_Table
        from: Offpage.1.1.1.2.2
    *Update_Window_Info* ::= Window_ID + Virtual_Area_Number + Base_Display_Location
        from: Update_Region
    *Window_Description* ::= Window_Code + Display_Location + Window_Title + Window_Attributes + Field_Count + Field_Description_Table
        from: Offpage.1.1.1.2.2
    *Window_Status* ::= Region_Code + Next_Window_ID + Parent_Window_ID + Window_Flags + Child_Window_ID + Window_Description_Ptr + Display_Frame_Number + Window_Data_Ptr + User_Function_Qid + Field_Status_List
        from: Update_Region b. Outputs

*Draw_Field_List_Info* ::= Field_Count + First_Field_Status_Ptr + First_Field_Description_Ptr + Draw_Field_Background + Screen_Page + Window_Base_Display_Location + Window_ID
        to: Draw_Fields
    *Draw_Window_Info* ::= Window_Status_Ptr + Virtual_Area_Number + Base_Display_Location
        to: Draw_Window
    *Field_Description* ::= Field_Code + Field_Attributes + Display_Location + Field_Data_Type + Field_Format + Font_Code + Value_Code + User_Function_Code + Initial_Field_Colors_Code + Field_Format_Type + Field_Constant
        to: Draw_Fields
        to: Update_Field_Status_List
    *Field_Status* ::= Value_Modified + Scroll_Page_Number + Current_Field_Colors_Code + Current_Field_Attributes + Field_Value_List
        to: Draw_Fields
        to: Update_Field_Status_List
    *Screen_Command*
        to: Offpage.1.1.1.2.2
    *Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
        to: Offpage.1.1.1.2.2
    *Update_Field_List_Info* ::= Field_Update_Priority + Field_Count + First_Field_Description_Ptr + First_Field_Status_Ptr
        to: Update_Field_Status_List
    *Window_Description* ::= Window_Code + Display_Location + Window_Title + Window_Attributes + Field_Count + Field_Description_Table
    to: Draw_Window
*Window_Status* ::= Region_Code + Next_Window_ID + Parent_Window_ID + Window_Flags + Child_Window_-ID + Window_Description_Ptr + Display_Frame_Number + Window_Data_Ptr + User_Function_Qid + Field_Status_List
    to: Offpage.1.1.1.2.2 c. Processing

```
Process 1.1.1.2.2.3: Update_Window

Pspec generated
23 February 1993 by lyle

DESCRIPTION

Window_Display_Location = Base_Display_Location.

/* Display a brand new window */ if (Window_Status DRAW_WINDOW_FLAG is set)
Send Window_Draw_Info with Window_Display_Location.
New_Window = TRUE.
else
New_Window = FALSE.
endif /* Update field data in Field_Status */

Compute pointers to Field_Description and Field_Status.
if (New_Window)
Set Field_Update_Priority = "INITIAL"
elseif (Update_Display_Function = "CRITICAL") )
Set Field_Update_Priority = "CRITICAL"
else
Set Field_Update_Priority = "NORMAL"
endif
Send Update_Field_List_Info.

/* Update fields in the Display Controller */ if (New_Window)
Draw_Field_Background = TRUE.
else
Draw_Field_Background = FALSE.
endif
Send Draw_Field_List_Info.

Reset Window_Status DRAW_WINDOW_FLAG.

END PSPEC
```

6.1.1.1.2.2.4. Functional Requirement Draw_Window

This process puts a new "window background" on the screen (real or virtual).

a. Inputs

*Decoded_Text* ::= Decoded_Text_Body + Text_Terminator
   from: Lookup_and_Translate_Text
*Draw_Window_Info* ::= Window_Status_Ptr + Virtual_Area_Number + Base_Display_Location
   from: Update_Window
*Window_Description* ::= Window_Code + Display_Location + Window_Title + Window_Attributes + Field_Count + Field_Description_Table
   from: Update_Window b. Outputs

*Coded_Text* ::= Coded_Text_Body + Text_Terminator
   to: Lookup_and_Translate_Text
*Screen_Command*
   to: Offpage.1.1.1.2.2 c. Processing

```
Process 1.1.1.2.2.4: Draw_Window

Pspec generated
23 February 1993 by lyle

DESCRIPTION

Send Screen_Command = Erase Screen for window area.
Lookup and translate Window_Title.
Display Window Title in top-center of window area.
Send Screen_Command = Display Text for window title.

END PSPEC
```

6.1.1.1.2.2.5. Functional Requirement Update_Field_Status_List

Each open window has an associated Window_Data structure which is located within and maintained by the task which created the window. This process accesses those Window_Data structures in order to update values within their associated window data fields. Mutual exclusion access to the Window_Data structure is coordinated by a semaphore which is stored as the first element of the Window_Data structure.

a. Inputs

*Field_Description* ::= Field_Code + Field_Attributes + Display_Location + Field_Data_Type + Field_Format + Font_Code + Value_Code + User_Function_Code + Initial_Field_Colors_Code + Field_Format_Type + Field_Constant
    from: Update_Window
*Field_Status* ::= Value_Modified + Scroll_Page_Number + Current_Field_Colors_Code + Current_Field_Attributes + Field_Value_List
    from: Update_Window
*Update_Field_List_Info* ::= Field_Update_Priority + Field_Count + First_Field_Description_Ptr + First_Field_Status_Ptr
    from: Update_Window
*Value_Description* ::= Value_Code + Value_Type + Value_Title + Value_Display_Width + Value_Attributes
    from: Offpage.1.1.1.2.2
*Value_Description_Tables* ::= Value_Table + Enumeration_Table
    from: Offpage.1.1.1.2.2
*Window_Data* ::= Window_Data_Semaphore + Window_Data_Value_List
    from: Offpage.1.1.1.2.2 b. Outputs

*Field_Status* ::= Value_Modified + Scroll_Page_Number + Current_Field_Colors_Code + Current_Field_Attributes + Field_Value_List
    to: Offpage.1.1.1.2.2
*Screen_Status* ::= Screen_Mode_Status + Region_Status_List + First_Free_Window_ID + First_Deleted_Window_ID + Window_Status_List + Virtual_Frame_Status_List + Touch_Zone_Status_List + Keyboard_Window_ID
    to: Offpage.1.1.1.2.2 c. Processing

```
Process 1.1.1.2.2.5: Update_Field_Status_List

Pspec generated
23 February 1993 by lyle

DESCRIPTION

Index = 0.  /* Index into Window_Data_List array */

Grab Window_Data_Semaphore.

for Field_Count number of fields
```

```
/* Need to figure out "target" field if this is a "Control Field" */ if (Field_Data_Type = FIELD_COLORS_CONTROL_DATA_TYPE)
Target_Field = next non-control field in Field_List.
else
Target_Field = this field.
endif /* Are we are actually updating the field or skipping it until the future */ if (    (Field_Update_Priority = "INITIAL")
OR (Field_Update_Priority = "NORMAL")
OR (Target Field_Status Field_Attributes "CRITICAL" flag is set) )
Set Update_Flag.
else
Clear Update_Flag.
endif /* Now, save new Field_Values and flag any which have changed. */

Value_Modified_Flag_Bit = 1.
Field_Value_Index = 0.

switch on Field_Description Field_Data_Type case "CONDITION"
Check_Field_Value().
/* fall into next case */ case "VARIABLE"
Check_Field_Value().
/* fall into next case */ case "VALUE_OBJECT"
case "FIELD_COLORS_CONTROL"
Check_Field_Value().
break case "IMAGE_CONSTANT"
case "TEXT_CONSTANT"
break endswitch /* Special handling  for "Control Fields" */ if (FIELD_COLORS_CONTROL_DATA_TYPE) AND (Value_Modified_Flag is set)
Set Field_Modified flag in Target Value_Modified flags.
Copy Field_Value[0] into Target Current_Field_Colors_Code.
Reset Value_Modified_Flag.
endif /* Advance to the next field. */
```

```
Field_Status_Ptr++.
Field_Description_Ptr++.

endfor

Restore Window_Data_Semaphore.

/************************************************************
 * The following is an internal function to check for changes in the
 * Field_Value_List and set new values, if detected.
 ************************************************************/ begin Check_Field_Value:

/* Check an element from Window_Data */ if  (   (Field_Update_Priority = "INITIAL")
OR  (   (Update_Flag)
AND (   Window_Data_List[Index]
     != Field_Status Field_Value[Field_Value_Index])
    )
)
Set Value_Modified_Flag_Bit into Field_Status Value_Modified flag.
Field_Status Field_Value[Field_Value_Index] = Window_Data_List[Index].
endif /* Advance to next Window_Data, Field_Value, and Value_Modified elements. */

Shift Value_Modified_Flag_Bit left 1-bit.
Field_Value_Index++.
Index++.

end Check_Field_Value

END PSPEC
```

6.1.1.1.2.2.6. Functional Requirement Draw_Fields

This process performs initial display and update of individual fields within a window.

a. Inputs

*Decoded_Text* ::= Decoded_Text_Body + Text_Terminator
  from: Lookup_and_Translate_Text

*Draw_Field_List_Info* ::= Field_Count + First_Field_Status_Ptr + First_Field_Description_Ptr + Draw_Field_-Background + Screen_Page + Window_Base_Display_Location + Window_ID
   from: Update_Window
*Field_Description* ::= Field_Code + Field_Attributes + Display_Location + Field_Data_Type + Field_Format + Font_Code + Value_Code + User_Function_Code + Initial_Field_Colors_Code + Field_Format_Type + Field_Constant
   from: Update_Window
*Field_Status* ::= Value_Modified + Scroll_Page_Number + Current_Field_Colors_Code + Current_Field_Attributes + Field_Value_List
   from: Update_Window
*Value_Description_Tables* ::= Value_Table + Emumeration_Table
   from: Offpage.1.1.1.2.2 b. Outputs

*Coded_Text* ::= Coded_Text_Body + Text_Terminator
   to: Lookup_and_Translate_Text
*Screen_Command*
   to: Offpage.1.1.1.2.2 c. Processing

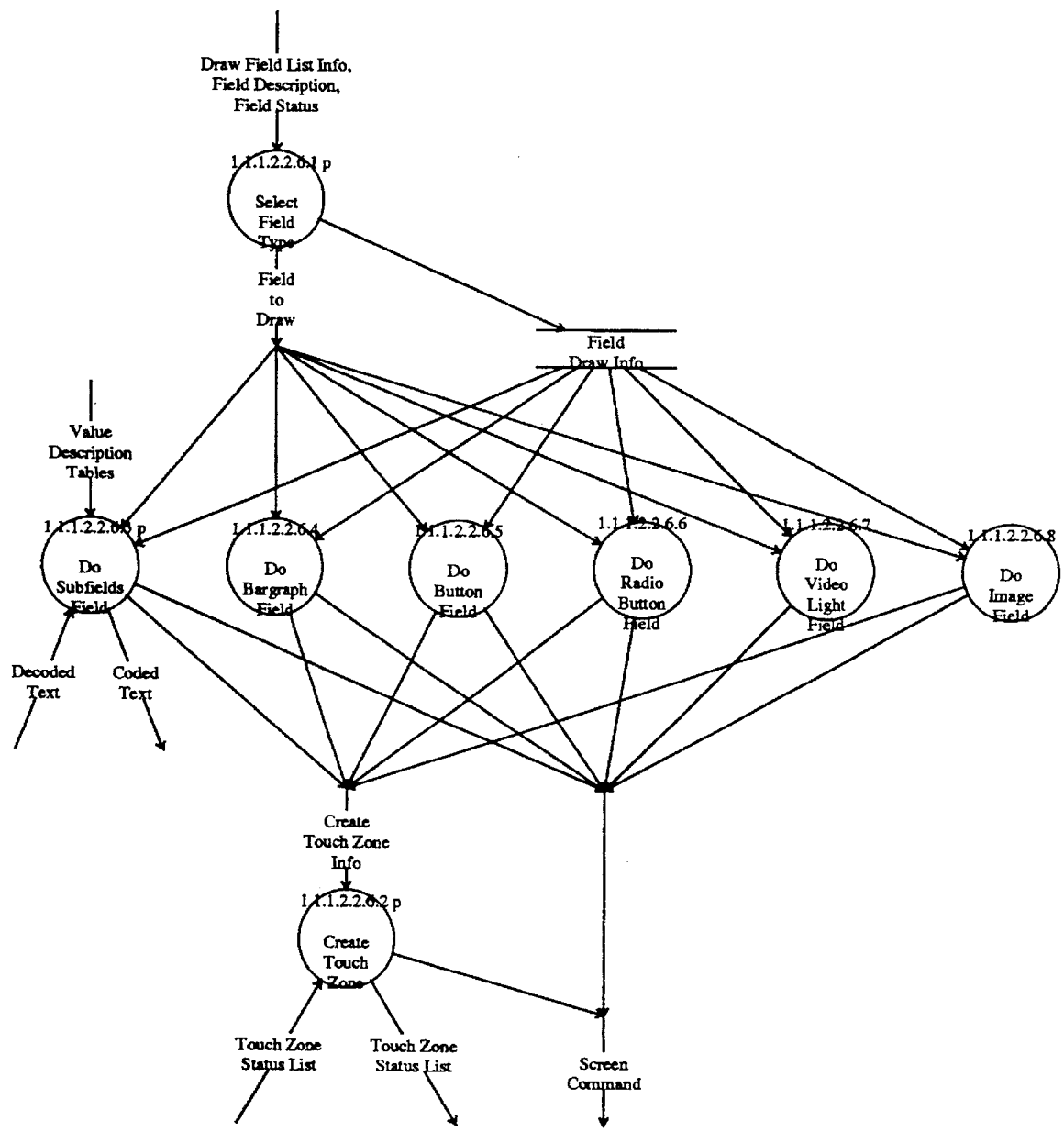
Figure 9. Data Flow Diagram 1.1.1.2.2.6: Draw_Fields
Select_Field_Type is the driving process.
Note: Some data flows, such and Coded_Text and Decoded_Text, go to/from all "Do xxxx Field" processes.

6.1.1.1.2.2.6.1. Functional Requirement Select_Field_Type

This process scans through through the Field Lists and sends "Fields_to_Draw" for any fields which must be updated.

a. Inputs

*Draw_Field_List_Info* ::= Field_Count + First_Field_Status_Ptr + First_Field_Description_Ptr + Draw_Field_Background + Screen_Page + Window_Base_Display_Location + Window_ID
   from: Offpage.1.1.1.2.2.6

*Field_Description* ::= Field_Code + Field_Attributes + Display_Location + Field_Data_Type + Field_Format + Font_Code + Value_Code + User_Function_Code + Initial_Field_Colors_Code + Field_Format_Type + Field_Constant
   from: Offpage.1.1.1.2.2.6

*Field_Status* ::= Value_Modified + Scroll_Page_Number + Current_Field_Colors_Code + Current_Field_Attributes + Field_Value_List
   from: Offpage.1.1.1.2.2.6 b. Outputs

*Field_Draw_Info* ::= Draw_Field_Background + Screen_Page + Window_Base_Display_Location + Window_ID
   to: Field_Draw_Info
*Field_to_Draw* ::= Field_Description_Ptr + Field_Status_Ptr + Field_Index
   to: Do_Subfields_Field
   to: Do_Bargraph_Field
   to: Do_Radio_Button_Field
   to: Do_Video_Light_Field
   to: Do_Button_Field
   to: Do_Image_Field c. Processing

```
Process 1.1.1.2.2.6.1: Select_Field_Type

Pspec generated
23 February 1993 by lyle

DESCRIPTION

Store Field_List_Draw_Info into Field_Draw_Info data store.

for Field_Count fields:

if (    (any Field_Modified flags in Field_Status are set)
OR (Draw_Field_Background flag is set) )

Send Field_to_Draw based upon Field_Format_Type.

Reset Field_Modified flags in Field_Status.
```

```
endif endfor

END PSPEC
```

6.1.1.1.2.2.6.2. Functional Requirement Create_Touch_Zone a. Inputs

*Create_Touch_Zone_Info* ::= Window_ID + Field_Index + Display_Location
   from: Do_Subfields_Field
   from: Do_Bargraph_Field
   from: Do_Radio_Button_Field
   from: Do_Button_Field
   from: Do_Image_Field
*Touch_Zone_Status_List* ::= {Touch_Zone_Status}
   from: Offpage.1.1.1.2.2.6 b. Outputs

*Screen_Command*
   to: Offpage.1.1.1.2.2.6
*Touch_Zone_Status_List* ::= {Touch_Zone_Status}
   to: Offpage.1.1.1.2.2.6 c. Processing

```
Process 1.1.1.2.2.6.2: Create_Touch_Zone

Pspec generated
23 February 1993 by lyle

DESCRIPTION

Search Touch_Zone_Status_List for UNUSED Touch_Zone_Status.
if found
Set values in Touch_Zone_Status structure.
Send Screen_Command = Create Button.
else
/* Significant Error */
endif
```

END PSPEC

6.1.1.1.2.2.6.3. Functional Requirement Do_Subfields_Field

This process updates fields which contain one, two, or three subfields.

a. Inputs

*Decoded_Text* ::= Decoded_Text_Body + Text_Terminator
      from: Offpage.1.1.1.2.2.6
    *Field_Draw_Info* ::= Draw_Field_Background + Screen_Page + Window_Base_Display_Location + Window_ID
      from: Field_Draw_Info
    *Field_to_Draw* ::= Field_Description_Ptr + Field_Status_Ptr + Field_Index
      from: Select_Field_Type
    *Value_Description_Tables* ::= Value_Table + Enumeration_Table
      from: Offpage.1.1.1.2.2.6 b. Outputs

*Coded_Text* ::= Coded_Text_Body + Text_Terminator
      to: Offpage.1.1.1.2.2.6
    *Create_Touch_Zone_Info* ::= Window_ID + Field_Index + Display_Location
      to: Create_Touch_Zone
    *Screen_Command*
      to: Offpage.1.1.1.2.2.6 c. Processing

```
Process 1.1.1.2.2.6.3: Do_Subfields_Field

Pspec generated
23 February 1993 by lyle

DESCRIPTION

/* Note for future PSpec:   Include SCROLL processing */

END PSPEC
```

6.1.1.1.2.2.6.4. Functional Requirement Do_Bargraph_Field

This process updates fields which contain bargraphs.

a. Inputs

*Field_Draw_Info* ::= Draw_Field_Background + Screen_Page + Window_Base_Display_Location + Window_ID
   from: Field_Draw_Info
*Field_to_Draw* ::= Field_Description_Ptr + Field_Status_Ptr + Field_Index
   from: Select_Field_Type b. Outputs

*Create_Touch_Zone_Info* ::= Window_ID + Field_Index + Display_Location
   to: Create_Touch_Zone
*Screen_Command*
   to: Offpage.1.1.1.2.2.6 c. Processing

6.1.1.1.2.2.6.5. Functional Requirement Do_Button_Field

This process updates fields which contain "buttons".

a. Inputs

*Field_Draw_Info* ::= Draw_Field_Background + Screen_Page + Window_Base_Display_Location + Window_ID
   from: Field_Draw_Info
*Field_to_Draw* ::= Field_Description_Ptr + Field_Status_Ptr + Field_Index
   from: Select_Field_Type b. Outputs

*Create_Touch_Zone_Info* ::= Window_ID + Field_Index + Display_Location
   to: Create_Touch_Zone
*Screen_Command*
   to: Offpage.1.1.1.2.2.6 c. Processing

6.1.1.1.2.2.6.6. Functional Requirement Do_Radio_Button_Field

This process updates fields which contain "Radio Buttons".

a. Inputs

*Field_Draw_Info* ::= Draw_Field_Background + Screen_Page + Window_Base_Display_Location + Window_ID
   from: Field_Draw_Info
*Field_to_Draw* ::= Field_Description_Ptr + Field_Status_Ptr + Field_Index
   from: Select_Field_Type b. Outputs

*Create_Touch_Zone_Info* ::= Window_ID + Field_Index + Display_Location
   to: Create_Touch_Zone
*Screen_Command*
   to: Offpage.1.1.1.2.2.6 c. Processing

6.1.1.1.2.2.6.7. Functional Requirement Do_Video_Light_Field

This process updates fields which contain Video Lights.

a. Inputs

*Field_Draw_Info* ::= Draw_Field_Background + Screen_Page + Window_Base_Display_Location + Window_ID
   from: Field_Draw_Info
*Field_to_Draw* ::= Field_Description_Ptr + Field_Status_Ptr + Field_Index
   from: Select_Field_Type b. Outputs

*Screen_Command*
   to: Offpage.1.1.1.2.2.6 c. Processing

6.1.1.1.2.2.6.8. Functional Requirement Do_Image_Field a. Inputs

*Field_Draw_Info* ::= Draw_Field_Background + Screen_Page + Window_Base_Display_Location + Window_ID
 from: Field_Draw_Info
*Field_to_Draw* ::= Field_Description_Ptr + Field_Status_Ptr + Field_Index
 from: Select_Field_Type b. Outputs

*Create_Touch_Zone_Info* ::= Window_ID + Field_Index + Display_Location
 to: Create_Touch_Zone
*Screen_Command*
 to: Offpage.1.1.1.2.2.6 c. Processing

6.1.1.1.2.2.7. Functional Requirement Lookup_and_Translate_Text

This process performs lookup of messages according to the language currently selected by the operator. All textual information (except that entered by the operator or from other external sources) is kept within this process.

Note: This process should be implemented as a general subsystem so that it's text translation features can be utilized where required in report generation and communications applications.

a. Inputs

*Coded_Text* ::= Coded_Text_Body + Text_Terminator
 from: Draw_Window
 from: Draw_Fields b. Outputs

*Decoded_Text* ::= Decoded_Text_Body + Text_Terminator
 to: Draw_Window
 to: Draw_Fields c. Processing

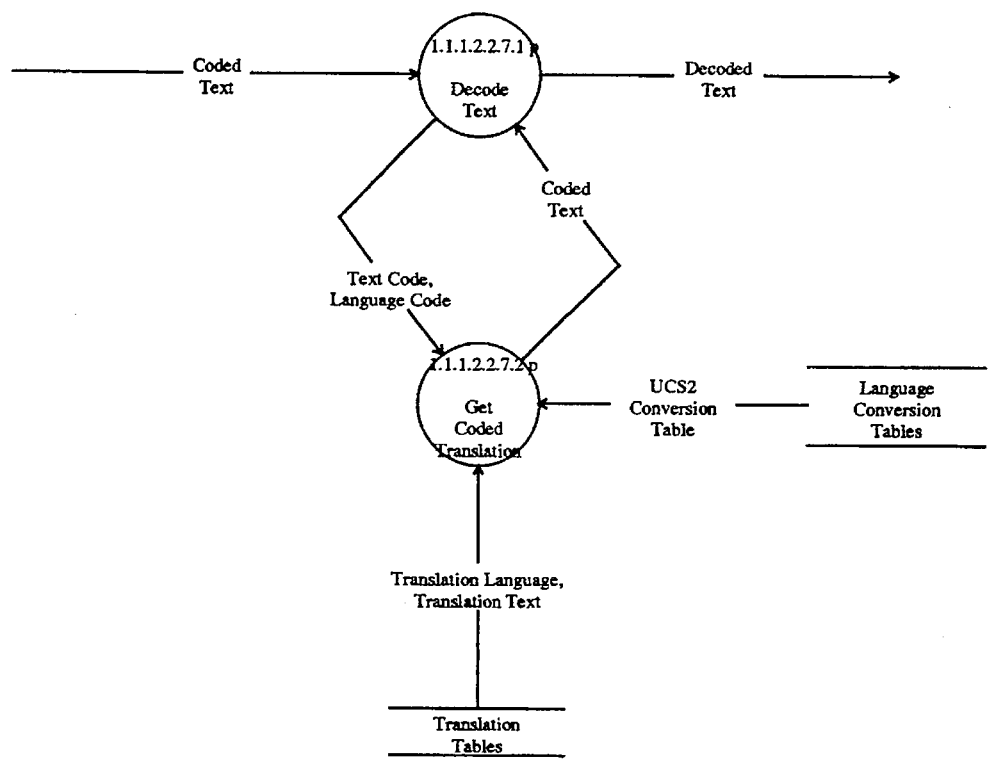

Figure 10. Data Flow Diagram 1.1.1.2.2.7: Lookup_and_Translate_Text 6.1.1.1.2.2.7.1. Functional Requirement Decode_Text This process looks up all built-in textual (i.e., character) messages within the system according to the currently selected language.

a. Inputs

*Coded_Text* ::= Coded_Text_Body + Text_Terminator
        from: Offpage.1.1.1.2.2.7
        from: Get_Coded_Translation b. Outputs

*Decoded_Text* ::= Decoded_Text_Body + Text_Terminator
        to: Offpage.1.1.1.2.2.7

*Language_Code* ::= "enumerated"
   to: Get_Coded_Translation
*Text_Code* ::= "unsigned short integer"
   to: Get_Coded_Translation c. Processing

```
Process 1.1.1.2.2.7.1: Decode_Text

Pspec generated
22 February 1993 by lyle

DESCRIPTION

Repeat until no Imbedded_Text_Codes remain:

if (Text_Code Translation exists for currently selected language)
Replace Imbedded_Text_Code with language Translation.
elseif (Text_Code Translation exists for English)
Replace Imbedded_Text_Code with English Translation.
else
Replace Imbedded_Text_Code with " Unknown Message ".
endif End_Repeat

END PSPEC
```

6.1.1.1.2.2.7.2. Functional Requirement Get_Coded_Translation a. Inputs

*Language_Code* ::= "enumerated"
   from: Decode_Text
*Text_Code* ::= "unsigned short integer"
   from: Decode_Text
*Translation_Language* ::= "integer"
   from: Translation_Tables
*Translation_Text* ::= "byte or word array"
   from: Translation_Tables
*UCS2_Conversion_Table* ::= {UCS2}
   from: Language_Conversion_Tables b. Outputs

*Coded_Text* ::= Coded_Text_Body + Text_Terminator
    to: Decode_Text c. Processing

```
Process 1.1.1.2.2.7.2: Get_Coded_Translation

Pspec generated
22 February 1993 by lyle

DESCRIPTION

Lookup Translation_Text using given Text_Code and Language_Code.
Convert Translation_Text into Coded_Text format using Translation_Language.
Send Coded_Text.

END PSPEC
```

6.1.1.1.2.3. Functional Requirement Update_Audio_Output

This process dynamically controls output of audio sounds on the user display. Audio_Status is used to identify which tones to generate. Audio_Commands are generated to turn on/off/repeat the audio tones.

a. Inputs

*Audio_Status* ::= Audio_Code + Audio_Forever_Flag + Audio_Duration + Audio_Tone_State + Audio_Base_Time
    from: Offpage.1.1.1.2
*UI_Status* ::= UI_Status_Semaphore + Screen_Status + Audio_Status + Light_Status
    from: Offpage.1.1.1.2
*UI_Tables* ::= Screen_Tables
    from: Offpage.1.1.1.2 b. Outputs

*Audio_Command*
    to: Offpage.1.1.1.2
*Audio_Status* ::= Audio_Code + Audio_Forever_Flag + Audio_Duration + Audio_Tone_State + Audio_Base_Time
    to: Offpage.1.1.1.2
*UI_Status* ::= UI_Status_Semaphore + Screen_Status + Audio_Status + Light_Status to: Offpage.1.1.1.2
c. Processing
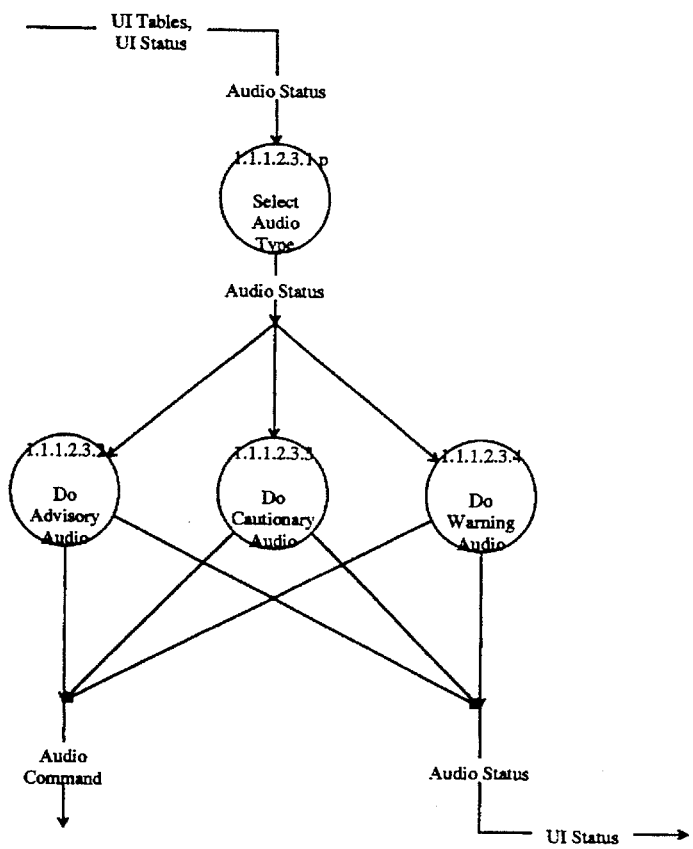
Figure 11. Data Flow Diagram 1.1.1.2.3: Update_Audio_Output
6.1.1.1.2.3.1. Functional Requirement Select_Audio_Type
This process determines the type of audio tone to be generated and passes the Audio_Status on to the appropriate process.
a. Inputs
*Audio_Status* ::= Audio_Code + Audio_Forever_Flag + Audio_Duration + Audio_Tone_State + Audio_Base_Time
from: Offpage.1.1.1.2.3

*UI_Status* ::= UI_Status_Semaphore + Screen_Status + Audio_Status + Light_Status
   from: Offpage.1.1.1.2.3
*UI_Tables* ::= Screen_Tables
   from: Offpage.1.1.1.2.3 b. Outputs

*Audio_Status* ::= Audio_Code + Audio_Forever_Flag + Audio_Duration + Audio_Tone_State + Audio_Base_Time
   to: Do_Advisory_Audio
   to: Do_Cautionary_Audio
   to: Do_Warning_Audio c. Processing

```
Process 1.1.1.2.3.1: Select_Audio_Type

Pspec generated
3 February 1993 by lyle

DESCRIPTION

Send Audio_Status based upon Audio_Status Audio_Code.

END PSPEC
```

6.1.1.1.2.3.2. Functional Requirement Do_Advisory_Audio

This process manages "Advisory" audio tones.

a. Inputs

*Audio_Status* ::= Audio_Code + Audio_Forever_Flag + Audio_Duration + Audio_Tone_State + Audio_Base_Time
   from: Select_Audio_Type b. Outputs

*Audio_Command*
   to: Offpage.1.1.1.2.3
*Audio_Status* ::= Audio_Code + Audio_Forever_Flag + Audio_Duration + Audio_Tone_State + Audio_Base_Time
   to: Offpage.1.1.1.2.3
*UI_Status* ::= UI_Status_Semaphore + Screen_Status + Audio_Status + Light_Status to: Offpage.1.1.1.2.3 c. Processing

6.1.1.1.2.3.3. Functional Requirement Do_Cautionary_Audio

This process manages "Cautionary" audio tones.

a. Inputs

*Audio_Status* ::= Audio_Code + Audio_Forever_Flag + Audio_Duration + Audio_Tone_State + Audio_Base_Time
from: Select_Audio_Type b. Outputs

*Audio_Command*
to: Offpage.1.1.1.2.3
*Audio_Status* ::= Audio_Code + Audio_Forever_Flag + Audio_Duration + Audio_Tone_State + Audio_Base_Time
to: Offpage.1.1.1.2.3
*UI_Status* ::= UI_Status_Semaphore + Screen_Status + Audio_Status + Light_Status
to: Offpage.1.1.1.2.3 c. Processing

6.1.1.1.2.3.4. Functional Requirement Do_Warning_Audio

This process manages "Warning" audio tones.

a. Inputs

*Audio_Status* ::= Audio_Code + Audio_Forever_Flag + Audio_Duration + Audio_Tone_State + Audio_Base_Time
from: Select_Audio_Type b. Outputs

*Audio_Command*
to: Offpage.1.1.1.2.3
*Audio_Status* ::= Audio_Code + Audio_Forever_Flag + Audio_Duration + Audio_Tone_State + Audio_Base_Time
to: Offpage.1.1.1.2.3

*UI_Status* ::= UI_Status_Semaphore + Screen_Status + Audio_Status + Light_Status
   to: Offpage.1.1.1.2.3 c. Processing

6.1.1.1.2.4. Functional Requirement Update_Light_Output

This process update the display of physical lights on the User Interfact device.

a. Inputs

*Light_Status* ::= Current_Light_Status + New_Light_Status
   from: Offpage.1.1.1.2
*UI_Status* ::= UI_Status_Semaphore + Screen_Status + Audio_Status + Light_Status
   from: Offpage.1.1.1.2
*UI_Tables* ::= Screen_Tables
   from: Offpage.1.1.1.2 b. Outputs

*Light_Command*
   to: Offpage.1.1.1.2
*Light_Status* ::= Current_Light_Status + New_Light_Status
   to: Offpage.1.1.1.2
*UI_Status* ::= UI_Status_Semaphore + Screen_Status + Audio_Status + Light_Status
   to: Offpage.1.1.1.2 c. Processing

```
Process 1.1.1.2.4: Update_Light_Output

Pspec generated
3 February 1993 by lyle

DESCRIPTION if (Current_Light_Status != New_Light_Status)

Send Light_Command = New_Light_Status All_Light_Status.
Current_Light_Status = New_Light_Status.

endif

END PSPEC
```

6.1.1.1.3. Functional Requirement Process_Touch_Task

This process identifies changes in button status from the Display Controller and generates any resulting User_Function_Msg or Edit_Info flows.

Note: The long term intention is that this process is triggered on receipt of Button_Status information which comes asynchronously from the Display Controller. Until asynchronous commands from the Display Controller are implemented, Update_Display_Task will poll the Display Controller for button change information and pass it on to this process.

a. Inputs

*Display_Touch_Status* ::= {Display_Touch_State}
      . from: Interface_Display
    *UI_Status* ::= UI_Status_Semaphore + Screen_Status + Audio_Status + Light_Status
      from: UI_Status
    *UI_Tables* ::= Screen_Tables
      from: UI_Tables b. Outputs

*Edit_Info* ::= Value_Object + Edit_Type + Edit_Qid
      to: Offpage.1.1.1
    *User_Function_Msg* ::= [Function_Code_Msg | Keyboard_Code_Msg]
      to: Offpage.1.1.1 c. Processing

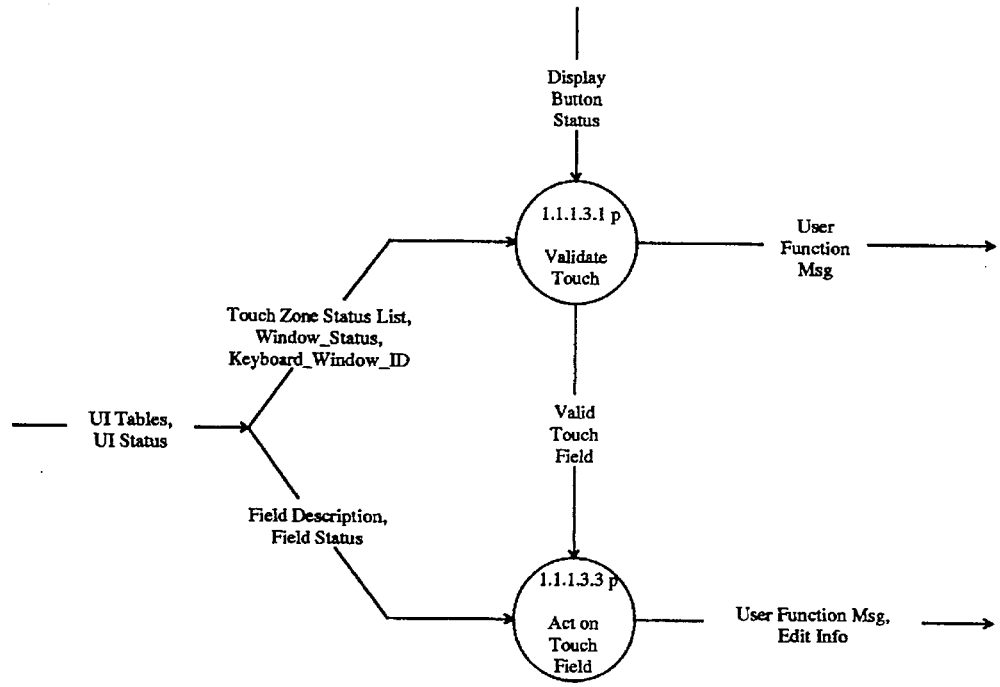

Figure 12. Data Flow Diagram 1.1.1.3: Process_Touch_Task

Validate_Touch is the driving process.

(Note: Until asynchronous button event Command Packets are implemented in the Display Processor, this task will awaken every 0.05s and request current button status from the Display Processor.)

6.1.1.1.3.1. Functional Requirement Validate_Touch a. Inputs

*Display_Button_Status*
   from: Offpage.1.1.1.3
*Keyboard_Window_ID* ::= "Window_ID"
   from: Offpage.1.1.1.3
*Touch_Zone_Status_List* ::= {Touch_Zone_Status}
   from: Offpage.1.1.1.3
*UI_Status* ::= UI_Status_Semaphore + Screen_Status + Audio_Status + Light_Status
   from: Offpage.1.1.1.3
*UI_Tables* ::= Screen_Tables
   from: Offpage.1.1.1.3
*Window_Status* ::= Region_Code + Next_Window_ID + Parent_Window_ID + Window_Flags + Child_Window_-

ID + Window_Description_Ptr + Display_Frame_Number + Window_Data_Ptr + User_Function_Qid + Field_Status_List
   from: Offpage.1.1.1.3 b. Outputs

*User_Function_Msg* ::= [Function_Code_Msg | Keyboard_Code_Msg]
   to: Offpage.1.1.1.3
*Valid_Touch_Field* ::= Window_ID + Field_Index + Touch_Status
   to: Act_on_Touch_Field c. Processing

```
Process 1.1.1.3.1: Validate_Touch

Pspec generated
12 February 1993 by lyle

DESCRIPTION if (Emergency Stop button pressed)
Send User_Function_Msg = EMERGENCY_STOP_USER_FUNCTION to Procedure Driver.
endif if      (Display_Button_Status contains a keyboard input character)
AND (Keyboard_Window_ID is defined)
Send Keyboard_Character in UCS2 format to Window_Status.User_Function_Qid.
endif for button = 0 to MAX_DISPLAY_BUTTON_NUMBER - 1 if      (Button_Status = NEW)
AND (Display_Button_State = UNTOUCHED)
Set Button_Status = UNTOUCHED.
endif if (Button_Status != NEW)

if (Display_Button_State = TOUCHED)
if (Button_Status = TOUCHED)
Button_State = HELD.
else
Button_State = NEWLY_PRESSED.
endif else if (Button_Status = UNTOUCHED)
Ignore this button.
else
Button_State = RELEASED.
```

```
endif endif endif

/* Only send Valid_Touch_Field if Window_Status is valid */
if (Window_Status.Window_Flags does not contain MARKED_FOR_DELETE_WINDOW_FLAG)
Send Valid_Touch_Field.
endif endfor

END PSPEC
```

6.1.1.1.3.2. Functional Requirement Act_on_Touch_Field a. Inputs

*Field_Description* ::= Field_Code + Field_Attributes + Display_Location + Field_Data_Type + Field_Format + Font_Code + Value_Code + User_Function_Code + Initial_Field_Colors_Code + Field_Format_Type + Field_Constant
    from: Offpage.1.1.1.3
*Field_Status* ::= Value_Modified + Scroll_Page_Number + Current_Field_Colors_Code + Current_Field_Attributes + Field_Value_List
    from: Offpage.1.1.1.3
*UI_Status* ::= UI_Status_Semaphore + Screen_Status + Audio_Status + Light_Status
    from: Offpage.1.1.1.3
*UI_Tables* ::= Screen_Tables
    from: Offpage.1.1.1.3
*Valid_Touch_Field* ::= Window_ID + Field_Index + Touch_Status
    from: Validate_Touch b. Outputs

*Edit_Info* ::= Value_Object + Edit_Type + Edit_Qid
    to: Offpage.1.1.1.3
*User_Function_Msg* ::= [Function_Code_Msg | Keyboard_Code_Msg]
    to: Offpage.1.1.1.3 c. Processing

```
Process 1.1.1.3.3: Act_on_Touch_Field
```

```
Pspec generated
12 February 1993 by lyle

DESCRIPTION if (field is editable in Field_Description)

Send Edit_Info.

elseif (field is INTERNAL)

if (Function_Code = NEXT_PAGE or PREVIOUS_PAGE)
Find SCROLLABLE field in Window Field_Description_List.
if (Function_Code = NEXT_PAGE)
increment Field_Status.Scroll_Page_Number.
else
decriment Field_Status.Scroll_Page_Number.
endif
Set Field_Status.Value_Modified flag.
endif else Send User_Function_Msg.

endif

END PSPEC
```

6.1.1.1.4. Functional Requirement Interface_Display

This is a subsystem of procedures which manage the Display Controller. These procedures format all Commands and Responses going to and comming from the Display Controller. They handle all interface requirements with the MPU's Communication Manager.

a. Inputs

*Audio_Command*
  from: Update_Display_Task
*Command_from_Display_Msg*
  from: Offpage.1.1.1
*Light_Command*
  from: Update_Display_Task
*Response_from_Display* from: Offpage.1.1.1
*Screen_Command*
   from: Update_Display_Task b. Outputs

*Command_to_Display*
   to: Offpage.1.1.1
*Display_Touch_Status* ::= {Display_Touch_State}
   to: Process_Touch_Task
*Response_to_Display*
   to: Offpage.1.1.1 c. Processing

6.1.1.1.5. Functional Requirement UI_Diagnostics

To be determined at a future date.

a. Inputs

*Diagnostic_Command*
   from: Offpage.1.1.1 b. Outputs

*Diagnostic_Data*
   to: Offpage.1.1.1 c. Processing

6.1.1.2. Functional Requirement Edit_Data

Edit_Data is a "object-oriented" utility which permits the user to enter or modify values used within the Yoda system. It relies on information about the "Value_Objects" found in the Value_Description_Table in order to be understand formatting requirements and editing limits of the value to be edited. Edit_Data displays an appropriate "Edit Window", manages all editing operations, and returns the edited value via a queue message via User_Data.

a. Inputs

*Edit_Info* ::= Value_Object + Edit_Type + Edit_Qid
  from: Offpage.1.1
  from: Control_User_Inteface
*User_Function_Msg* ::= [Function_Code_Msg | Keyboard_Code_Msg]
  from: Control_User_Inteface
*Value_Description_Tables* ::= Value_Table + Emumeration_Table
  from: Value_Description_Tables
*Window_ID* ::= "int"
  from: Control_User_Inteface b. Outputs

*User_Data_Msg* ::= Msg_Type + Window_ID + Value_Object
  to: Offpage.1.1
*Window_Command* ::= [Open_Window_Command | Front_Window_Command | Close_Window_Command | Set_-Window_Mode_Command | Set_Audio_Command | Set_Lights_Command]
  to: Control_User_Inteface
*Window_Data* ::= Window_Data_Semaphore + Window_Data_Value_List
  to: Control_User_Inteface c. Processing

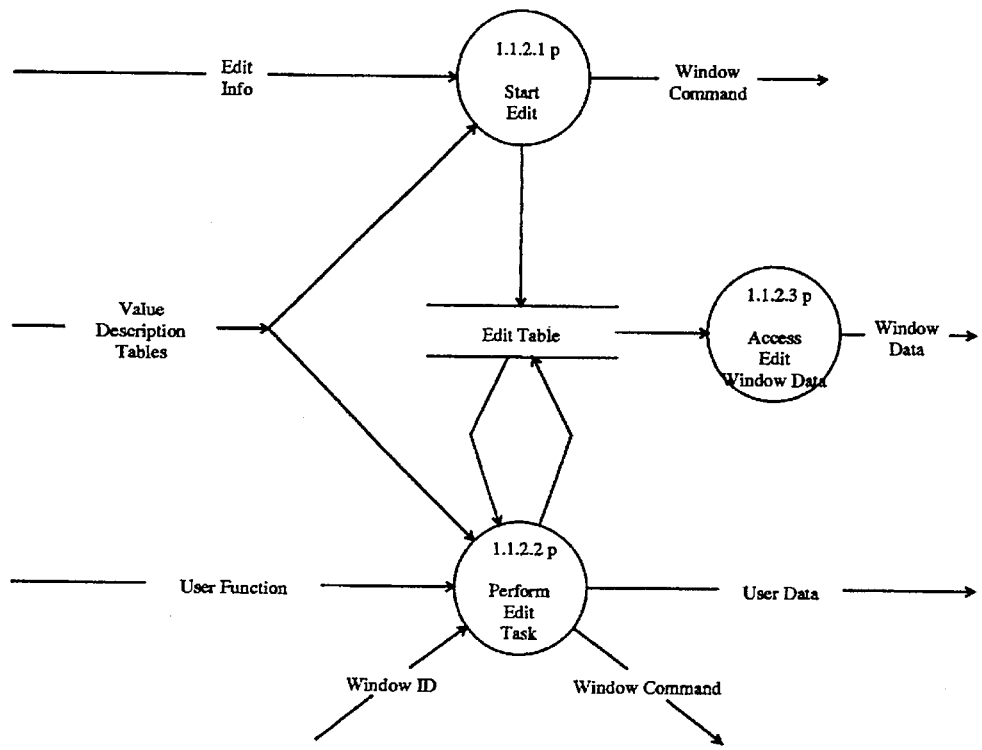

Figure 13. Data Flow Diagram 1.1.2: Edit_Data

Start_Edit is a callable interface used to initiate the editing process.

Access_Window_Data is a non-existant process. It is only shown in order to make the diagramming rules happy. Window_Data is accessed directly out of the Edit_Table data store.

6.1.1.2.1. Functional Requirement Start_Edit

Start_Edit is a callable procedure. It creates an edit window to edit the requested data and establishes information in the Edit_Table data store.

a. Inputs

*Edit_Info* ::= Value_Object + Edit_Type + Edit_Qid
        from: Offpage.1.1.2
    *Value_Description_Tables* ::= Value_Table + Enumeration_Table
        from: Offpage.1.1.2 b. Outputs

*Edit_Table* ::= Edit_Table_Semaphore + Edit_Job_Count + Edit_Job_List
 to: Edit_Table
*Window_Command* ::= [Open_Window_Command | Front_Window_Command | Close_Window_Command | Set_-Window_Mode_Command | Set_Audio_Command | Set_Lights_Command]
 to: Offpage.1.1.2 c. Processing

```
Process 1.1.2.1: Start_Edit

Pspec generated
23 December 1992 by lyle

DESCRIPTION

Grab the Edit_Table_Semaphore.

Find a free Edit_Job structure in the Edit_Job_List, initialize
its data area, and create the appropriate type of edit window.

Release the Edit_Table_Semaphore.

END PSPEC
```

6.1.1.2.2. Functional Requirement Perform_Edit_Task

The Perform_Edit_Task relies on Start_Edit to create the initial editing window and to define its editing parameters in Edit_Table. It then manages the editing process until the user enters the new data or cancels the edit request. It is able support multiple edits in-process simultaneously.

a. Inputs

*Edit_Table* ::= Edit_Table_Semaphore + Edit_Job_Count + Edit_Job_List
 from: Edit_Table
*User_Function*
 from: Offpage.1.1.2
*Value_Description_Tables* ::= Value_Table + Enumeration_Table
 from: Offpage.1.1.2
*Window_ID* ::= "int"
 from: Offpage.1.1.2 b. Outputs

*Edit_Table* ::= Edit_Table_Semaphore + Edit_Job_Count + Edit_Job_List
   to: Edit_Table
*User_Data*
   to: Offpage.1.1.2
*Window_Command* ::= [Open_Window_Command | Front_Window_Command | Close_Window_Command | Set_-
Window_Mode_Command | Set_Audio_Command | Set_Lights_Command]
   to: Offpage.1.1.2 c. Processing

```
Process 1.1.2.2: Perform_Edit_Task

Pspec generated
23 December 1992 by lyle

DESCRIPTION

On receipt of a User_Function
{
Grab the Edit_Table_Semaphore.

Lookup the Edit_Job associated with the User_Function.

If the User_Function is an editing function (digit, character, CLEAR, ...)
Modify the New_Value and display results in Window_Data.
ElseIf the User_Function is ENTER
Send New_Value out to the Edit_Qid as User_Data.

If the User_Function was CANCEL or ENTER
Mark the Edit_Job structure as free in the Edit_Job_List.

Release the Edit_Table_Semaphore.
}

END PSPEC
```

6.1.1.2.3. Functional Requirement Access_Edit_Window_Data

Access_Edit_Window_Data is a dummy process. Window_Data passes directly out of the data store and into the Window_Manager.

a. Inputs

*Edit_Table* ::= Edit_Table_Semaphore + Edit_Job_Count + Edit_Job_List
   from: Edit_Table b. Outputs

*Window_Data* ::= Window_Data_Semaphore + Window_Data_Value_List
   to: Offpage.1.1.2 c. Processing

```
Process 1.1.2.3: Access_Edit_Window_Data

Pspec generated
23 December 1992 by lyle

DESCRIPTION

/* This is a "dummy process" just to make StP happy.
 * Window_Data is accessed directly by the Window Manager.
 */

END PSPEC
```

What is claimed is:

1. A processing system for processing fluids for medical purposes including a user interactive interface, the system comprising an array of hardware elements, control means for actuating the hardware elements to carry out a predetermined fluid processing procedure, the control means including an output for transmitting a processing status value that changes over time as the hardware elements carry out the fluid processing procedure, an interface screen having a first display region and a second display region spaced and distinct from the first display region, an interface manager communicating with the interface screen and the control means output, the interface manager including means for generating a first display including a first touch activated field and another field displaying the changing processing status value in response to the control means output, means for generating a second display different than the first display, means for generating a third display different than the first and second display, means for showing the first display in the first region to display changes in the processing status value in response to the control means output, means for showing the second display in the second region while simultaneously keeping the first display showing in the first region to display changes in the processing status value, and means responsive to touching the first touch activated field in the first display while the second display is showing in the second region for thereafter blanking the second display and showing the third display in the second region while simultaneously keeping the first display showing in the first region to display changes in the processing status value.

2. A system according to claim 1 wherein the means for generating the first display includes means for generating a second touch activated field in the first display different than the first touch activated field, and wherein the interface manager further includes means responsive to touching the second touch activated field in the first display while the third display is showing in the second region for thereafter blanking the third display and showing the second display in the second region while simultaneously keeping the first display showing in the first region to display changes in the processing status value.

3. A system according to claim 1 wherein the means for generating the first display including means for generating a second touch activated field in the first display different than the first touch activated field, and wherein the interface manager includes means for showing the second display in the second region whenever the second touch activated field is touched while simultaneously keeping the first display showing in the first region to display changes in the processing status value.

4. A whole blood processing system including an array of hardware elements, and control means for actuating the hardware elements to carry out a predetermined fluid processing procedure, the control means including first program means for defining the functional steps of the procedure and generating prescribed abstract function selection commands based upon the defined steps, second program means communicating with the first program means for generating specific hardware selection commands in response to receiving the function selection commands generated by the first program means, and peripheral control means communicating with the hardware elements and with the second program means, and not with the first program means, for actuating the hardware elements in response to receiving the hardware selection commands generated by the second program means.

5. A system for specifying a user interface in a whole blood processing apparatus, the system comprising an interface device, first program means for generating prescribed abstract display selection commands, second program means communicating with the first program means for generating specific format control commands in response to receiving the display selection commands generated by the first program means, and interface control means communicating with the interface device and with the second program means, and not with the first program means, for creating a display on the interface device in response to receiving the format control commands generated by the second program means.

6. A system according to claim 5 wherein the display created by the interface control means includes at least one touch activated field, wherein the interface control means is operative for generating a selected touch indicator code in response to touching the touch activated field for transmittal to the second program means, wherein the second program means is operative for transmitting a function control code to the first programming means in response to receipt of the selected touch indicator code, and wherein the first programming means includes means for generating output based upon the function control code.

* * * * *

UNITED STATES PATENT AND TRADEMARK OFFICE
CERTIFICATE OF CORRECTION

PATENT NO.    : 5,581,687
DATED         : December 3, 1996
INVENTOR(S)   : Lyle et al.

It is certified that error appears in the above-identified patent and that said Letters Patent is hereby corrected as shown below:

Column 3,
Line 51, delete "thee" and substitute -- the --

Column 13,
Line 67, before "present" delete "it" and substitute -- its --

Column 14,
Line 27, delete "selected" and substitute -- selection --

Column 15,
Line 27, delete ";"

Column 17,
Line 44, delete ";"

Column 18,
Line 10, delete "and"
Line 66, delete "56" (first occurrence) and substitute -- 50 --

Signed and Sealed this

Seventeenth Day of August, 2004

JON W. DUDAS
*Acting Director of the United States Patent and Trademark Office*